US011986582B2

(12) United States Patent
Friederichs et al.

(10) Patent No.: US 11,986,582 B2
(45) Date of Patent: May 21, 2024

(54) MEDICAMENT PREPARATION AND TREATMENT DEVICES, METHODS, AND SYSTEMS

(71) Applicant: NxStage Medical, Inc., Lawrence, MA (US)

(72) Inventors: Goetz Friederichs, Beverly, MA (US); William K. Weigel, Portland, ME (US); Dennis M. Treu, Castle Rock, CO (US); Jeffrey H. Burbank, Manchester, MA (US); James M. Brugger, Newburyport, MA (US); Keith David J. Wheeler, Tyngsboro, MA (US); Scott W. Newell, Ipswich, MA (US)

(73) Assignee: NxStage Medical, Inc., Lawrence, MA (US)

( * ) Notice: Subject to any disclaimer, the term of this patent is extended or adjusted under 35 U.S.C. 154(b) by 242 days.

(21) Appl. No.: 17/511,348

(22) Filed: Oct. 26, 2021

(65) Prior Publication Data
US 2022/0047790 A1 Feb. 17, 2022

Related U.S. Application Data

(63) Continuation of application No. 16/575,482, filed on Sep. 19, 2019, now Pat. No. 11,167,069, which is a
(Continued)

(51) Int. Cl.
*A61M 1/16* (2006.01)
*A61K 31/191* (2006.01)
(Continued)

(52) U.S. Cl.
CPC ......... *A61M 1/1666* (2014.02); *A61K 31/191* (2013.01); *A61M 1/1524* (2022.05);
(Continued)

(58) Field of Classification Search
CPC .. A61M 1/1666; A61M 1/1524; A61M 1/154; A61M 1/155; A61M 1/1561;
(Continued)

(56) References Cited

U.S. PATENT DOCUMENTS 4,155,852 A  5/1979 Fischel et al.
4,586,928 A  5/1986 Barnes et al.
(Continued)

FOREIGN PATENT DOCUMENTS

WO  2000057935 A1  10/2000
WO  2003099356 A2  12/2003
(Continued)

OTHER PUBLICATIONS

Extended European Search Report dated Feb. 13, 2020 for European Patent Application No. 19207715.4.
(Continued)

*Primary Examiner* — Richard C Gurtowski
(74) *Attorney, Agent, or Firm* — Potomac Law Group, PLLC

(57) ABSTRACT

A medicament preparation system includes a water purification module and a medicament proportioning module that is interoperable with a replaceable fluid circuit. The fluid circuit includes a purified water inlet, a product medicament outlet, and a plurality of pumping tube segments. At least a first concentrate container is connected by at least a portion of the fluid circuit to the product medicament output and a first concentration measurement sensor station is positioned in a flow path. A controller is programmed to calculate iteratively a concentration of a first concentrate from the first concentrate container and the purified water from a signal generated by the first concentration measurement sensor station and to regulate one or both of a first pumping actuator engaged with the first pumping tube segment and a second
(Continued)

pumping actuator engaged with the second pumping tube segment, responsively to the concentration of the first concentrate and water.

20 Claims, 28 Drawing Sheets

Related U.S. Application Data continuation of application No. 15/514,230, filed as application No. PCT/US2015/052385 on Sep. 25, 2015, now Pat. No. 10,478,544.

(60) Provisional application No. 62/055,022, filed on Sep. 25, 2014.

(51) Int. Cl.
| | | |
|---|---|---|
| *A61M 1/14* | (2006.01) | |
| *A61M 1/36* | (2006.01) | |
| *B01F 21/20* | (2022.01) | |
| *C02F 9/00* | (2023.01) | |
| *F15B 1/04* | (2006.01) | |
| C02F 1/20 | (2023.01) | |
| C02F 1/28 | (2023.01) | |
| C02F 1/42 | (2023.01) | |
| C02F 1/44 | (2023.01) | |
| C02F 103/02 | (2006.01) | |
| C02F 103/04 | (2006.01) | |

(52) U.S. Cl.
CPC ............ *A61M 1/154* (2022.05); *A61M 1/155* (2022.05); *A61M 1/1561* (2022.05); *A61M 1/1562* (2022.05); *A61M 1/1565* (2022.05); *A61M 1/1658* (2013.01); *A61M 1/166* (2014.02); *A61M 1/362227* (2022.05); *A61M 1/36224* (2022.05); *A61M 1/36225* (2022.05); *A61M 1/362261* (2022.05); *A61M 1/362262* (2022.05); *A61M 1/362265* (2022.05); *B01F 21/20* (2022.01); *C02F 9/00* (2013.01); *F15B 1/04* (2013.01); *A61M 1/1563* (2022.05); *A61M 1/362263* (2022.05); *A61M 2205/3317* (2013.01); *A61M 2205/3368* (2013.01); *A61M 2205/502* (2013.01); *A61M 2205/6054* (2013.01); *A61M 2205/6072* (2013.01); *C02F 1/20* (2013.01); *C02F 1/283* (2013.01); *C02F 1/42* (2013.01); *C02F 2001/425* (2013.01); *C02F 2001/427* (2013.01); *C02F 1/44* (2013.01); *C02F 2103/026* (2013.01); *C02F 2103/04* (2013.01); *C02F 2209/05* (2013.01); *C02F 2209/445* (2013.01); *F15B 2201/315* (2013.01); *Y02A 50/30* (2018.01)

(58) Field of Classification Search
CPC .............. A61M 1/1562; A61M 1/1565; A61M 1/1658; A61M 1/166; A61M 1/362227; A61M 1/36224; A61M 1/36225; A61M 1/362261; A61M 1/362262; A61M 1/362265; A61M 1/1563; A61M 1/362263
See application file for complete search history.

(56) References Cited

U.S. PATENT DOCUMENTS

| | | |
|---|---|---|
| 2002/0119482 A1 | 8/2002 | Nelson et al. |
| 2005/0133370 A1 | 6/2005 | Park et al. |
| 2007/0196479 A1* | 8/2007 | Willmann ............... G16B 45/00 |
| | | 702/19 |
| 2008/0017194 A1 | 1/2008 | Hassanein et al. |
| 2008/0210560 A1 | 9/2008 | Barringer |
| 2008/0311672 A1 | 12/2008 | Dasgupta et al. |
| 2012/0083046 A1 | 4/2012 | Watson et al. |
| 2012/0273354 A1 | 11/2012 | Orhan et al. |
| 2013/0184638 A1 | 7/2013 | Scarpaci et al. |
| 2013/0190681 A1 | 7/2013 | Jansson et al. |
| 2018/0140761 A1* | 5/2018 | Rovatti ............... A61M 1/3406 |

FOREIGN PATENT DOCUMENTS

| | | |
|---|---|---|
| WO | 2006074429 A1 | 7/2006 |
| WO | 2007118235 A2 | 10/2007 |
| WO | 2008065470 A1 | 6/2008 |
| WO | 2008106538 A2 | 9/2008 |
| WO | 2011137266 A1 | 11/2011 |
| WO | 2013114063 A1 | 8/2013 |
| WO | 2014117000 A2 | 7/2014 |

OTHER PUBLICATIONS

Extended European Search Report for European Patent Application No. 15845085.8 dated May 11, 2018.
Extended European Search Report issued in application 19178156.6 dated Sep. 16, 2019.
International Preliminary Report on Patentability (Chapter I) issued in Application No. PCT/US2015/052385 dated Mar. 28, 2017, including Written Opinion of the International Searching Authority dated Mar. 3, 2016.
International Search Report issued in Application No. PCT/US2015/052385 dated Mar. 3, 2016.

* cited by examiner

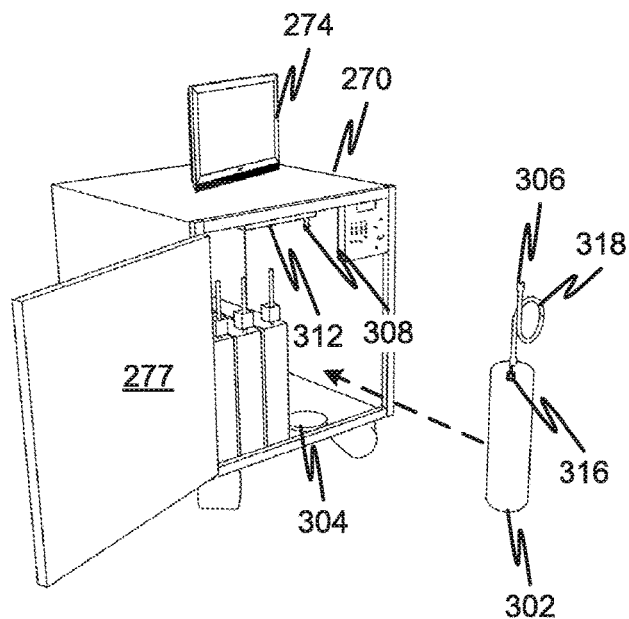 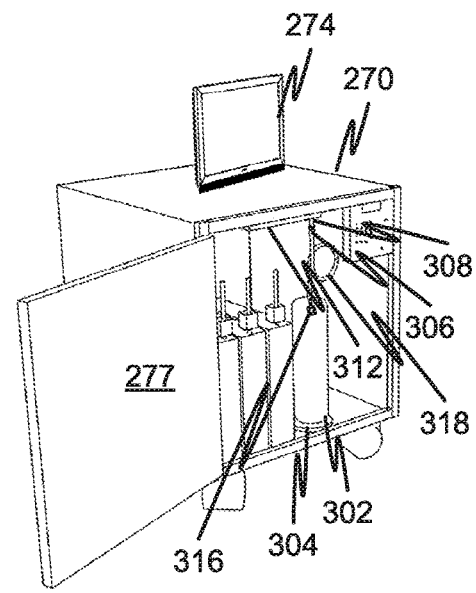
Fig. 6A        Fig. 6B
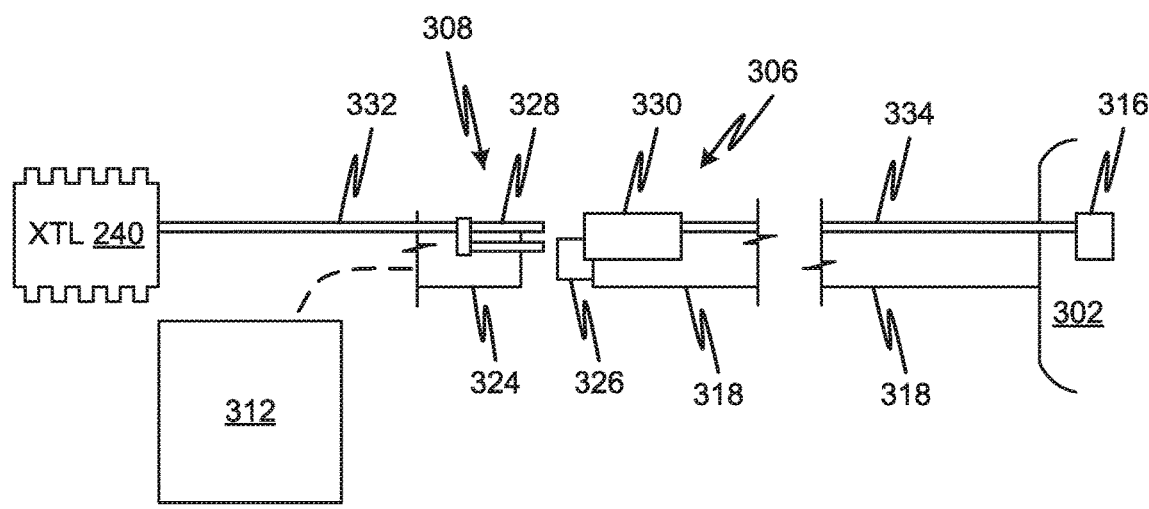
Fig. 6C

MEDICAMENT PREPARATION AND TREATMENT DEVICES, METHODS, AND SYSTEMS

CROSS-REFERENCE TO RELATED APPLICATIONS

This application is a continuation of U.S. application Ser. No. 16/575,482, filed Sep. 19, 2019, which is a continuation of U.S. application Ser. No. 15/514,230, filed Mar. 24, 2017, which is a U.S. national stage filing under 35 U.S.C. § 371 of International Application No. PCT/US2015/052385, filed Sep. 25, 2015, which claims the benefit of U.S. Provisional Application No. 62/055,022, filed Sep. 25, 2014, each of which are hereby incorporated by reference in their entireties.

FIELD

The presently disclosed subject matter relates generally to medical treatment. In details of embodiments, the disclosed subject matter relate to medical fluid preparation and utilization in the performance of medical treatments.

BACKGROUND

There are many types of blood processing and fluid exchange procedures, each providing different therapeutic effects and demanding different processing criteria. Some procedures entail the removal of blood or another fluid from an individual and the return of blood or another fluid to the individual in a controlled fashion. Other types use natural body tissues to exchange blood components with a medicament. Examples of such procedures include hemofiltration (HF), hemodialysis (HD), hemodiafiltration (HDF), and peritoneal dialysis (PD). A common requirement of such procedures is the provision of large quantities of medicament such as dialysate that has a precise mixture of solute components and is free of contaminants and pyrogenic materials.

Known systems for preparing medicaments such as dialysate are continuous proportioning systems and batch mixing systems. Carrying out treatment procedures using medicaments may employ special-purpose machinery. In the dialysis treatments listed above, devices called cyclers are often used. These pump fluid and may also pump blood, depending on the treatment. In the process of pumping, they precisely proportion the net amounts of fluid supplied and discharged and ensure safety by various means including monitoring of pressure, temperature, leaks, and other treatment conditions. In principle, these treatments are relatively simple, but because of the need for patient safety and health outcomes, treatment procedures and treatment systems are complex.

Home delivery of these treatments raises concerns about safety and treatment efficacy. One of the drawbacks of home treatment is the need for a supply of purified water. In clinics, large reverse osmosis plants provide a continuous supply of purified water. In the home, such large systems may not be practical because they require high volume of water and drainage. Installing and using relevant components can be a difficult and expensive task and may require modifications to a patient's home. In addition, the systems for the production of properly mixed medicaments in pure form require a high level of precision and safeguards as well as training and maintenance. To provide effective and safe systems for home delivery of blood treatments, there is an on-going need for innovations in these areas and others.

SUMMARY

A medicament preparation system, according to an embodiment, includes a water purification module and a medicament proportioning module. The system is configured to allow convenient and safe use in a home environment or a critical care environment as well as others affording safety, reliability, and a compact form factor.

Objects and advantages of embodiments of the disclosed subject matter will become apparent from the following description when considered in conjunction with the accompanying drawings.

BRIEF DESCRIPTION OF DRAWINGS

Embodiments will hereinafter be described in detail below with reference to the accompanying drawings, wherein like reference-numerals represent like elements. The accompanying drawings have not necessarily been drawn to scale. Where applicable, some features may not be illustrated to assist in the description of underlying features.

FIGS. 6A through 6C illustrate features related to installation of replaceable tagged components in a module that consumes them and communication by data carriers with a controller of the module, according to embodiments of the disclosed subject matter.

DETAILED DESCRIPTION

Figure 1:
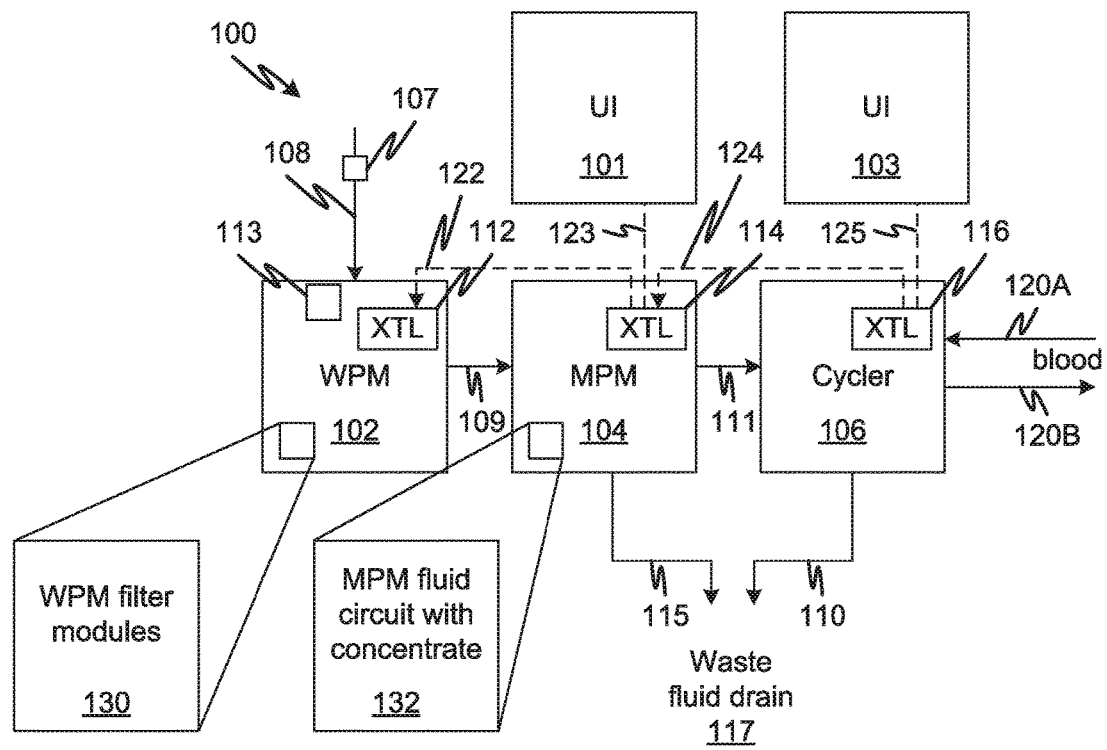
FIG. 1 shows an overview of an online system that includes a water purification module, proportioning medicament proportioning module, and a cycler forming an online treatment system, according to embodiments of the disclosed subject matter.

FIG. 1 shows an overview of an online water purification, proportioning medicament generation, and treatment system 100, according to embodiments of the disclosed subject matter. A water purification module 102 receives tap water 108 from a municipal water supply. The water purification module 102 purifies the water and checks its purity, under control of a controller 112 and using a water quality sensor. The water quality sensor, in embodiments, includes a conductivity sensor. The water purification module 102 utilizes one or more filter modules 130 which are replaced to help maintain the ability to generate product water that is sterile and ultra-pure. Product water 109 from the water purification module 102 is conveyed to a medicament proportioning module 104 which mixes one or more concentrates provided in a replaceable fluid circuit 132 to generate a medicament 111. The medicament concentrate are diluted in a predefined proportion to generate product medicament. One or more concentrate materials may be utilized and combined in the product medicament. The water purification and medicament generation are performed in in-line fashion and on-demand, which means water is purified and mixed with medicament concentrate as a continuous process, at a rate of consumption and as demanded by a final consumer, in this case, a cycler 106. Waste produced by the medicament proportioning module 104 is conveyed as indicated at 115 to a drain 117. Waste 110, for example spent medicament, is conveyed to the same or other drain 117.

Each of the water purification module 102, the medicament proportioning module 104, and the cycler 106 may include a respective controller 112, 114, and 116. All of the controllers 112, 114, and 116 may be in communication as indicated by lines 122 and 124. In alternative embodiments a smaller or larger number of controllers may be used and they may be associated with each module 102, 104, 106 or shared among the modules 102, 104, 106. One or more user interfaces, figuratively indicated at 101 and 103 may be connected to one, two, or the entire water purification module 102, medicament proportioning module 104, and/or cycler 106. Connections between the user interfaces 101, 103, indicated at 123 and 125, may be wired or wireless. In embodiments, control may be provided through a single user interface 103 and each module may transmit commands responsive to commands from the user interface 103 to the respective controllers 112 and 114 of the water purification and medicament proportioning modules 102 and 104, in parallel or serially. In embodiments, the cycler 106 receives and returns blood in arterial and venous lines 120A and 120B. In other embodiments, medicament is conveyed to and from a patient, for example in a peritoneal dialysis treatment.

Figure 2:
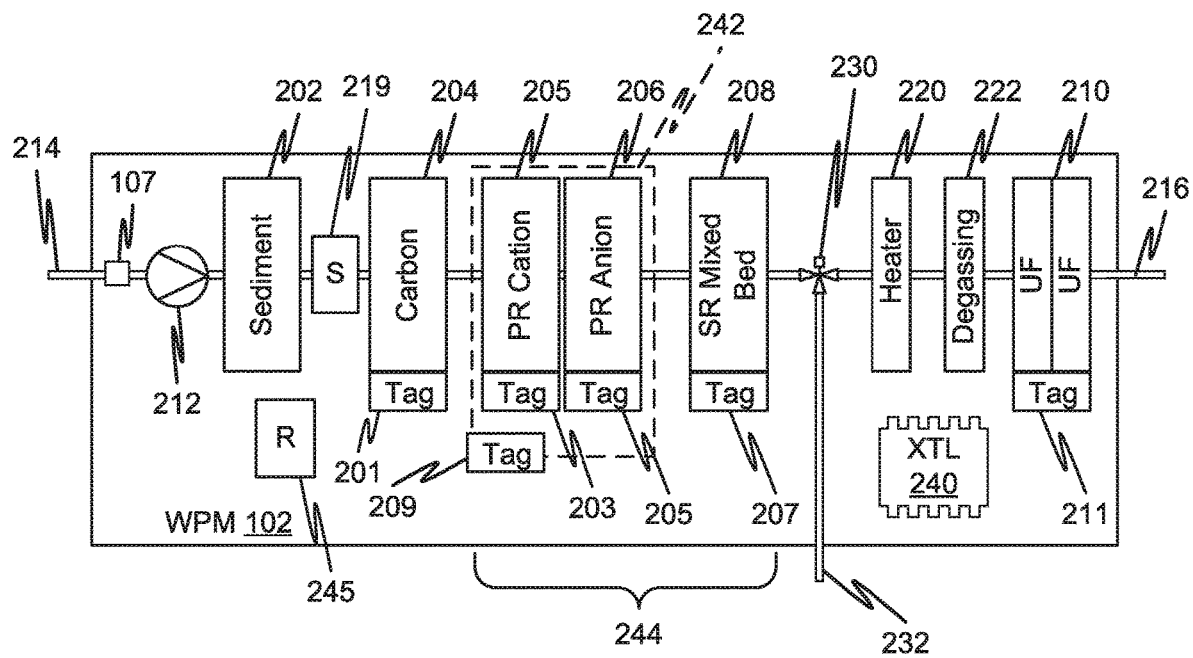
FIG. 2 shows details of the water purification module of the embodiment of FIG. 1, according to embodiments of the disclosure subject matter.

FIG. 2 shows details of the water purification module of the embodiment of FIG. 1. Referring now to FIG. 2, a water purification module 102 receives tap water from an inlet 214, the tap water being pumped by a pump 212 and passed through a sediment filter 202, a water quality sensor station 219, and an activated carbon filter 204. Water from the activated carbon filter 204 is received by a two stage deionization filtration element 244 that includes a primary resin cation stage 205, a primary resin cation stage 206 and a secondary mixed resin bed 208. The primary resin cation stage 205 and primary resin anion stage 206 may be combined in a single replaceable unit 242 or may be separately replaceable. The primary resin cation stage 205, primary resin anion stage 206, and secondary mixed resin bed 28 may also be combined in a single replaceable unit in alternative embodiments. Deionized water from the two stage deionization filtration element 244 passes through a diverter valve 230 which is controlled by a controller 240. The diverter valve 230 may selectively direct a flow of deionized water to a drain outlet 232. Deionized water passing through the diverter valve for the generation of product water is directed to a heater 220, a degassing filter 222, and two or more sterile filters connected in series to form sterile filter stage 210 from which product water may be drawn through a product water outlet 216. A vacuum pump 259 may be provided on an air side of the degassing filter 222. The degassing filter 222 may have a hydrophobic membrane to allow gas to be removed from water flowing through it.

The water quality sensor station 219 may output a signal indicating water quality, for example signal indicating conductivity of the water, which may be numerically cumulated by the controller to generate, for any point in time, a remaining life of any of the filters provided herein. The water quality sensor station 219 may include a particle counter, a conductivity sensor, an optical opacity sensor, a pH sensor, or lab-on-a-chip chemical assay sensor, and/or other type of water quality sensor. The user interface may allow the entry of other data regarding water quality. For example, a worst-case upper bound, or data related thereto, of raw water constituents may be provided. An algorithm that predicts the rate of the various components, based on a measured indicator, may then be used to predict the rate of all contaminant constituents. In an example embodiment, the algorithm may predict that all contaminants are in the same proportion as a predefined value such that an indication of conductivity by the water quality sensor station 219 may thereby indicate the concentrations of the various contaminants. In embodiments, the controller may output an indication of the remaining life of the various components or an indication that a component is at or near expiration. In a particular embodiment, the useful life of the deionization resin beds may be estimated based on conductivity indicated by water quality sensor station 219. The estimation of the remaining life may be based on the data carried by the data carrier of the replaceable tagged component indicating characteristics such as the capacity or type of decontaminating media employed thereby. The water quality sensor station 219 may be positioned at any suitable point downstream of the inlet 214, even though shown downstream of the sediment filter 202.

The pump 212 and sediment filter 202 may form permanent or infrequently-replaced components that are ordinarily not replaced by the user. The entire WPM is adapted for use by a home-bound patient and/or a helper although its features of compact size and low water volume requirement make it attractive for use in critical care environments. The tap water inlet 214 may be fitted with an adapter suitable for connection to an accessible permanent or temporary connection so that, for example in critical care environments, the water purification module 102 may be wheeled to a point of use and connected to a nearby water tap with such a connection fitting. In embodiments, the WPM is combined with the medicament proportioning module 104 in a single housing so that it can be wheeled to a point of use and/or compactly housed for use in a home.

Each of the replaceable components (activated carbon filter 204, primary resin cation stage 205, primary resin anion stage 206, primary resin anion stage 280, replaceable unit 242, or sterile filter stage 210) may be fitted with a respective data carrier 201, 203, 209, 207, 211 such as a bar code or radio frequency identification RFID tag that carries a unique identifier respective to the attached component (again, attached component may be any of the activated carbon filter 204, primary resin cation stage 205, primary resin anion stage 206, primary resin anion stage 280, replaceable unit 242, or sterile filter stage 210 and will generally be referred to as replaceable tagged component). Product water may be drawn through the product water outlet 216.

A reader 245 may be attached to the purification module 102 and may be positioned so as actively or passively to read the data carrier 201, 203, 209, 207, 211 of the replaceable tagged component. Reader 245 may be a scanner for an RFID, a bar code scanner, a smart chip reader, or any other type of data carrier reader and may connect optically, electromagnetically, electrically through conductive contacts, or by any other suitable means. Note that although the term RFID is used, smart tag technology which is also identified as RFID can carry other information besides identifiers. So as the term is used here, data carriers carry any kind of information and RFID can also carry any type of information and transmit the information wirelessly, and passively, to the reader 245 when the RFID device is brought into communication range of the reader 245. The data carriers 201, 203, 209, 207, 211 provide various safety and convenience functions for purposes of maintenance and operation. For example, the reader 245 may be connected to the housing of the water purification module 102, may read the data carriers 201, 203, 209, 207, 211 automatically as they are installed or upon the carrying out a separate scanning step such as the moving of the attached component relative to a scanner.

Figure 3A:
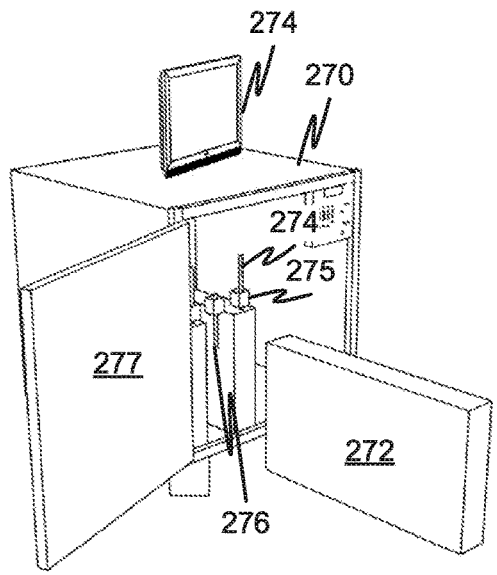
FIGS. 3A and 3B illustrate an optional mechanism that may be provided with the water purification module 102, the medicament proportioning module 104, or any other similar mechanism that receives replaceable tagged components (i.e., ones having data carriers), according to embodiments of the disclosure subject matter.
Figure 3B:
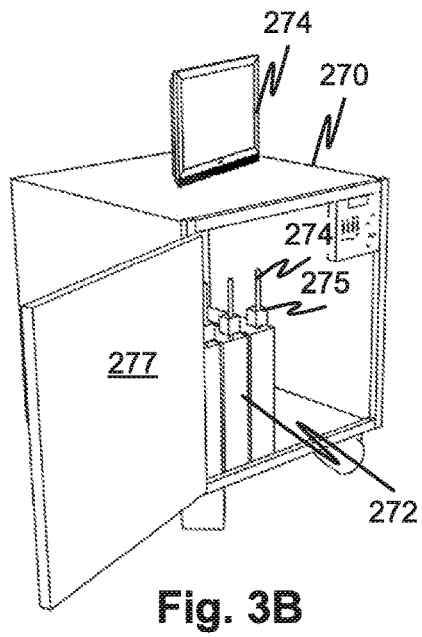

FIGS. 3A and 3B illustrate an optional mechanism that may be provided with a device 270 such as the water purification module 102, the medicament proportioning module 104, or any other similar mechanism that receives replaceable tagged components (i.e., ones having data carriers). A mechanical actuator 275, three of which are illustrated in the figures, selectively moves an interfering element 274 into and out of a loading path of a replaceable tagged component 272. Until a data carrier of the replaceable tagged component 272 is read by a reader, the interfering element 274 blocks the loading path as indicated by the interfering element 276. Once the data carrier of the replaceable tagged component 272 is read, the interfering element interfering element 276 moves into the position shown at 274 of FIG. 3B thereby clearing the loading path and permitting the replaceable tagged component replaceable tagged component 272 to be installed as shown in FIG. 3B. A variety of different types of interfering elements may be provided, for example, one that makes the receiving bay 277 of the replaceable tagged component too small to receive and changes configuration to make it large enough to receive the replaceable tagged component. Other alternatives are also possible, for example, preventing use of the device 270 until the replaceable tagged component 272 data carrier is properly read.

Figure 4:
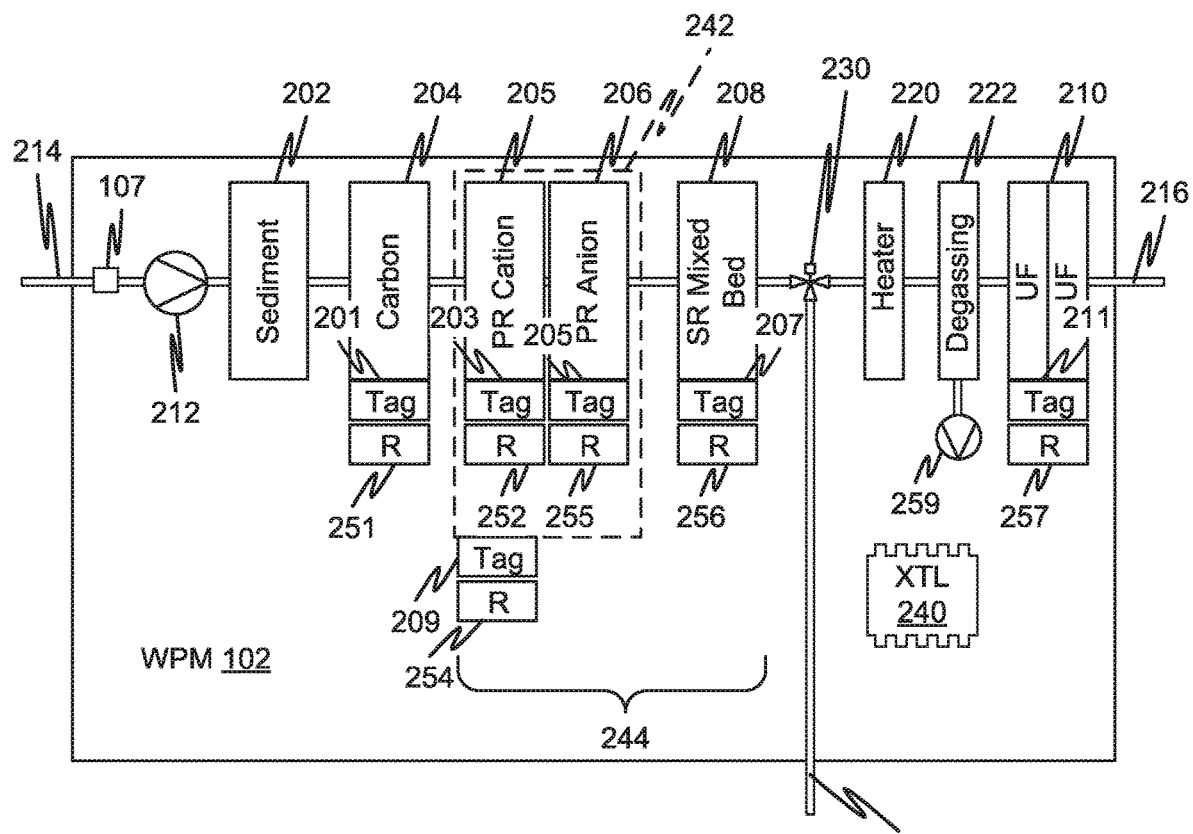
FIG. 4 shows a variant of the water purification module of the embodiment of FIG. 2 in which respective data carrier readers 251, 252, 254, 255, 256, and 257 are provided, according to embodiments of the disclosure subject matter.

FIG. 4 shows a variant of the water purification module of the embodiment of FIG. 2 in which respective data carrier readers 251, 252, 254, 255, 256, and 257 are provided. The readers 251, 252, 254, 255, 256, and 257 may be positioned with respect to a housing of the water purification module 102 so that each receiving bay can automatically read a respective data carrier. Note that this arrangement may be useful where the range of the reader 251, 252, 254, 255, 256, and 257 is very restricted, for example, a bar code laser scanner or conductive contact device for reading a smart chip is employed.

Figure 5:
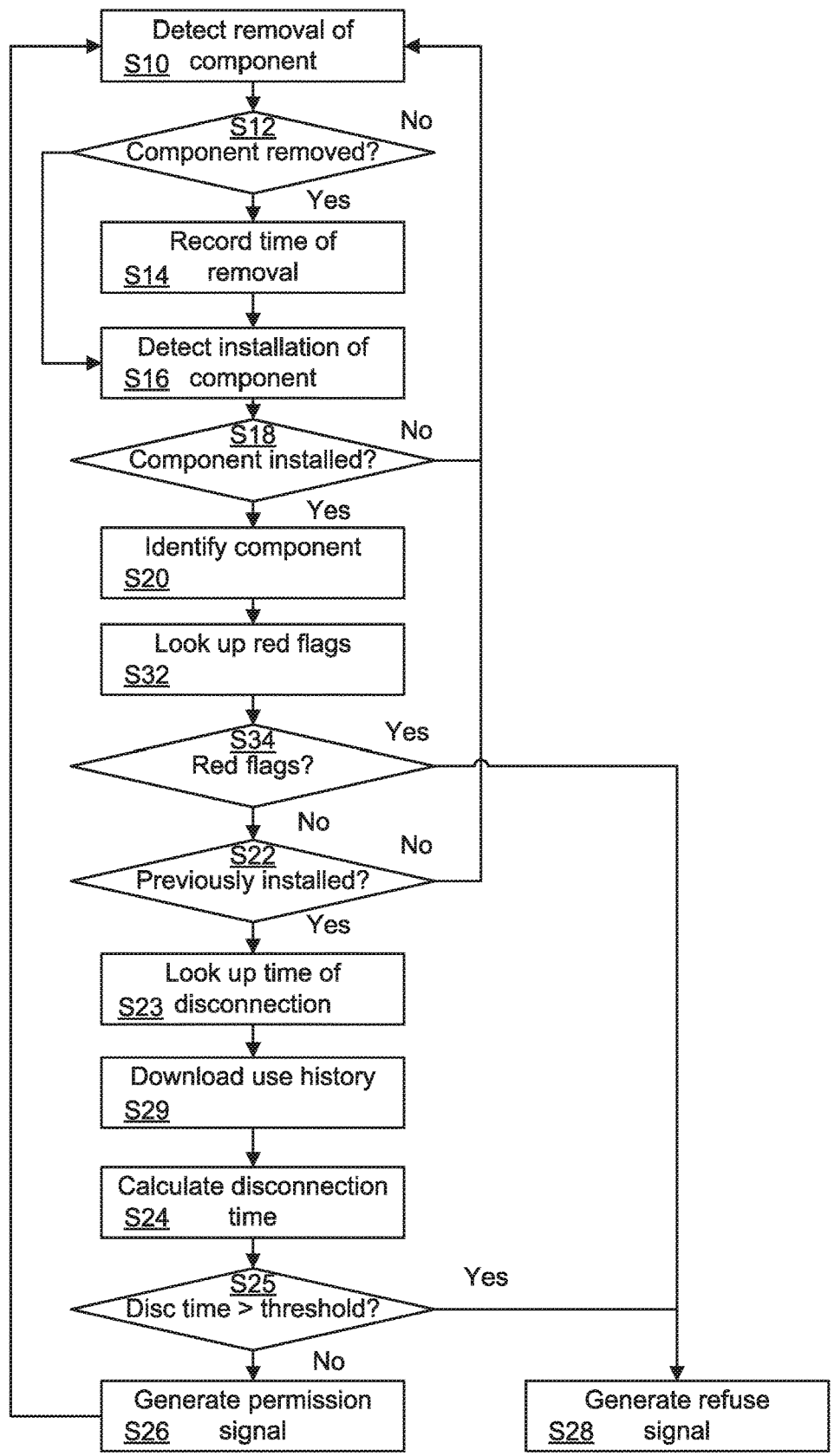
FIG. 5 shows a flow chart representing a method for permitting or refusing the use of a replaceable tagged component in a device utilizing the same, according to embodiments of the disclosure subject matter.

The information stored on data carriers (as in any of the embodiments) may allow the controller 240 to verify that the correct type of replaceable tagged component 272 is installed. The controller 240 may detect the removal or disconnection of a replaceable tagged component 272 as well. In an embodiment, the controller 240 may generate a refuse signal and take corrective action (such as preventing use of the water purification module 102 or blocking installation of the replaceable tagged component 272 or some other action). Referring now to FIG. 5, in a method implemented by the controller 240 (or by controllers of any of the embodiments employing replaceable tagged components), the removal of a replaceable tagged component 272 is detected (S10). The removal may be detected by the fluid line disconnection of the replaceable tagged component 272, by the movement of the replaceable tagged component 272 to a remote location, or by the displacement of the replaceable tagged component 272 relative to a reader such as a bar code scanner or RFID reader. At S12, if the replaceable tagged component 272 is determined to have been removed S14, a time of removal is recorded in a data storage accessible to the controller 240 (S14) and if not, control passes to S16. At S14, a unique identifier of the replaceable tagged component 272 may be recorded along with the time of removal.

In alternative embodiments, a data carrier on the replaceable tagged component 272 may be updated to include an indicator that the replaceable tagged component 272 was disconnected and the time of disconnection. At S16, the controller 240 detects the installation of a replaceable tagged component 272 and if one has been installed, it is identified at S20 (or in alternative embodiments, the attached data carrier is read to determine the time of disconnection). At S20, the component is identified and if at S22 it was previously installed, the time of disconnection is determined at S22 by reading data from the data store corresponding to the identity of the replaceable tagged component 272. The length of the disconnected interval of the replaceable tagged component 272 is determined at S24 and if it exceeds a predefined threshold stored by the controller 240, a refusal signal is generated at S28; otherwise a permission signal is generated at S26. In response to the permission or refuse signal, the controller may prevent use of the installed replaceable tagged component 272 by any of the mechanisms described herein. At S34, the controller 240 may identify any other types of red flags. For example, it may determine if the replaceable tagged component 272 has been expired or otherwise indicated at unsuitable for use and if so, at S34, a refuse signal may be generated at S28.

At S32, in embodiments, the controller 240 may determine from the data carrier attached to the replaceable tagged component 272 whether the latter has been previously used, for example, on a different system or the same system. It may further permit or allow reuse based on criteria, such as whether the system (e.g., water purification module 102) was a known system, for example, one that is used in a particular treatment facility and therefore a home system subject to identical use protocols, or an alien or unknown system. The data carrier attached to the replaceable tagged component 272 may also store use history information such as date of first use, number of water purification modules 102 it has been installed on, time since last use, etc. The controller may be programmed to permit or refuse based on an algorithm applied to these input data.

An operation S29 may be included in which the controller 240 downloads data indicating the use history of the replaceable tagged component 272 and calculates whether it is permissible to be used according to some predetermined formula. The use history may contain volume of fluid processed, time remaining before an expiration date, and/or other data indicative of wear and tear on a replaceable tagged component 272. A time at which a replaceable tagged component 272 was disconnected or first wetted may be determined by looking up data stored locally or on an Internet-accessible data service (S23). These data may be used to permit or prevent the use of a replaceable tagged component 272.

The controller 240 may further be programmed to determine if the replaceable tagged component 272 that is being connected is a correct type of device for the water purification module 102 (or other type of system using the replaceable tagged component 272). To this end, the data carrier attached to the replaceable tagged component 272 may store a product class that identifies the type of device. A scanner local to the receiving bay (as in FIG. 4 embodiment) may scan the data carrier and determine, based on the particular receiving bay on which it is installed, whether the correct type of replaceable tagged component 272 is being loaded.

In embodiments, replaceable tagged components 272 have fluid connectors with leads. In FIGS. 6A-6C, a replaceable tagged component 272 is shown at 302. The replaceable tagged component 302 has a fluid connector 306 with electrically conductive connector portion 330 that permits a data carrier 316 to communicate, when connected, with the controller 240 of the water purification module 102. The controller connects through a conductive contact 328 on a connector 308 of the water purification module 102 embodiment indicated at 270 supported by a fluid circuit support 312. The water purification module 270 has a support 304 to receive the replaceable tagged component 302. When the replaceable tagged component 302 is positioned in its support 304, the connectors 306 and 308 can be connected fluidly and, simultaneously, electrically so that the replaceable tagged component 302 is connected fluidly to the water treatment module 270 and the data carrier 316 is connected electrically to the controller 240. As indicated at 334, conductive wiring can be attached along a fluid line 318. The electrical connector portions 328 and 330 may connect multiple conductors for transfer of signals as well supplying power. In alternative embodiments, the data carrier 316 may include an RFID or smart chip that communicates wirelessly with the controller 240, in this case fitted with a transceiver or receiver. Other alternative embodiments may employ bar code readers.

Data carriers of the above and below embodiments in which replaceable tagged component 272 are used may include the following data to support functionality described herein.

The type of replaceable tagged component 272 correct canister is loaded into the hardware identified by a unique class identifier, which may also include model number, date of manufacture or lot number, and identifier of manufacturer.

A unique identifier of the replaceable tagged component 272 such as a serial number.

Disposable status including, for example, expired, exhausted, new, and used.

Allowed uses for the replaceable tagged component.

A log of error conditions encountered by the replaceable tagged component 272. The list may be generated by the water purification module 102 or other machine into which the replaceable tagged component 272 has historically been installed.

A list of requirements for use of the replaceable tagged component 272, such as upstream fluid conditions or pressure limitations.

A list of prior users and/or devices each uniquely identified by a code.

A complaint-report identifier that can be matched against a log of complaints for similar replaceable tagged components 272 and others.

A log of conditions that may indicate risk of failure such as surpassed pressure limits, temperature limits, usage cycles, and incomplete fluid processing cycles.

Figure 7:
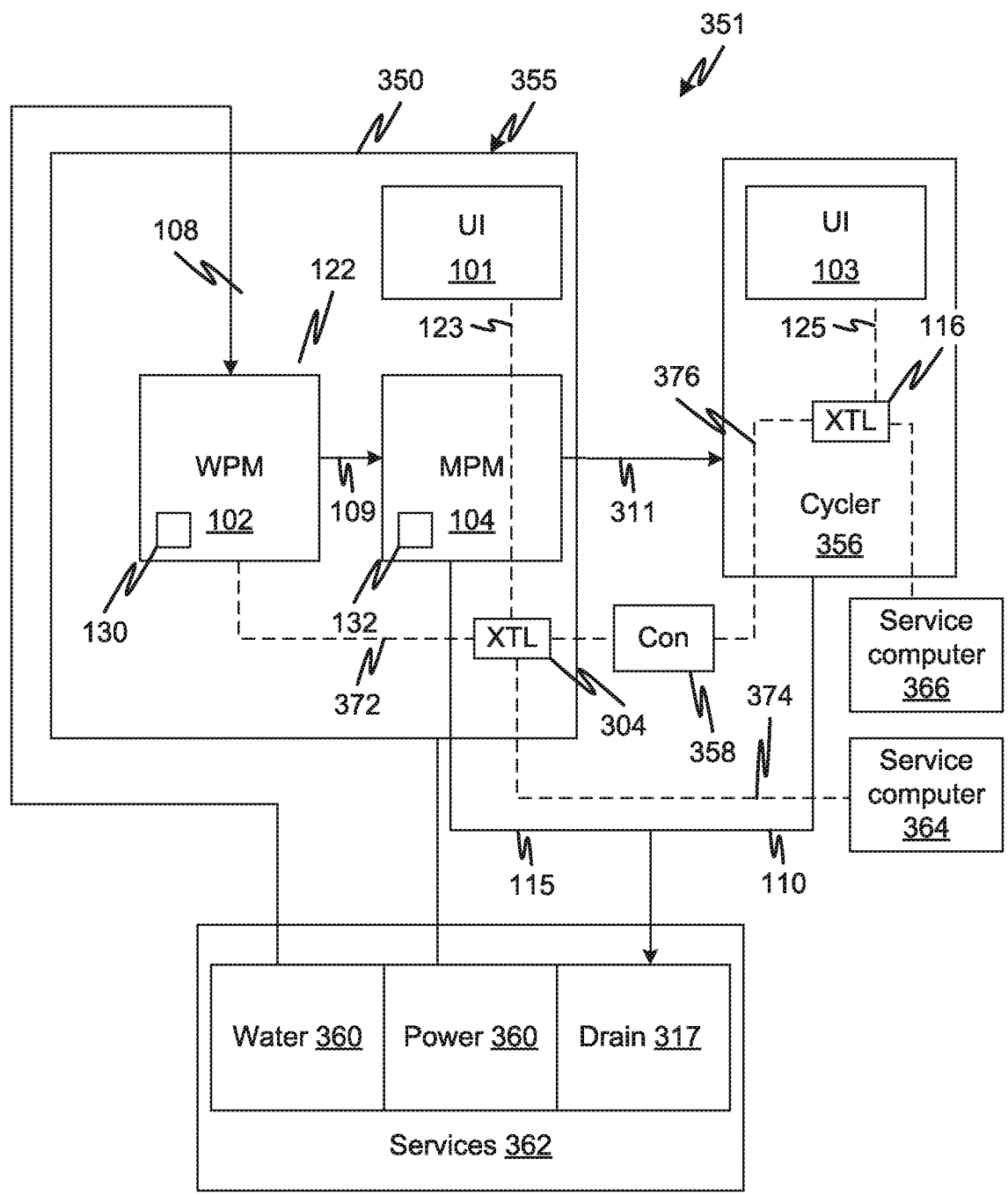
FIG. 7 shows an overview of an online water purification, proportioning medicament generation, and treatment system, according to embodiments of the disclosed subject matter.

FIG. 7 shows an overview of an online water purification, proportioning medicament generation, and treatment system 351. The water purification module 102 and medicament proportioning module 104 form a medicament generation system 355 and are commonly housed in a housing 350 with a user interface 101. The cycler 356 (or generally, a medical treatment device that consumes medicament generated by the medicament generation system 355) may form a separately housed device that is signally and fluid connected to the medicament generation system 355. Communications module 358 interconnects the controllers 304 and 116 of the medicament generation system 355 and cycler 356 respectively.

By combining the medicament generation system 355 with a cycler, a system suitable for use in a home, critical care, or clinic may be provided without a need for specialized services such as high capacity municipal water supply, power, or drainage. For example, high volume water supply is typically required in reverse osmosis-based water purification system. In the present embodiments, municipal water 360 is deionized using consumable deionization filter beds, allowing normal rates of water flow and drainage 317 in a services supply 362 that is typical of a home or the room services of a hospital. With power 360 requirements at residential or typical hospital-room voltages and currents, available services allow the proportioning medicament generation, and treatment system 351 to be used for home and critical care, as well as in clinics. For clinics, the rapid set-up of a new installation can be facilitated as well because expensive capital infrastructure of an online medicament generation system can be avoided.

As in the embodiment of FIG. 1, the water purification module 102 receives tap water 108 from a municipal water supply. The water purification module 102 purifies the water and checks its purity under control of controller 304. The water purification module 102 utilizes one or more filter modules 130 which are replaced to help maintain its ability to generate product water that is sterile and ultra-pure. Product water 109 from the water purification module 102 is conveyed to a medicament proportioning module 104 which mixes concentrates provided in a replaceable fluid circuit 132 in a predefined proportion to generate a medicament 311. The water purification and medicament generation are performed in on-line fashion and on-demand, which means water is purified and mixed with medicament concentrate as a continuous process, at a rate of consumption and as demanded by a final consumer, in this case, a cycler 356. Waste produced by the medicament proportioning module 104 is conveyed as indicated at 115 to a drain 317. Waste 110, for example spent medicament, is conveyed to the same drain or another drain 317. The cycler 356 may be of any type including hemodialysis and peritoneal dialysis as well as other types of treatment systems.

The function of the communication module may allow the controller 116 to send specific command signals to the medicament generation system 355, for example, to start and stop medicament generation. In a system in which the cycler 356 is not adapted to send specific commands, a status vector can be translated by the communications module 358 to convert it to one or more suitable commands. A status vector may include information such as whether a blood pump of the cycler 356 is running.

Service computer 364 and 366 may communicate, respectively, with the medicament generation system 355 and cycler 356. The controllers 304 and 116 may generate operation or treatment logs and/or maintenance information which they may send the service computer 366 for further distillation, synthesis, storage, or communication to other facilities and/or remote professional care management or maintenance personnel.

Figure 8A:
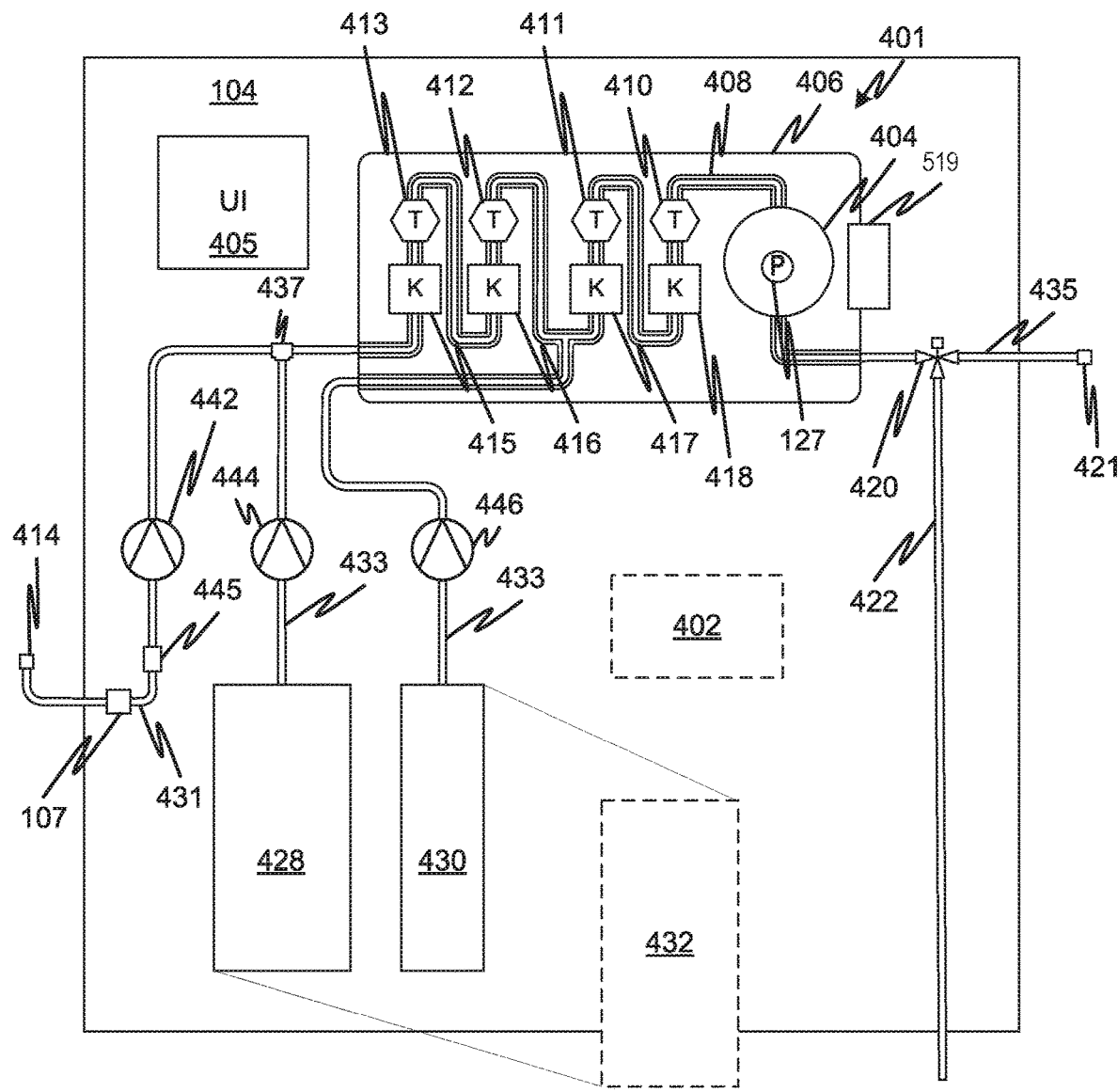
FIG. 8A shows details of an embodiment of medicament proportioning module, according to embodiments of the disclosed subject matter.

FIG. 8A shows details of an embodiment of medicament proportioning module 104. A sealed fluid circuit 401 is partially supported by a cartridge support 406. Flow lines supported by the cartridge support 406, shown generally at 408 may be tubes attached to the cartridge support 406 or formed therein by molded and sealed channels or in attached seam-welded flexible panels or by other suitable means. The sealed fluid circuit 401 may also include all the other lines and fluid circuit elements illustrated including such as waste line 422, inlet line 431, medicament concentrate lines 433, product medicament line 435, control valve 420, junction 437, and inlet sterile filter 445 to form a single pre-connected sterile disposable unit along with the flow lines 408 (and other elements supported by the cartridge support 406 described below). As explained, the entire sealed fluid circuit 401 shown in FIG. 8A, save for the inlet line 431 inlet and product medicament line 435 are pre-connected and sealed from the external environment. The sealed fluid circuit 401 may be sterilized as a unit, for example, gamma sterilized or heat sterilized.

A source of pure water can be connected by way of a connector 414 which is capped and sterile-sealed prior to connection. By sterile-sealed it is meant that a seal is formed sufficient to physically block any contaminants from entering. A sterile filter 445 insures that any contamination in the flow, for example resulting from touch contamination or a contaminated connector on the pure water source is trapped by the sterile filter 445. Thus, sterile filter 445 forms part of the complete sterile barrier such that the entire sealed fluid circuit 401 has a continuous sterile barrier even after the connector 414 is unsealed, at least while the product medicament line 435 connector 421 is capped. The sterile filter may be one with a 0.2 μm membrane to block bacterial contaminants. Note that by ensuring completely sterile deionized water flows into inlet line 431 and because the entire sealed fluid circuit 401 is sealed and sterile, the unit once set up and ready for treatment can be filled and used over an extended treatment without the risk of proliferation of contaminants. For example, the sealed fluid circuit 401 can be prepared for use and primed and used, up to 24 hours later. Alternatively it may be used for more than one treatment.

Pure water flows through the sterile filter 445 at a rate of pumping determined by the pump 442. Sterile water also may be drawn through the product water inlet 431 and the filter 445, via the junction 419, by medicament concentrate pump 444 to generate the saturated medicament concentrate container 429 through a water branch line 451. To match the rate of production of purified water with the rate of pumping by pump 442, the source of purified water may generate a constant supply into an accumulator, it may pump continuously with overflow to a drain, or a pump of the water purification module 102 may be commanded in response to the controller 402 of the medicament proportioning module 104. A control valve 449, which may be a pinch clamp or any other type of control valve, may be controlled to prevent a reverse flow of water from the dry medicament cartridge 447. In alternative embodiments, a check valve may be used in place of control valve 449. Reference numerals in FIG. 8B not otherwise discussed are as shown and discussed with reference to FIG. 8A where they identify the same elements in FIG. 8B. Reference numeral 432 indicates that a single concentrate, such as lactate buffered dialysate, can be substituted for the multiple-component concentrate. This is true of any of the embodiments.

Figure 8B:
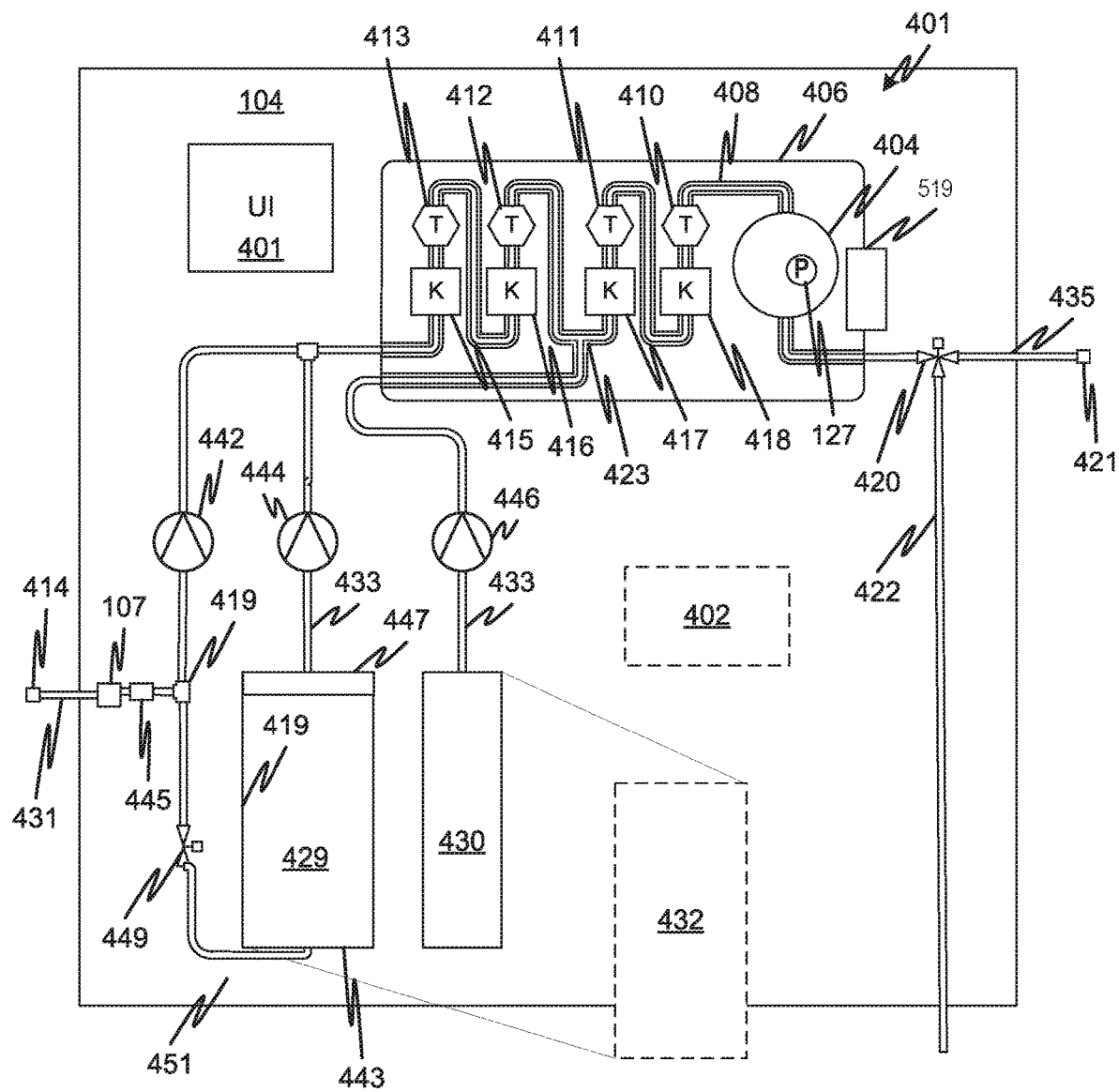
FIG. 8B shows details of an embodiment of medicament proportioning module, according to other embodiments of the disclosed subject matter.
Figure 8C:
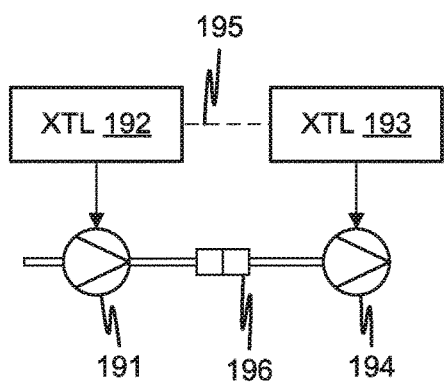
FIGS. 8C through 8H and FIG. 8J show mechanisms for interfacing the flow of fluid between a water purification module and a medicament proportioning module, according to embodiments of the disclosed subject matter.
Figure 8D:
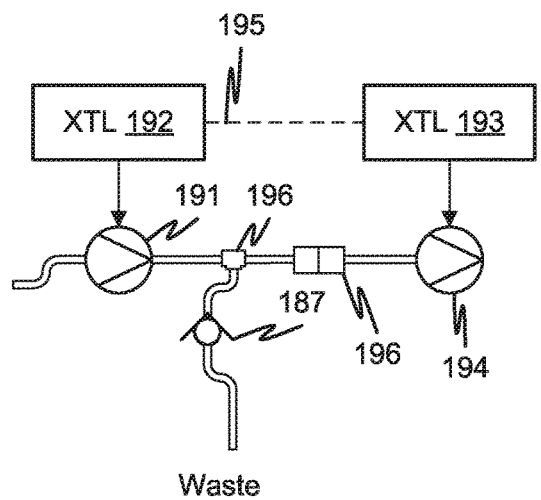
Figure 8E:
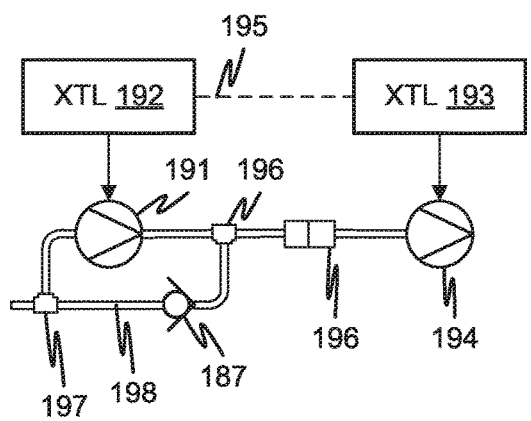

Referring to FIG. 8C, for example, a pump 191 may be a positive displacement pump that is controlled as a slave by a controller 193 of a medicament proportioning module. Pure water flows through the connection 196 on-demand. A controller 192 of the water purification module may control the pump 191 directly to ensure that water flows at a rate at which it is commanded by the controller 193. Alternatively a single controller 193 can control pump 191. The pump 194 belongs to the medicament proportioning module and is used for regulating the flow of water for the dilution of water concentrate to generate medicament. In this and any of the other embodiments of FIGS. 8C through 8G, the single pump 191 can regulate the flow of water through the medicament proportioning module, avoiding the need for a separate pump 194 or 191. Referring to FIG. 8D, water purification module pump 191 is controlled by controller 192 and maintains a pressure in the junction 196 determined by a cracking pressure of a check valve 187. The pump 191 may be controlled as discussed in the previous embodiment, with the arrangement here providing a compliance that may not be present in the previous embodiments because any overshoot of the pump 191 can be accommodated by overflow through the check valve 187. Referring to FIG. 8E, a similar arrangement as that of FIG. 8D recirculates any overflow water back through the pump 191 through a recirculating line 198. This also maintains a predefined pressure at the junction 196 and allows the pump 191 to run without wasting water. Note that it may be possible to place the pumping arrangements at any point in the water purification module flow path so that unpurified water, partially purified water, or purified water is pumped by pump 191.

Figure 8F:
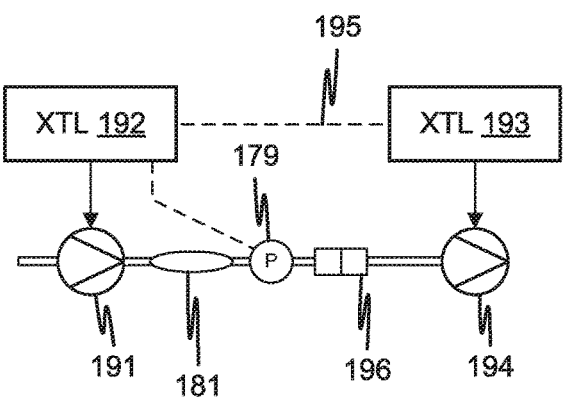

FIG. 8F shows an arrangement that is similar to that of FIG. 8C, except that in the embodiment of FIG. 8F, compliance may be provided by an accumulator 181 and pressure may be monitored by way of a pressure transducer 179 in the connection 196 fluid channel. The pressure sensor can be located upstream or downstream of the accumulator 181. The controller 192 may detect a current pressure and regulate the pump 191 to maintain a range of pressures that accommodates a mismatch between the rates of pumps 191 and 194 or a delay in the regulation of one or both of the pumps 191 and 194 responsively to commands from the controller 193. As the pump 194 draws down the volume of the accumulator 181, the pressure falls therein, which is detected by the pressure transducer 179. The pressure signal is applied to the controller 193. In response to the fall in pressure, the controller 192 causes the pump 191 to pump to try to restore the target pressure in the accumulator 181. Thus, the operation of the pump 194 may indirectly control the operation of pump 191 as a pressure signal through the accumulator 181. The accumulator 181 may be of the configuration discussed with reference to FIGS. 8H and 8J. The pump 191 may be one or more pumps that are controlled to proportion water and medicament concentrate. Where pressure of the accumulator is used to control pumping of pump 191, there is no need for a signal line 195 or direct signal control of pump 191 by controller 193.

Figure 8G:
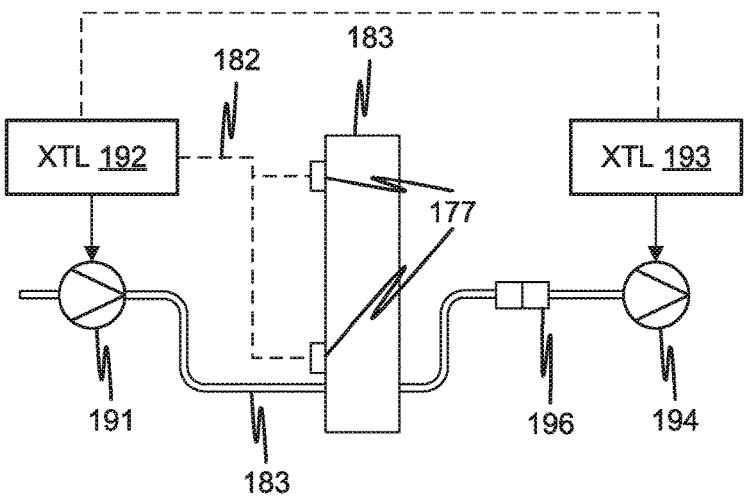

A variant of this arrangement is also shown in FIG. 8G in which an accumulator tank with one or more level indicators 177 that indicate a fluid level in the tank 183. Controller 192 may be regulated to maintain a predefined level or range of levels of the tank 183 such that as fluid is demanded by the pump 194, the demand can be immediately accommodated. Pump 191 is regulated by the controller 192 to fill the tank when the level is below a desired level and to stop when filled to a desired level. Alternatively the pump may be servo-controlled to maintain a fixed level only when a demand for water is received from the controller 193 by the controller 192. The mechanisms of FIGS. 8C through 8G may be adapted by incorporating them in a separate module between the water purification module 102 and medicament proportioning module 104 or in one or the of the water purification module 102 and medicament proportioning module 104 to form further embodiments.

The interfaces of FIGS. 8C through 8G may be used to interconnect a water purification module 102 with a medicament proportioning module 104. Alternatively, any of them may be used to interconnect a medicament proportioning module 104 with a cycler 106 or other consumer of medicament. These may be used to modify any of the disclosed embodiments.

Figure 8H:
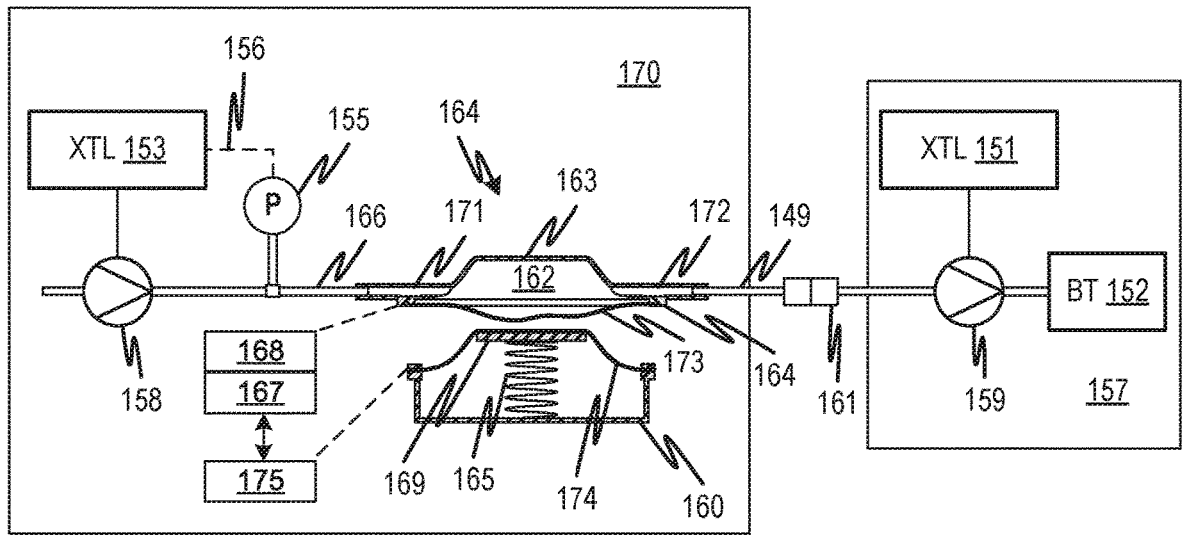

Referring now to FIG. 8H, medicament proportioning system 170 has a controller 153 that controls one or more pumps 158. The one or more pumps 158 conveys medicament through a product medicament supply line 149 which is connected (by connectors 161) to a downstream medicament consuming device 157 that draws product medicament using at least one pump 159. The medicament consuming device 157 may be an extracorporeal blood processing system (with a blood treatment component 152) such as a dialysis system or any of the other medicament consuming devices mentioned in the instant disclosure. In many medicament consuming device 157 the demand for medicament may be intermittent, irregular, or otherwise variable. For example, the medicament consuming device 157 may draw fluid in a bolus with a brief pause or it may have a flow profile that periodically and progressively peaks and troughs between maximum and minimum values. However, for various reasons, it may be desired to operate the one or more pumps 158 at a more constant or slowly-varying rate. The reasons may include a need or desire for more accurate proportioning of water and medicament concentrate in in-line medicament proportioning systems such as medicament proportioning system 170. For example, in some hemodialysis systems, the medicament is drawn by a fluid balancing component that draws medicament in steps. Examples include known volumetric fluid balancing components of hemodialysis system systems used for balancing the flow of fresh dialysate against spent dialysate throughout a treatment. A fluid circuit 168 has an accumulator 164 integrated therein. The accumulator 164 may be attached to, or integrated in, a cartridge indicated figuratively at 168, for example as in many of the embodiments described in the present disclosure. The medicament proportioning system 170 fluid circuit 168 or other fluid circuit may have sensors and actuator portions 167 that engage with and sensors and actuators 175 of the medicament proportioning system 170.

The accumulator 164 includes a flow chamber housing 163 with an internal volume 162. Product medicament flows through the internal volume 162. Product medicament may flow into an inlet 171 and out from an outlet 172 defining a continuous flow path through the internal volume 162. The interior volume 162 is sealed by a chamber-wall film 173 which may be of the same type as provided for sealing the trough-shaped channels of fluid circuit cartridge embodiments described herein and in the claims. Thus, the chamber-wall film 173 may be adhered by welding or adhesive or any other suitable method to a perimeter region 164 of the flow chamber housing 163. To make the chamber-wall film 173 larger in area, following the attachment of the chamber-wall film, it may be stretched by heating and forcing a boss (not shown) into the chamber-wall film 173, which may be shaped as the interior volume 162 or any other shape or size suitable for stretching the chamber-wall film 173. Note that the chamber-wall film 173 may be made of highly elastic material and may not need to be stretched at all. In embodiments, the trough-shaped channels (see discussion and examples throughout the specification) are sealed with the same type of film used for the chamber-wall film 173.

Figure 8J:
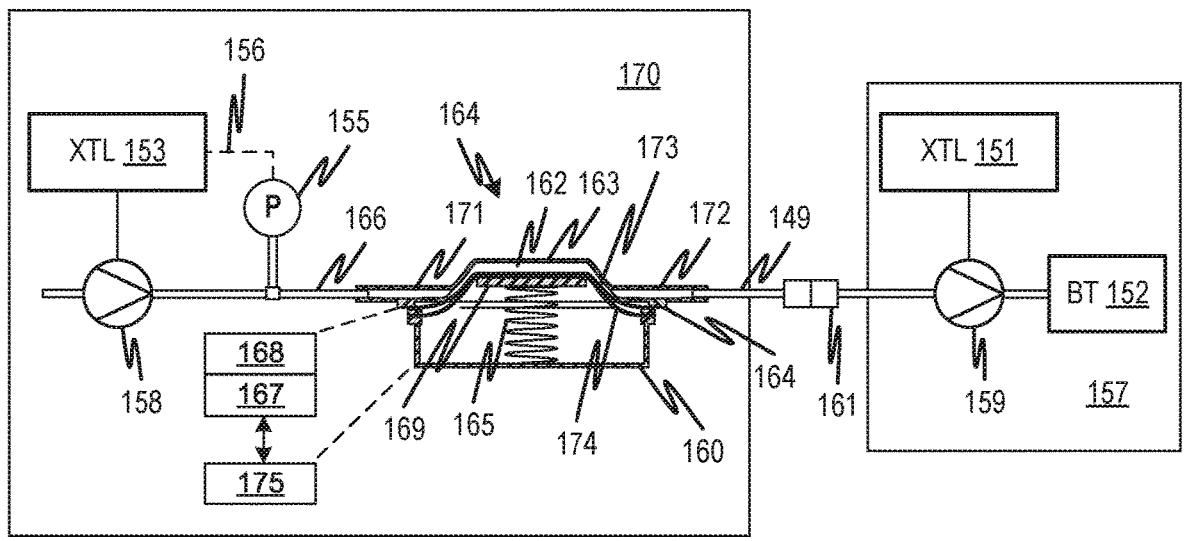

The accumulator 164 chamber-wall film 173 engages a forcing module 160 during use. In FIG. 8H the forcing module 160 is shown relatively retracted from the accumulator 164. FIG. 8J shows the forcing module 160 positioned against the accumulator 164 as it would be during operation. The forcing module 160 has an elastic web 174 supported by a button 169 which is urged by an urging element 165 such as a spring. The button 169 floats (i.e., it is unsupported by a bearing or slide) so that there is no frictional loss due to sliding or rolling supports so as to minimize any hysteresis or frictional component to pressure generated in the interior volume 162. In use, the interior volume 162 pressure is determined by the constant of urging element, for example by the spring constant. Thus a progressive change of pressure with volume may be provided which is repeatable and does not depend on variation due to manufacturing tolerances of the accumulator 164 or fluid circuit (e.g. cartridge) 168 of which it is a part. The elastic web 174 may be of neoprene or elastomer, or some other suitable material. During operation, the urging element 165 would expand and contract as the interior volume 162 changes. Note that in embodiments, it may be desirable for the button to be a larger fraction of the facing area of the interior volume 162 to minimize the contribution of the elastic properties of the elastic web 174 and chamber-wall film 173 to the volume-versus-pressure properties of the interior volume 162.

A pressure transducer 155 receives pressure signals from the product medicament channel 166 and conveys them to controller 153 of the medicament proportioning system 170. The pressure transducer 155 may be connected to the accumulator directly in alternative embodiments. In embodiments discussed relative to FIG. 17, the pressure transducer may be a strain gauge that is forced against a fluid channel formed in a base element of a cartridge and closed by a film, the film pushing on the strain gauge to generate the pressure signal (See discussion of FIG. 17, reference numerals 847, 848 and channels 826 and methods of forming.) Note that controllers 153 and 151 may be distributed among components in any suitable fashion and the medicament proportioning system 170 and the medicament consuming device 157 may be combined and/or controlled by a single controller in alternative embodiments. As the medicament consuming device 157 demands fluid by pumping from the interior volume 162 by causing a reduced pressure by means of the at least one pump 159, the change in pressure causes a reduction in volume of the interior volume 162 and the pressure change is indicated to the controller 153 by the pressure transducer 155. The controller 153 may have a servo program or proportion, integral, differential control device or any other suitable device for causing the one or more pumps 158 to operation continuously to maintain a predefined minimum volume of product medicament in the interior volume 162. For example, it may use an integral-dominated algorithm to smooth the changes in pressure and control by an average pressure in the interior volume 162 toward a constant pump speed or a slowly varying pump speed.

The size of the accumulator 164 internal volume 162 may be selected based on the variability of the demand in order to minimize the accumulator internal volume 162. The selected volume may be selected based on a survey of all the operating conditions of the medicament consuming device 157, internal compliance of all connected fluid channels between the accumulator 164 and the medicament consuming device 157 as well as the characteristics of the pressure transducer and the feedback control algorithm used to regulate the steady pumping rate 158 of the medicament proportioning system 170 (i.e. one or more pumps 158). Note that the one or more pumps 158 may include a water pump and one or more medicament pumps which together determine the flow rate into the product medicament channel 166. In embodiments, the size of the internal volume is a minimum volume required to allow the one or more pumps 158 to be operated at a constant speed (i.e., all of the contributing pumps of one or more pumps 158 may operate at constant speeds) at all operating conditions of the medicament consuming device 157. Note that by "constant speed" it should be understood that this refers to the average rate which may vary but on a time scale that is less than the time scale of periodic variability of the medicament consuming device 157. So over, for example, the average rate of flow of medicament through medicament consuming device 157 may be constant during a one minute period early during a treatment and may be lower or higher during a one minute period later or earlier in the same treatment, but during each minute, there may be periodic fluctuations in flow rate that are accommodated by the accumulator 164. A first characteristic of the variability that drives the selection of characteristics the accumulator 164 is that the variability is of a much shorter time scale that the time scale of a treatment, for example, a hundredth or a thousandth of the time scale of the treatment. Another is that it is periodic (goes up and down and back up again, cyclically and predictably). Another characteristic is that the variability is due to a mechanical characteristic of a pumping mechanism of the medicament consuming device 157.

The embodiment of FIG. 8H, 8J, which may be incorporated in any of the disclosed embodiments or combined with features of the claims to form new embodiments. The embodiment may be a feature of a medicament supply system, a medicament proportioning module 104 of a system that includes or doesn't include a plant for purification of water. It will be observed that this embodiment provides a forcing module 160 that ensures a progressive change in pressure with volume and preferably one that approximates the linearity of the urging element 165, for example a spring constant. The forcing module applies a force from a passive component (spring) whose shape is changed in response to changes in pressure which change of shape results in a predictable, repeatable, volume-versus-pressure characteristic of the interior volume 162. A feature of the forcing module is that no bearing surfaces are required to be engaged. These features can help to make the pressure-volume response linear. In alternative embodiments, the pressure-volume relationship may be other smoothly varying progressive functions that permit a flow rate upstream to be constant, or smoothly varying so as to permit accurate proportioning of missed component fluids as described. The use of an elastic wall 173 and an elastic web 174 can avoid the need for a bearing, but the elastic changes (e.g., stretching) and shape changes can affect the pressure-versus-volume characteristics of the interior volume 162. This may introduce material or variation due to manufacturing tolerances that may affect regulation of the pump speed. The use of the button 169 and urging element 165 and the selection of a web 174 and elastic wall 173 material and dimensions to minimize their contribution to the restoring force ensure that the pressure-volume characteristic of the interior volume 162 is predictable. In embodiments, the pressure-volume state diagram of the interior volume 162 is linear and exhibits essentially no hysteresis. In embodiments, the interior volume 162 (or the displaced volume over the full range of travel of the elastic wall 173) is selected to be a predetermined ratio above the minimum required to allow for constant (again, constant within the lower time scale) flow rates of controller 153 based on a predefined medicament consuming device 157, compliance of connected channels, and a predefined algorithm, sensor response, and other characteristics of the regulated system. The predefined ratio may be less than 2, effectively specifying that the displaced volume no more than twice the minimum necessary to provide for constant rates of pumping by the one or more pumps 158. A common example of a medicament consuming device 157 having variable rates of pumping is a volumetric balancing system that alternately fills and drains one or more chambers to achieve an average-balanced flow rate. Note that the embodiment of FIGS. 8H and 8J may be used in combination with any of the embodiments disclosed herein. It will be noted that by controlling the one or more pumps 158 responsively to a pressure of the transducer 155, effectively a mechanical command signal may be transmitted by the medicament consuming device 157 pump at least one pump 159. That is, as the medicament consuming device 157 pump at least one pump 159 draws down the volume of the accumulator 164, the servo-control of the one or more pumps 158 responds through the pressure signal of transducer 155 to maintain the average volume of interior volume 162. Thus, in embodiments, the medicament proportioning system 170 and medicament consuming device 157 may be mechanically coupled without providing a control interface to regulate flow.

In alternative embodiments, the volume of 162 is actively controlled by an active actuator in place of urging element 165 in response to changes in a detected volume. For example, a displacement encoder could be connected to a linear motor used in place of urging element 165. In such an embodiment, volume feedback control may be used to maintain an average target volume in the internal volume 162.

Referring again to FIG. 8A, the cartridge support 406 may be received in a medicament proportioning module 104 which may further be stand-alone unit or combined with a water purification module 102. As illustrated, the medicament proportioning module 104 is a stand-alone unit. Purified water is received at an inlet 431, which forms a part of a disposable sterile fluid circuit that includes all the fluid lines and circuit components illustrated in the figure and/or discussed herein. Pump 442 pumps water that flows at a rate controlled by a controller 402. Pumps 44 and 446 regulate flows of respective medicaments concentrates in medicament concentrate lines 433 so that they are diluted in a precisely controlled ratio by the flow of water pumped by the pump 442. A first concentrate in container 428 pumped by pump 444 is combined in junction 437 with the flow of water pumped by pump 442, thereafter flowing into a conductivity measurement module 415 which generates a signal indicative of the concentration of medicament concentrate in the mixture emerging from the junction 437. A temperature signal indicating a temperature of the same flow is also generated by a temperature transducer 413. The signals indicating conductivity and temperature are applied to the controller 402 which converts them to concentration responsively to stored (in a data store of the controller—not shown separately) conductivity-temperature curves for the solution of the diluted first concentrate stored in the container 428. A secondary set of conductivity measurement module and temperature transducer 416 and 412 may be provided to provide signals indicating conductivity and temperature of the same flow as a confirmation. If the calculated concentrations differ, the controller 402 may generate a signal indicating a corresponding error condition. In response the controller 402 may generate an error indication on a user interface 405 or halt the flow of medicament, or divert it through a diverting valve 420 to a waste line 422, for example.

The second medicament concentrate is pumped by pump 446 from container 430 into a junction 423 so that the second concentrate is mixed with the diluted first concentrate. The diluted and mixed first and second concentrates flow into a conductivity measurement module 417 which generates a signal indicative of the concentration of medicament concentrate in the mixture emerging from the junction 423. A temperature signal indicating a temperature of the same flow is also generated by a temperature transducer 411. The signals indicating conductivity and temperature are applied to the controller 402 which converts them to concentration responsively to stored (in a data store of the controller—not shown separately) conductivity-temperature curves for the solution of the diluted first and second concentrates. A secondary set of conductivity measurement module and temperature transducer 418 and 410 may be provided to provide signals indicating conductivity and temperature of the same flow as a confirmation. If the calculated concentrations differ, the controller 402 may generate a signal indicating a corresponding error condition. A final medicament product concentration flows through the line indicated at 408 into an accumulator 404 which has an expandable volume whose pressure may be substantially determined by a spring constant due to a spring-based restoring force (See discussion of details of an embodiment below and embodiment of FIGS. 8H and 8J). A connected device, such as cycler 106 can draw medicament through line 435. A cap 421 ensures a sterile output line and is removed before connection.

Referring now to FIG. 8B, an embodiment of medicament proportioning module 104 differs from that of FIG. 8B in that a concentrate of a component medicament is formed from a dry material by dissolving it either at once or progressively according to embodiments. In a preferred configuration, a bicarbonate buffer is stored in a cartridge 419 into which incoming purified water is diverted by a junction 419 such that it flows through a bed of dry bicarbonate to form a saturated concentrate in the outlet line 433 drawn by pump 444. A single concentrate component 432, such as lactate buffered dialysate concentrate, may be used for the generation of medicament as indicated to form further embodiments, in place of the multiple component embodiments discussed.

Figure 9A:
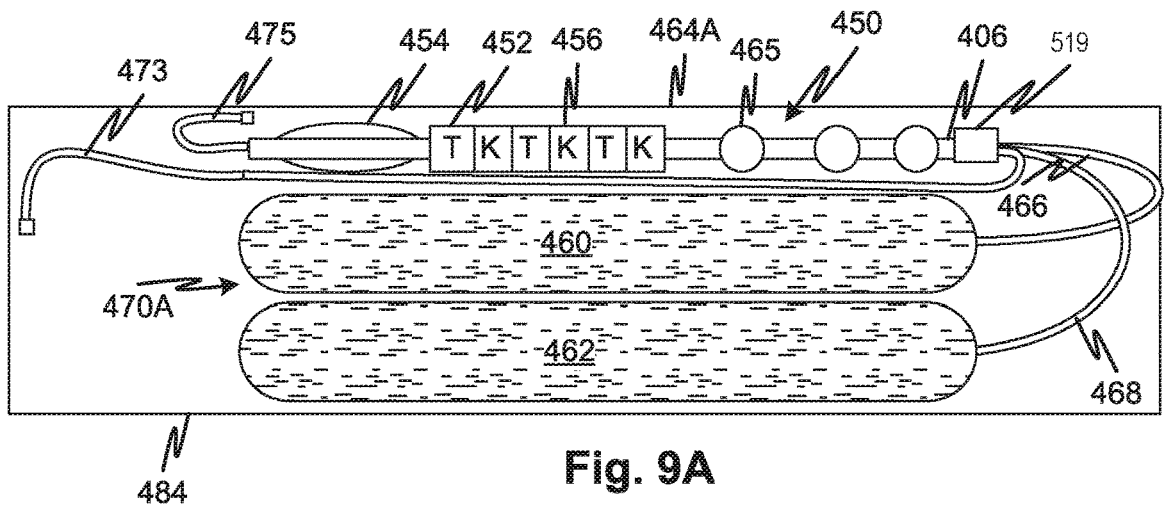
FIG. 9A shows a disposable including a fluid circuit cartridge and concentrate containers according to embodiments of the disclosed subject matter.

FIG. 9A shows a disposable 464A including a fluid circuit cartridge and concentrate containers according to embodiments of the disclosed subject matter. The concentrate containers 460 and 462 may correspond to containers 429 and 430 in the foregoing embodiments of FIGS. 8A and 8B. In the example of FIG. 9A, the concentrate containers contain liquid medicament concentrate. An example composition, which may include any number of concentrate components, is acid and a buffer such as bicarbonate or lactate. Bicarbonate may be provided in a dry form as illustrated in the further embodiments below. Peritoneal dialysate may have a third component such as glucose or preferably a mixture of electrolyte and glucose to allow concentration to be more easily calculate from a conductivity signal as discussed above. The concentrate containers 460 and 462 may be pre-connected with the rest of the sealed fluid circuit 470A including the cartridge 450. The concentrate containers 460 and 462 may be packaged with the rest of the sealed fluid circuit 470A including the cartridge as illustrated at 450. The concentrate containers 460 and 462 may be pre-connected with all inlet and outlet line 473, 475 connections sealed and capped. As described above, the cartridge 450 may have conductivity 456 and temperature 452 sensors, an accumulator 454 and other elements. The cartridge 450 may also have tube pumping segments 465 that are aligned with pump actuators (such as peristaltic pump rollers) when the cartridge 450 is positioned with respect to the medicament proportioning module 104. The fluid circuit 470A, including containers 460, 462 and cartridge 450 and any other components required to make up the disclosed embodiments may be packaged in a container 484 such as a box or bag.

In use, the cartridge may be removed from the container 484 and positioned in the medicament proportioning module 104. The containers 460 and 462 (and others if present, depending on the number of components) can remain in the container or box 484. Any flexible tubes remain interconnected such as tubes 466 and 468. The water inlet line 473 can be uncapped and attached to the water purification module 102 and the water outlet line 480 can be uncapped and attached to the inlet of the cycler 106. In this way, minimal handling of the individual components can result in the set of the medicament proportioning module 104. In embodiments, the cartridge 450 can be separately packaged, for example in a plastic bag, and attached to the outside of a box within which the containers 460 and 462 are held.

Figure 9B:
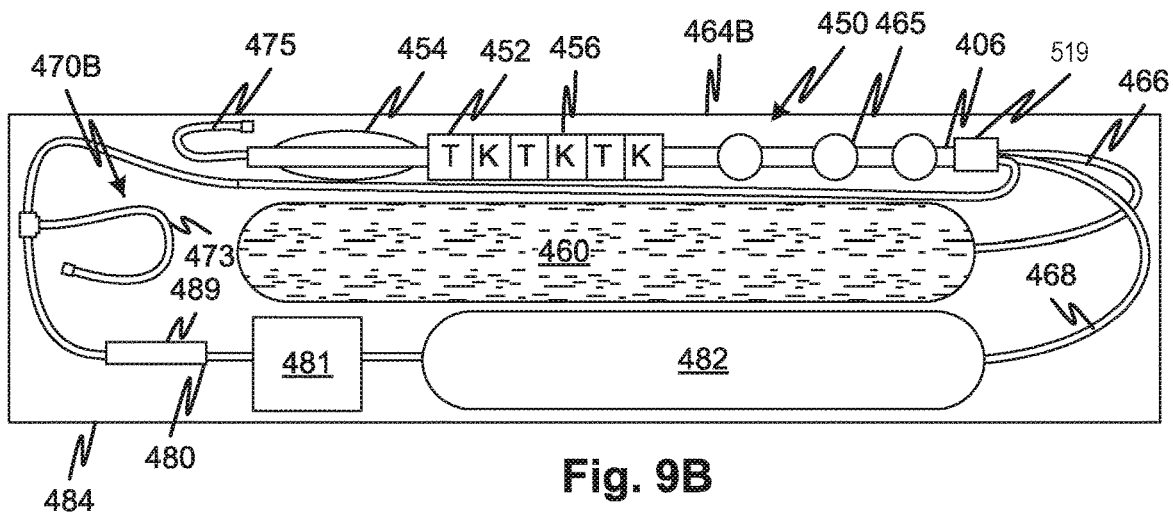
FIG. 9B shows a disposable including a fluid circuit cartridge and concentrate containers as well as a dry solute container according to embodiments of the disclosed subject matter.

FIG. 9B shows a disposable 464B including a fluid circuit cartridge and concentrate containers as well as a dry solute container according to embodiments of the disclosed subject matter. The concentrate container 460 contains a liquid concentrate. The container 482 is an empty container. A cartridge 481 contains a dry solute that is diluted with pure water which fills the container 482 to make a concentrate. The containers 460 and 482 may correspond to containers 429 and 430 in the foregoing embodiments of FIGS. 8A and 8B. The example constituents are otherwise as described with respect to FIG. 9A including the variations. The concentrate containers 460 and 482 and the cartridge 481 may be pre-connected with the rest of the sealed fluid circuit 470B including the cartridge 450. The concentrate containers 460 and 482 and the cartridge 481 may be packaged with the rest of the sealed fluid circuit 470B including the cartridge as illustrated at 450. The concentrate containers 460 and 482 may be pre-connected with all inlet and outlet line 473, 475 connections sealed and capped. As described above, the cartridge 450 may have conductivity 456 and temperature 452 sensors, an accumulator 454 and other elements. The cartridge 450 may also have tube pumping segments 465 that are aligned with pump actuators (such as peristaltic pump rollers) when the cartridge 450 is positioned with respect to the medicament proportioning module 104. The fluid circuit 470B, including containers 460, 462 and cartridge 450 and any other components required to make up the disclosed embodiments may be packaged in a container 484 such as a box or bag.

In use, the cartridge may be removed from the container 484 and positioned in the medicament proportioning module 104. The containers 460 and 482 and the cartridge 481 (and others if present, depending on the number of components) can remain in the container or box 484. Any flexible tubes remain interconnected such as tubes 466 and 468. The water inlet line 473 can be uncapped and attached to the water purification module 102 and the water outlet line 480 can be uncapped and attached to the inlet of the cycler 106. In this way, minimal handling of the individual components can result in the set of the medicament proportioning module 104. Water may flow into the line 480 through the cartridge 481 propelled by a pump that engages with a pumping segment 489 to prepare concentrate in container 482. In embodiments, the pumping segment 489 may be attached to the cartridge with other pumping segments as discussed with reference to FIG. 10, infra. In embodiments, instead of providing a separate cartridge, a dry solute may be stored in the container 482. In any of these embodiments, the contents of the container 482 may be mixed by continuous recirculating pumping using an additional branching line and pump (not shown). In embodiments, the cartridge 450 can be separately packaged, for example in a plastic bag, and attached to the outside of a box within which the containers 460 and 462 and cartridge 481 are held.

Figure 9C:
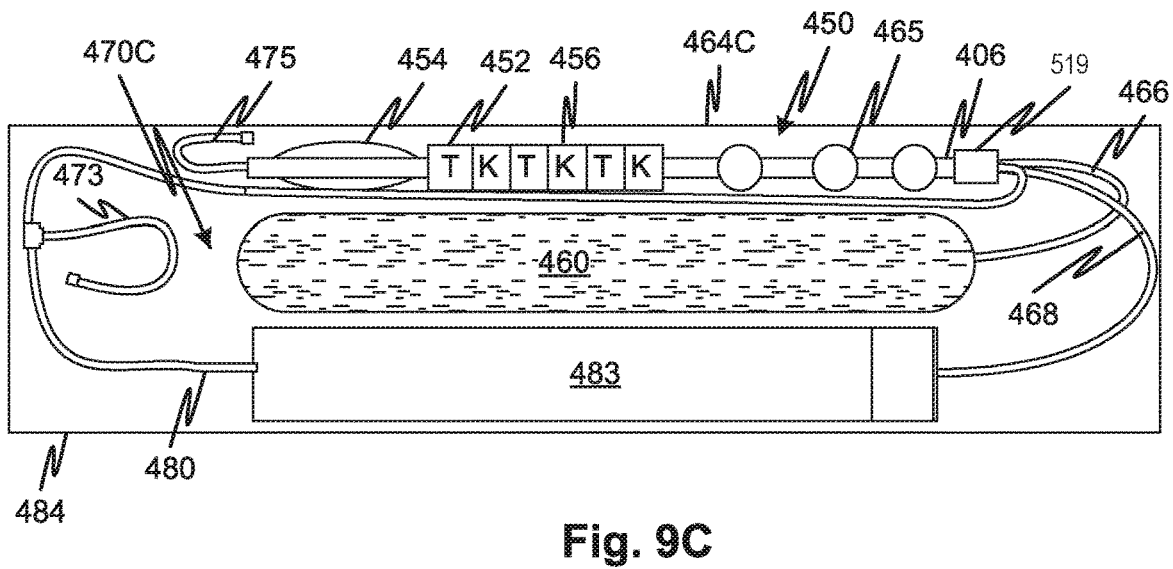
FIG. 9C shows a disposable including a fluid circuit cartridge and concentrate containers, one of the concentrate containers being connected to dilute saturate an inline applied flow of water to generate a concentrate, according to embodiments of the disclosed subject matter.

FIG. 9C shows a disposable 464C including a fluid circuit cartridge and concentrate containers, one of the concentrate containers being connected to dilute saturate an inline applied flow of water to generate a concentrate, according to embodiments of the disclosed subject matter. The concentrate container 460 contains a liquid concentrate. The container 483 is a cartridge of a type that receives water at an inlet 480 and produces a saturated solution from dry solute stored in the cartridge in the line 468. This type of cartridge is of a known type and typically used for bicarbonate solution generation for dialysate systems. The container 460 and cartridge 483 may correspond to containers 429 and 430 in the foregoing embodiments of FIGS. 8A and 8B in that fluid is drawn from them in the manner described. The example constituents are otherwise as described with respect to FIG. 9A including the variations. The concentrate container 460 and cartridge 483 may be pre-connected with the rest of the sealed fluid circuit 470C and sterilized after sealing. The concentrate container 460 and cartridge 483 may be packaged with the rest of the sealed fluid circuit 470C. The fluid circuit 470C may be pre-connected with all inlet and outlet line 473, 475 connections sealed and capped. As described above, the cartridge 450 may have conductivity 456 and temperature 452 sensors, an accumulator 454 and other elements. The cartridge 450 may also have tube pumping segments 465 that are aligned with pump actuators (such as peristaltic pump rollers) when the cartridge 450 is positioned with respect to the medicament proportioning module 104. The fluid circuit 470B, including container 460 and cartridge 483 and any other components required to make up the disclosed embodiments may be packaged in a container 484 such as a box or bag. In the foregoing embodiments 464A, 464B, and 464C, a water sterilizing filter 519 may be provided to safeguard against touch contamination in connecting the disposable 464A, 464B, and 464C to a water purification module 102.

In use, the cartridge may be removed from the container 484 and positioned in the medicament proportioning module 104. The container 460 and cartridge 483 (and others if present, depending on the number of components) can remain in the container or box 484. Any flexible tubes remain interconnected such as tubes 466 and 468. The water inlet line 473 can be uncapped and attached to the water purification module 102 and the water outlet line 480 can be uncapped and attached to the inlet of the cycler 106. In this way, minimal handling of the individual components can result in the set of the medicament proportioning module 104. In embodiments, the cartridge 450 can be separately packaged, for example in a plastic bag, and attached to the outside of a box within which the container 460 and cartridge 483 are held.

Figure 10:
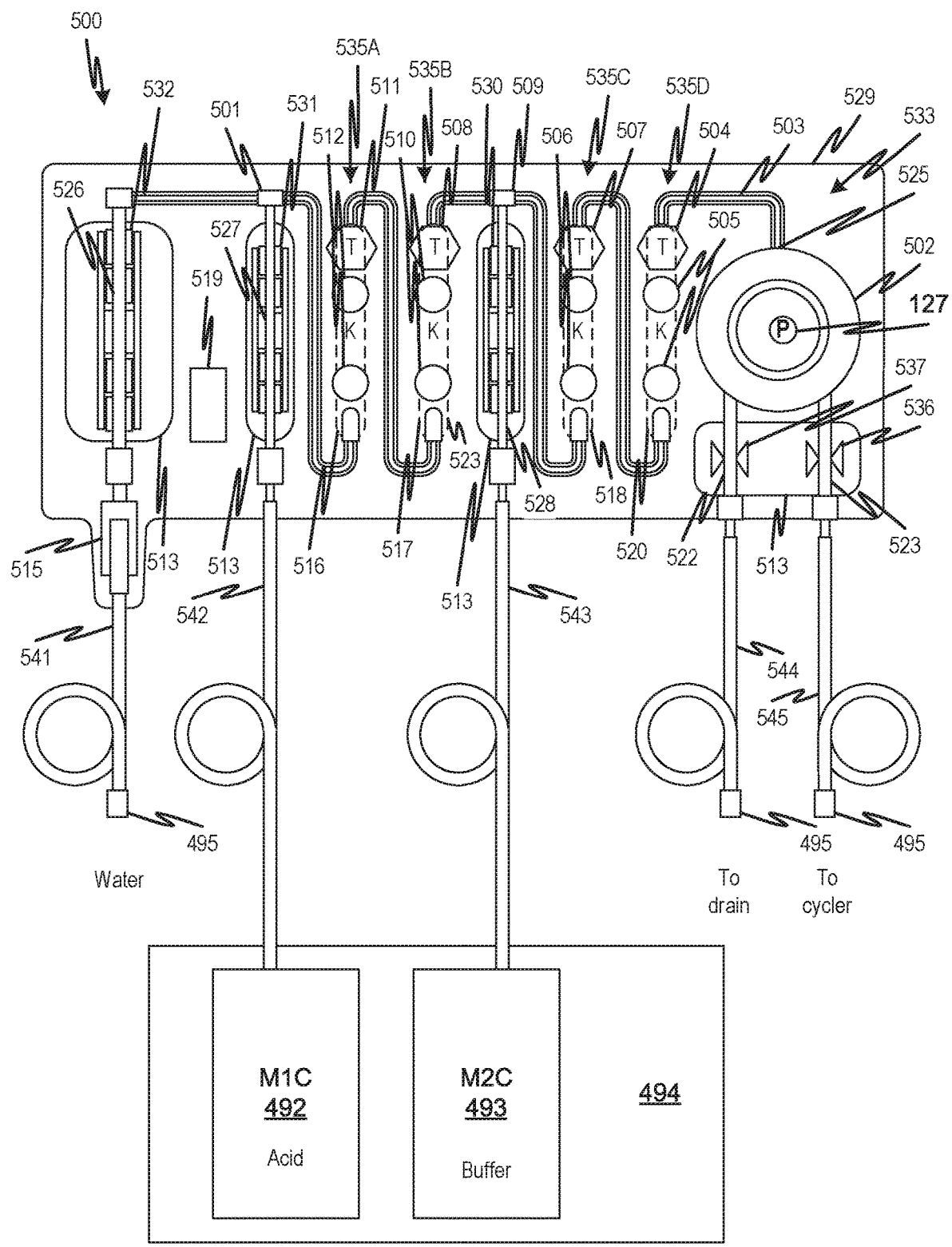
FIG. 10 shows further details of a fluid circuit cartridge according to embodiments of the disclosed subject matter.

Referring now to FIG. 10, an embodiment of a fluid circuit cartridge 500 may be substituted for any similar device described herein, including cartridge 450 of FIGS. 9A through 9C, cartridge 406 of FIGS. 8A and 8B and any fluid circuits incorporating the elements of cartridge 500 of FIG. 10 such as the fluid circuits of the medicament proportioning module 104 of any of the foregoing embodiments. The cartridge has a generally planar support 529 for the various fluid circuit elements. In embodiments a fluid circuit is embodied in by a fluid circuit pattern defined in the support 529, for example by molded channels or seam welding or a combination thereof. Alternatively the fluid circuit may be made up of discrete channel elements such as tubes, junctions, and valves. A fluid circuit 533 supported by the support 529 has channel elements 503 (indicated at 503 but also appearing at various locations as indicated), temperature measurement cells 504, 507, 508, 511 concentration measurement modules 535A, 535B, 535C, and 535D, pumping tube segments 526, 527, 528, an accumulator 502, pinch valve tube segments 522, 523, junctions 501, 509. Cutouts 513 in the support 529 allow pumping actuators 532, 531, 530 to mechanically access pumping tube segments 526, 527, 528, respectively, and valve actuators 536, 537 to access pinch valve tube segments 522, 523 in order to pump fluid or halt or allow the flow of fluid.

Pure water enters in line 541 from a water purification module 102 pumped by pumping actuator 532 through pumping tube segment 526. An inline sterile filter 515 ensures that any touch contamination, or any contamination, does not enter the cartridge fluid circuit. Pumping tube segment 526 (as well as segments 527 and 528) may of a specialized construction and material that provide low material creep and precise size to allow consistent and predictable rates to be provided through the regulation of the pumping actuator 532. The rate of rotation of the pumping actuator 532 is regulated by a controller (not shown) to provide a medicament product flow required by a downstream treatment such as a flow commanded by a cycler 106 and received thereby, or some other consuming device such as storage container.

A first concentrate is received through a first medicament concentrate line 542 and is pumped at a rate controlled by the controller to provide a predefined dilution rate of the combined flow emerging from the junction 501. The mixed diluted first concentrate flows into a first concentration measurement module 535A. Each concentration measurement module 535A-535D is described in more detail with regard to FIGS. 11A through 11D, infra. The mixed diluted first concentrate flows into the first concentration measurement module 535A and contacts conductive electrodes, one of which is indicated at 512. A current is driven through a column channel of the concentration measurement module 535*a* and a voltage drop is measured across the conductive electrodes 512 using the conventional four-point conductivity measurement scheme in order to reduce contact resistance error. The fluid emerging from the column channel is received in a temperature measurement cell 511 and then flows into a second concentration measurement module 535B with temperature measurement cell 508 and conductive electrodes 510 (only one indicated, but the other is evident by inspection). The second concentration measurement module 535B provides a redundant indication of conductivity and temperature to confirm accuracy by agreement between concentration measurement module 535A and concentration measurement module 535B. The controller or an independent module may output a signal or data indicative of concentration based on temperature and conductivity. The signals indicating conductivity and temperature may be converted to concentration responsively to stored (in a data store of the controller—not shown separately) conductivity-temperature curves for the solution received thereby. The same is done using temperature and conductivity signals from concentration measurement module 535C and concentration measurement module 535D as well.

The diluted first concentrate is received at a junction 509 where it combines with a flow of second concentrate pumped through the pumping tube segment 528 by pumping actuator 530. The second concentrate is drawn through a second medicament concentrate line 543. The flow rate of the diluted first medicament is determined by the combined flow rates of the flows in pumping tube segments 526 and 527 which are regulated by the controller (not shown) through control of the actuator (532, 531) speeds. In a similar manner, the flow through the pump segment 528 is regulated by the rate of the pumping actuator 530 such that the concentration of the mixture emerging from the junction 509, which includes the first and second concentrates plus the dilution water, is regulated by the relative rotation rates of the three pumping actuators 532, 531, and 530. In this example, the concentration of the mixture emerging from the junction 509 represents a final concentration of product medicament and it is measured using the concentration measurement module 535C and then redundantly measured using the concentration measurement module 535D. As described above, the concentration measurement module 535C and the concentration measurement module 535D have conductive electrodes 506 and 505, respectively and temperature measurement cells 507 and 504. The conductive electrodes 512, 510, 506, 505 (each of the numerals identifying a pair of conductive electrodes) make contact with fluid in a respective one of the conductivity measurement columns 516, 517, 518, 520 (shown in broken lines indicating they are behind the fluid circuit 533 support 529.

The product medicament flows into a diaphragm chamber of an accumulator 502 which reduces flow fluctuations by expanding and contracting with the help of an urging element as can be seen in reference to FIGS. 12A, 12B, 8H, 8J, and understood from the attending discussions. Flow enters the accumulator 502 at a junction 525 and flows out through a pair of pinch clamp segments 522 and 523, each leading to a respective outlet line 544 and 545. The outlet line 544 is connected to a drain and the outlet line 545 is provided with a connector for connection to a consuming device such as cycler 106. The cartridge 500 may be pre-connected with concentrate containers 492 and 493, capped with caps 495 so that the entire assembly is sealed from the environment, and sterilized before packaging for delivery and/or storage. The cartridge 500 may attached to a rigid container 494 such a box such that it can be removed from the container 494 and slid onto a shelf while positioning the cartridge 500 in the medicament proportioning module 104, where the first medicament concentrate line 542 and second medicament concentrate line 543 are of sufficient length to allow them to extend between the positioned cartridge 500 and a storage by for the container 494. In embodiments, the container 494 can be a cardboard box or plastic box.

Figure 12A:
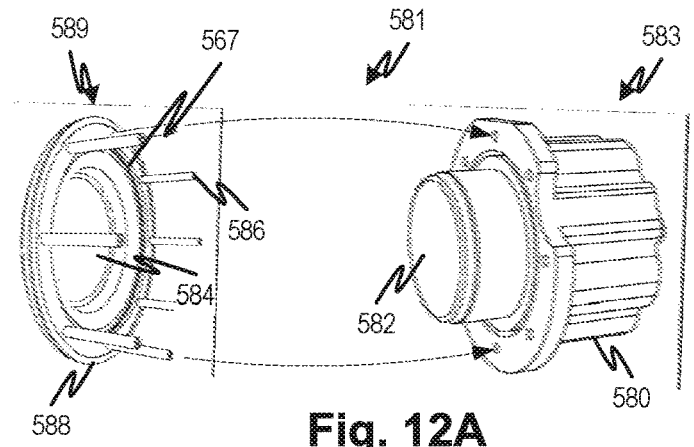
FIGS. 12A and 12B show a pressure regulating component that, according to embodiments, can be employed with the fluid circuit cartridge of FIG. 9C and others disclosed herein, according to embodiments of the disclosed subject matter.
Figure 12B:
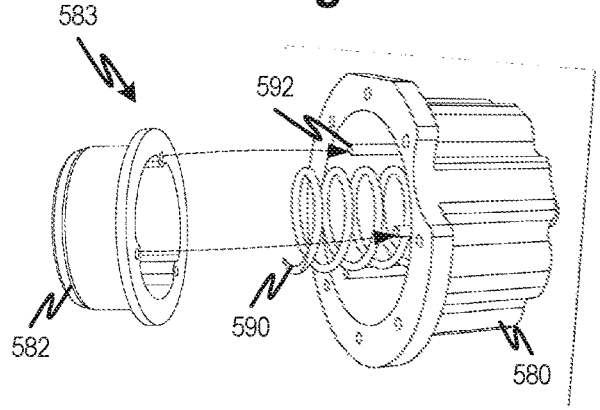
Figure 12C:
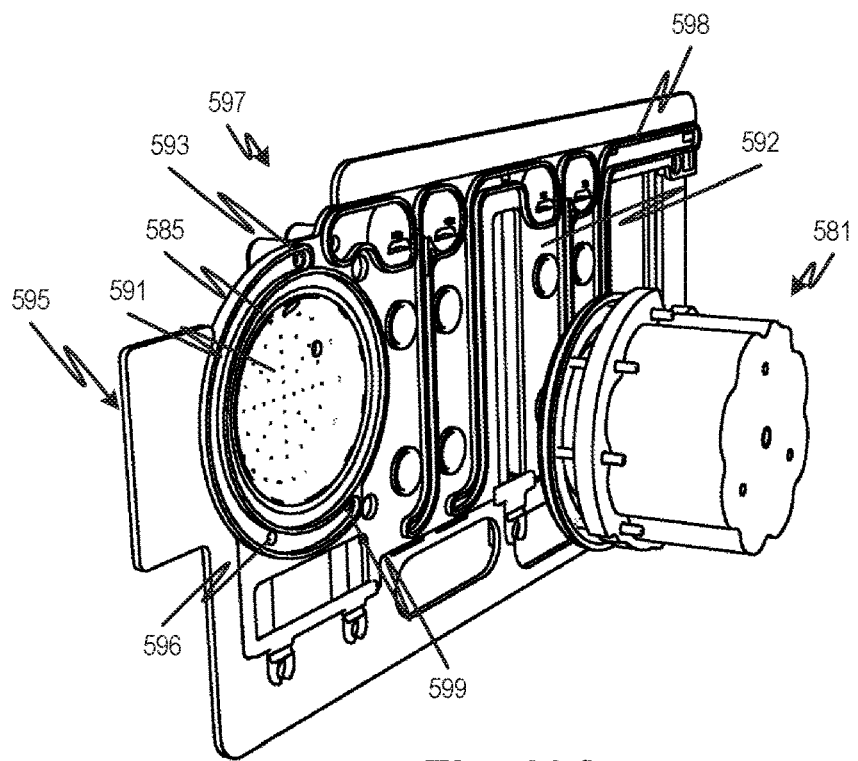
FIG. 12C shows the embodiment of FIGS. 12A and 12B with a fluid circuit cartridge according to embodiments of the disclosed subject matter.

Referring to FIGS. 12A, 12B, and 12C an urging mechanism 581 includes a flexible cover 589, with a retaining ring 588 bolts (592) to a constant pressure mechanism 583 that has button 582 that slides within a housing 580 urged by a spring 590. In an embodiment of a fluid circuit cartridge 597, shown in FIG. 12C, flow enters the accumulator 591 through an entry 593 and flows out of the accumulator 591 through a pair of openings 596 and 599. A fluid circuit portion of the cartridge is formed from a planar member 592, which may be formed by injection molding, with wall features formed on the wall that create the various flow channels when they are sealed by an overlying film (not apparent in the drawing but joining adjacent wall features to form the channels). The film may be thermally bonded, welded or glued in place as mentioned elsewhere. The flow is guided through the fluid circuit 597 cartridge by channels 598. The internal volume of the accumulator 591 is formed in the same way as the channels with an extra step. A film is attached to a round wall 585 thereby forming one side of the accumulator chamber. The film is then heated so that it stretched into the accumulator 591 interior volume thereby providing flexible wall of the accumulator so that it can behave as a diaphragm or bladder.

The film forming a flexible wall of the accumulator 591 (formed by a film as discussed below) presses against the cover 589 in turn applying a force against the button 582 causing the spring 590 to contract. The button 582 floats on an elastic (e.g., neoprene) web 567 that is held at its periphery by the ring. The button may be bonded to the elastic web 567 such that it floats and requires to sliding or rolling-bearing guide that might produce more friction. The urging mechanism 581 thus beneficially provides very little hysteresis in the force applied during forward and backward movement as it compensates volume changes in the accumulator. At the same time, the restoring force of the spring and elastic web cause the button 582 to seek a central position as they relax. As fluid flows through the diaphragm chamber 591, any excess pressure, which is determined by the spring constant of spring 590 and the effective area of the button 582, causes the diaphragm chamber 591 to expand as the spring 590 contracts. This compensates an increase in pressure that might otherwise occur in a non-compliant channel. This allows the pumps of the upstream water purification module 102 and medicament proportioning module 104 to continue running at a uniform rate even if a cycler 106 or other consuming appliance demands product medicament fluid in a periodic or uneven fashion. The illustrated fluid circuit cartridge 597 has features as discussed above with reference to FIG. 10 and further includes a handling tab 595 to aid insertion of the fluid circuit cartridge 597. In use, the urging mechanism 581 is pressed against the diaphragm chamber 591 when the fluid circuit cartridge 597 is installed in the medicament proportioning module 104. In the drawing the urging mechanism 581 is shown separated from the diaphragm chamber 591 for clarity. The accumulator is formed by a circular wall that is part of the 598

Referring to FIGS. 11A through 11D, a concentration measurement module 535 as described above is now detailed according to an example embodiment. A section of a cartridge support 556 may correspond to a portion of 9C, cartridge 406, or the support 529 of cartridge 500 described above. Thus the edges of the cartridge support 556 may be considered to extend and not be limited to the particular shape or size illustrated, the portion shown being merely a portion of a larger support structure. An inlet flow of conductive fluid enters through an inlet channel 566 molded into the cartridge support 556. A wall 467 rises from the plane of cartridge support 556 to define the channel 566. The edge of the wall 567 may be sealed with a plastic film to make channel 566 pressure-tight. Flow, indicated by arrow 564, entering the channel internal volume 557 from other parts of the cartridge support 556 leaves the channel 566 through an opening 568 where it flows into a flow column housing 575 as indicated by arrows 574, and flows from an end opposite the entry to an opening 570 in cartridge support 556. From there, the flow traverses a temperature measurement chamber 563 toward an exit channel 572 which is on an opposite side from the opening 570 where the flow entered the temperature measurement chamber 563. The flow leaves the concentration measurement module 535 as indicated by arrow 562. The temperature measurement chamber 563 and channel 572 may be sealed in the same fashion as channel 566 such that the temperature measurement chamber 563 forms a flat broad chamber. A temperature transducer may be placed against the face of the film that is used to close the temperature measurement chamber 563 providing a broad contact area for accurate temperature measurement that limits edge losses that can bias the temperature measurement. In addition, a zero-flux temperature sensor can be used which actively cancels heat flux due to conduction through the major face of the temperature measurement chamber 563 finds excellent application here because of the high sensitivity of concentration to temperature. Bosses 552 may be provided for support and additional structure and sealing competence in the cartridge support 556.

Figure 11A:
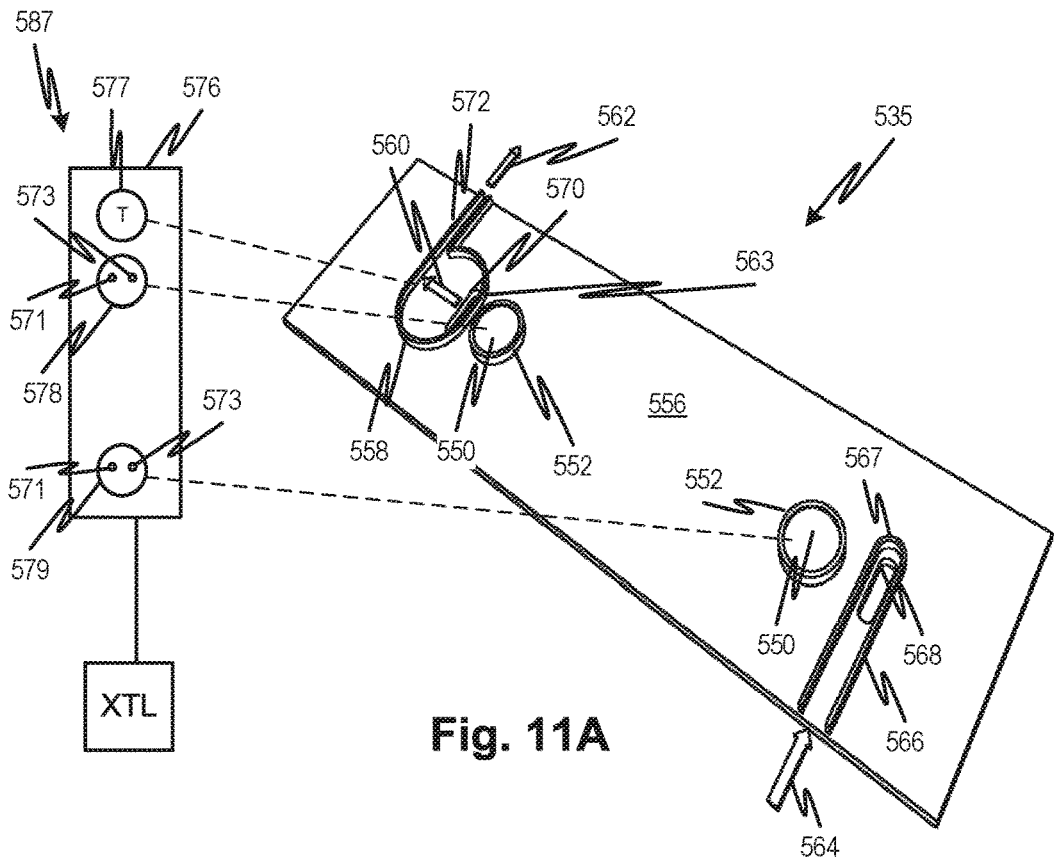
FIGS. 11A through 11D show features of a conductivity and temperature measurement cell that, according to embodiments, can be integrated in the fluid circuit cartridge of FIG. 9C and others disclosed herein, according to embodiments of the disclosed subject matter.
Figure 11B:
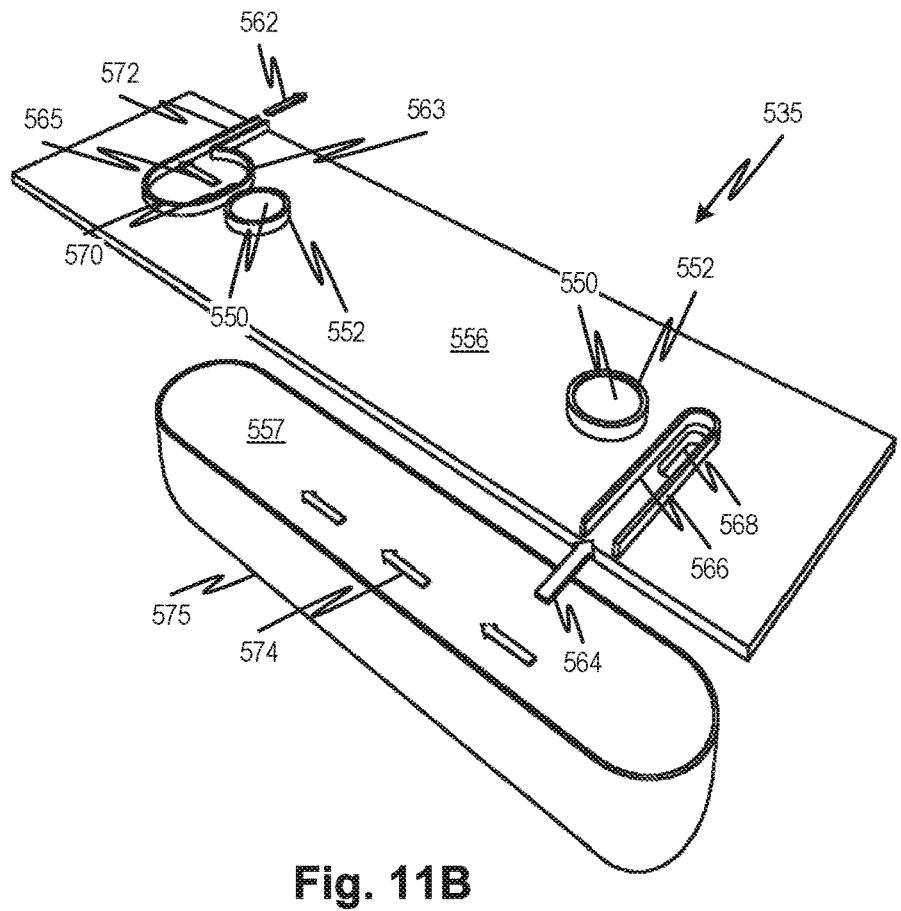
Figure 11C:
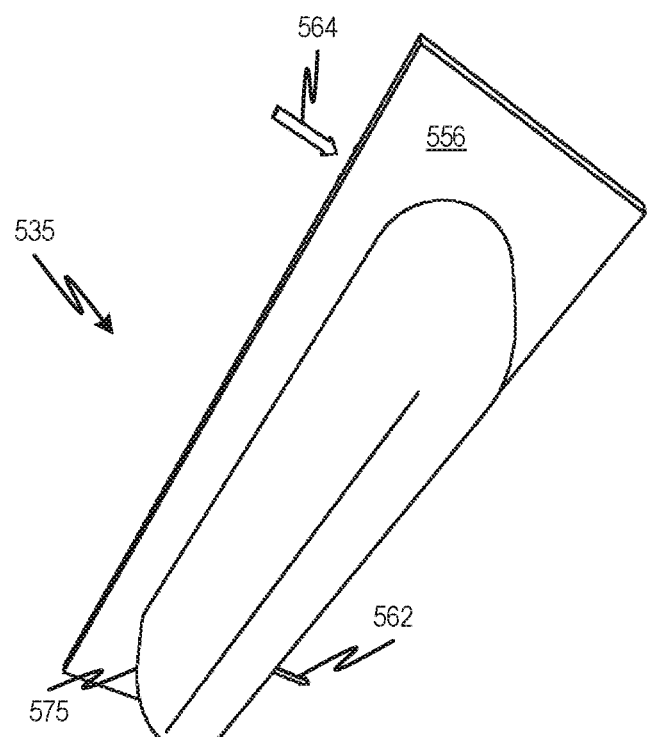
Figure 11D:
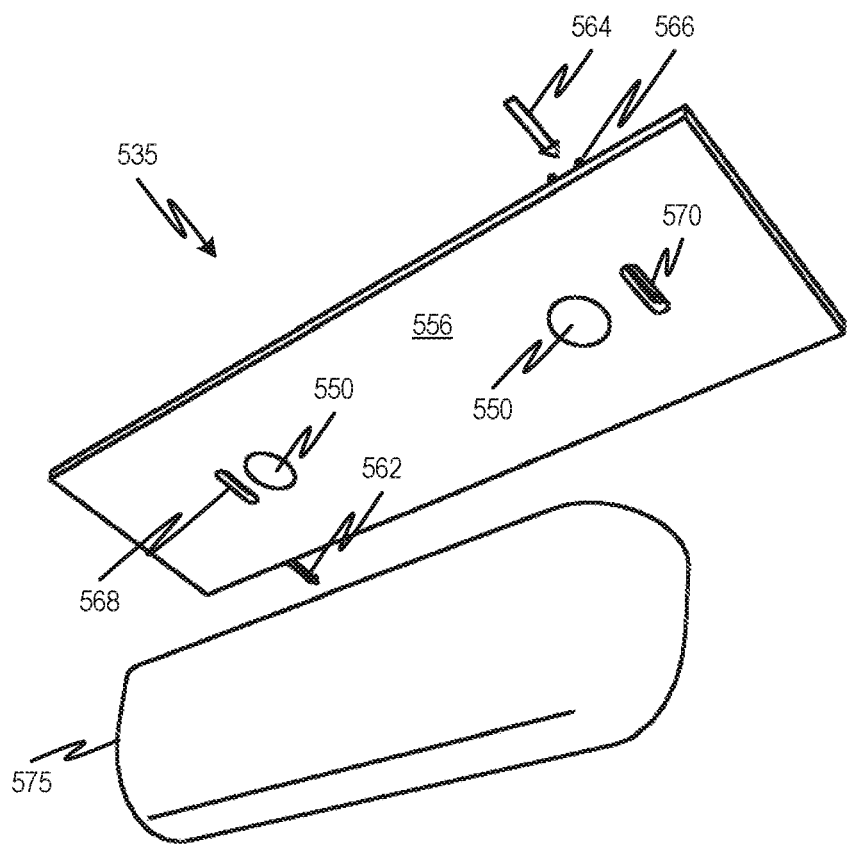

Conductive electrodes 550, 577 may be bonded, welded, press-fitted, molded or otherwise affixed to the cartridge support 556 (a portion being shown at 576). In use, spring biased contacts 571 and 573 are pressed into each conductive electrode 550 while at the same time, a temperature transducer 577 is held against the temperature measurement chamber 563 as an sensor backplane 587 portion is held against the concentration measurement module 535 as a result of the entire cartridge being positioned in place in medicament proportioning module 104 and engaged for use. That is, when a cartridge of any of the embodiments, carrying the concentration measurement module 535 is positioned in place in a medicament proportioning module 104 and registered, the spring biased contacts 571 and 573 and temperature transducer 577 are placed against the conductive electrodes 550 and temperature measurement chamber 563 so that measurements can be taken by the connected controller. Note that FIGS. 11B and 11D are exploded views.

Figure 13A:
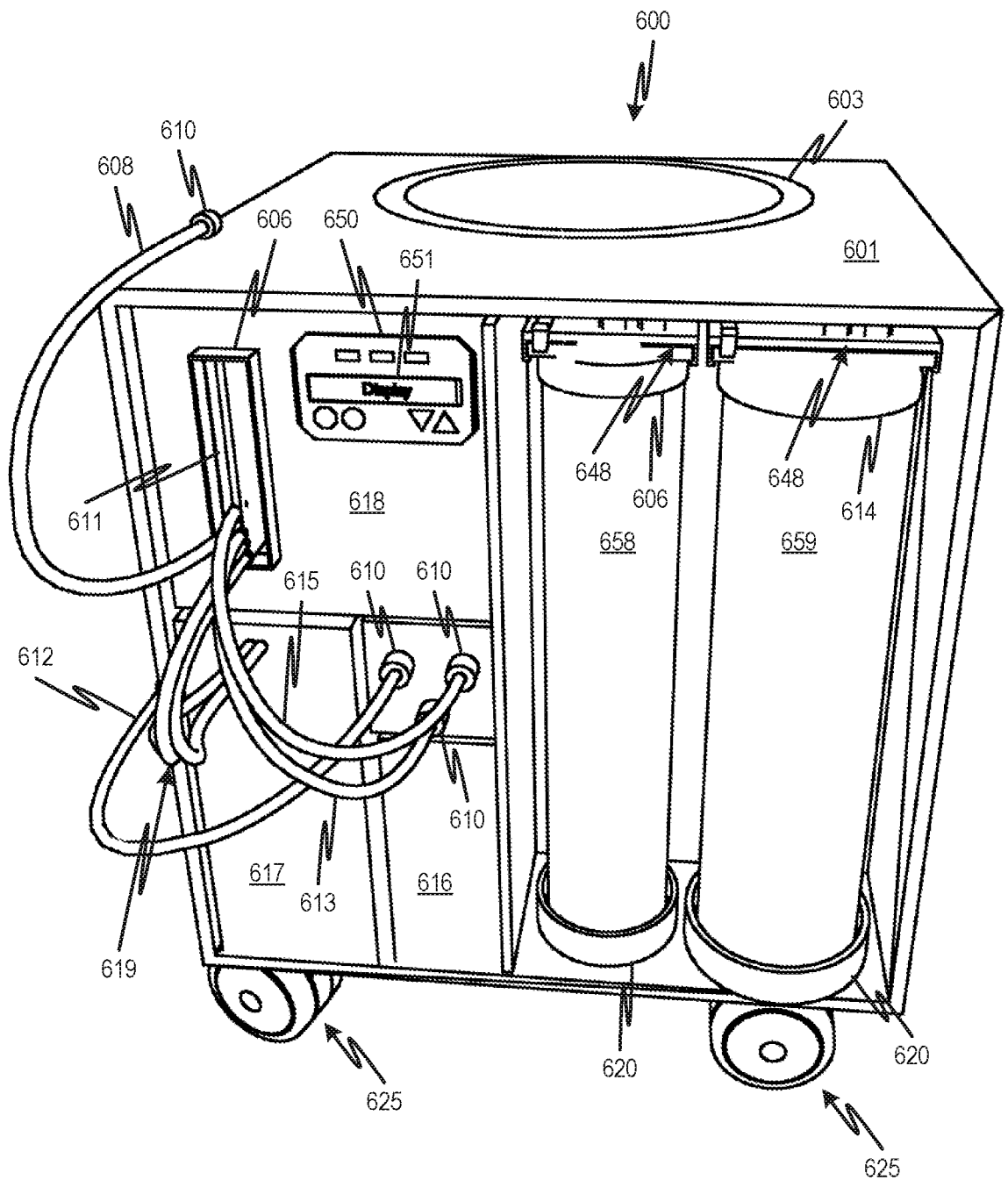
FIGS. 13A and 13B show front (FIG. 13A) and back (FIG. 13B) sides of a medicament preparation system, according to embodiments of the disclosed subject matter.
Figure 13B:
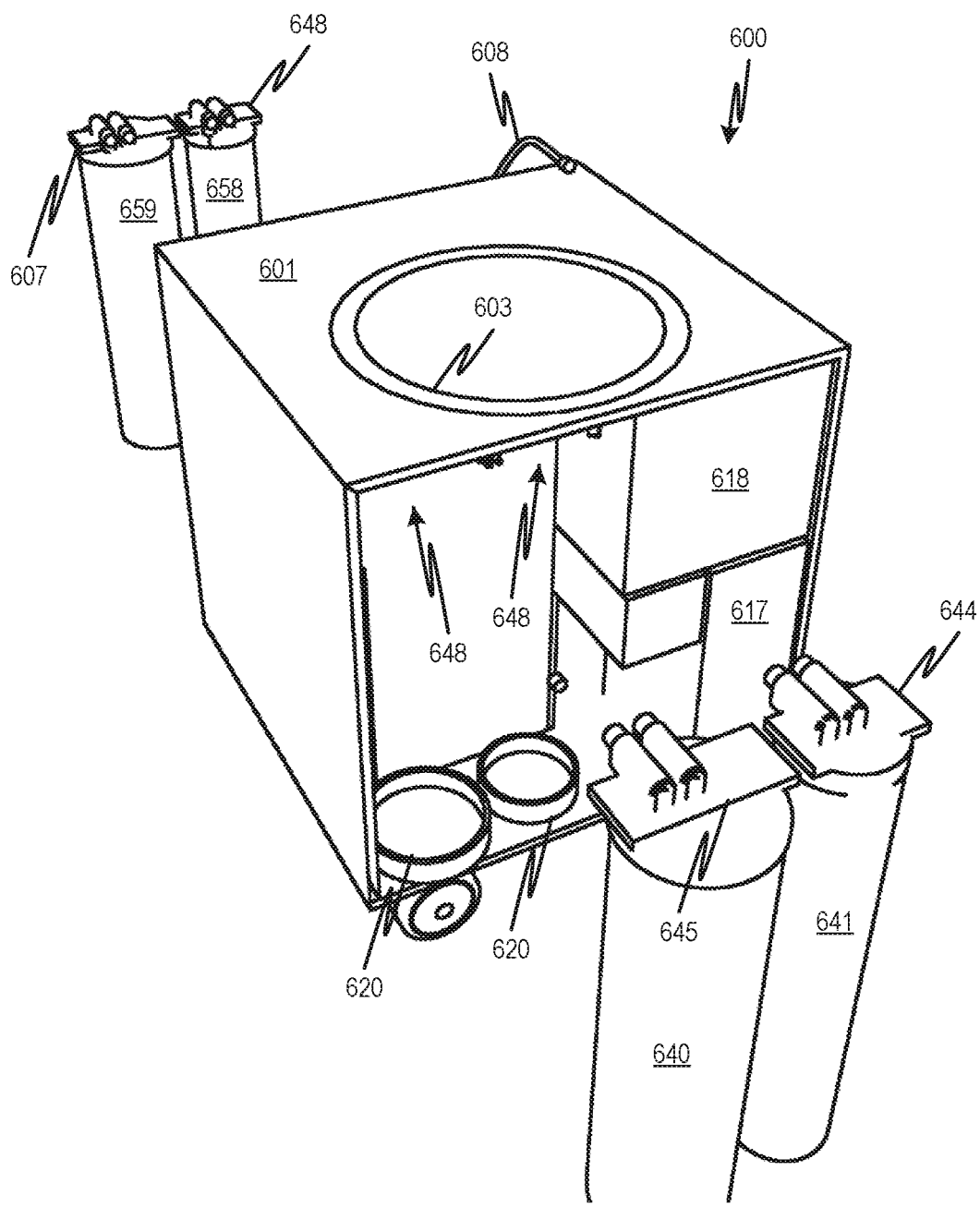

FIGS. 13A and 13B show front (FIG. 13A) and back (FIG. 13B) sides of a medicament preparation system 600 with replaceable components 640, 641, 658, and 659, in FIG. 13B shown separated from medicament preparation system 600 and oriented for installation. The medicament preparation system 600 may combines water purification module 102 and medicament proportioning module 104 that with a support for a cycler 106 (not shown) which can be positioned in a track 603. A housing of the medicament preparation system 600 is generally cubic in shape. The replaceable components are a cation resin bed 659 and an anion resin bed 658 that together form a primary stage of a deionization filter, a carbon filter 640, and a mixed (cation/anion resin) bed 641 that forms a secondary stage of the deionization filter. Together these correspond, respectively to activated carbon filter 204, primary resin cation stage 205, primary resin anion stage 206, mixed resin bed 208, which were discussed above. A product medicament line 608 for output of product medicament is shown with a connector 610. This may be connected to a cycler 106 or other medicament consuming device that may sit on top of a housing 601 of the medicament preparation system 600. Respective catch mechanisms 648 guide engagement caps 607, 614, 644, and 645 and fluidly connect and retain, the cation resin bed 659, anion resin bed 659, carbon filter 640, and mixed bed 641, respectively. The catch mechanisms 648 and engagement caps are described in further detail below. Lower receiving support fixtures 620 receive lower ends of respective ones of the cation resin bed 659, anion resin bed 659, carbon filter 640, and mixed bed 641. A respective one of the latter may be installed by positioning its lower end in a respective one of the lower receiving support fixtures 620 and tilting upright into a respective one of the catch mechanisms 648 to make fluid connections and hold the respective one of the cation resin bed 659, anion resin bed 658, carbon filter 640, and mixed bed 641 in place.

A control and cartridge receiving module 618 has a user interface with control keys and a display 651. A receiving slot 606 receives a cartridge 611 which may conform to any of the cartridges 406, 450, or 500, and other of similar description. Actuators and sensors (not shown here) within the receiving slot 606 engage the pumping and valve tubes and sensors as well as electrical contacts of the foregoing cartridge embodiments, particularly cartridge 500. Ultrafilter module 616, which may correspond to sterile filter stage 210, may be loaded from the medicament preparation system 600 front side. The medicament concentrate disposable package 617 may also be loaded from the medicament preparation system 600 front side and may correspond to the container or box 484 housing the fluid circuit 470A, 470B, or 470C. The cartridge may have additional lines including a pure water inlet 613 to carry purified water into the cartridge 611 and a drain line 615 to carry diverted medicament to a waste outlet via internal plumbing in the housing 601 that also routes water to a waste outlet from the medicament preparation system 600 (not shown). Tap water may be provided to the water purification module 102 via tap water line 612 also connected at the front of the housing 601. Medicament concentrate lines 619 may flow medicament from the medicament concentrate disposable package 617 to the cartridge 611 for proportioning with the purified water that is conveyed from the water purification module 102 through the pure water inlet line 613. Connectors 610 provide connections to the various ports for the identified fluid lines. An additional water-in line that creates a saturated concentrate from powdered solute in embodiments of medicament concentrate disposable package 617 may be provided in variations of the medicament preparation system 600 as shown in FIG. 13C, discussed below.

Figure 13C:
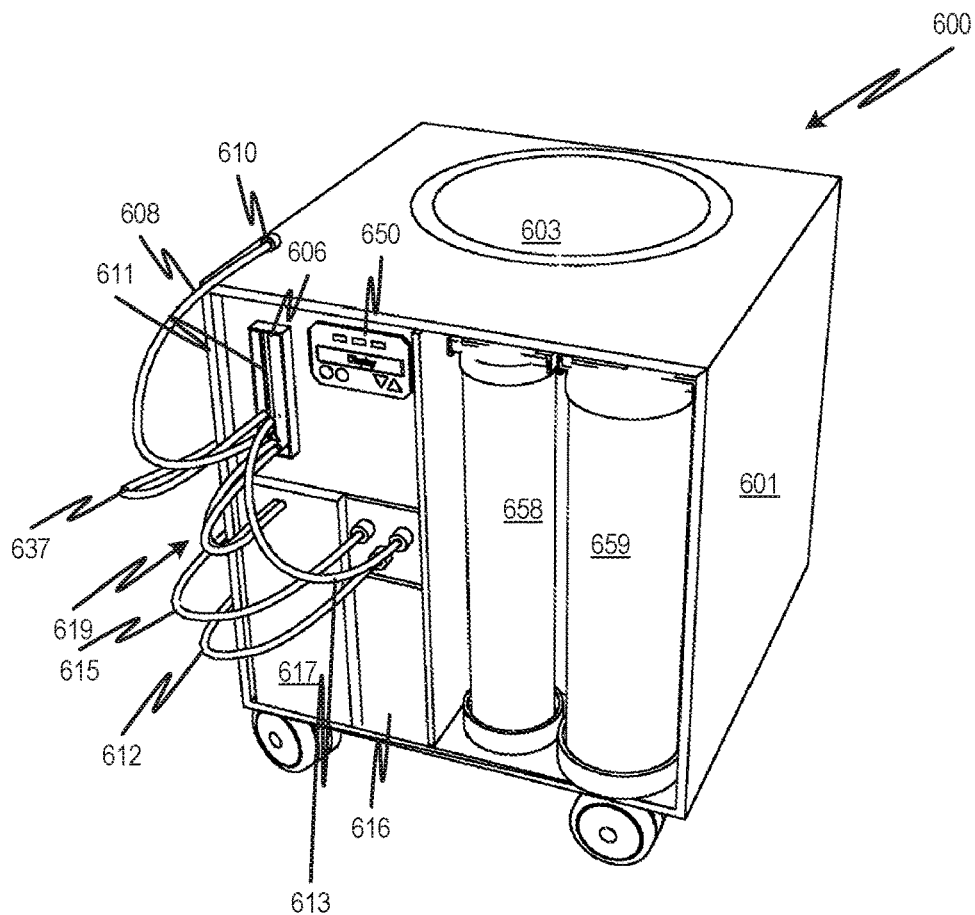
FIGS. 13C, 13D, and 13E illustrate a medicament preparation system and connecting scheme, according to further embodiments of the disclosed subject matter.
Figures 13D, 13E:
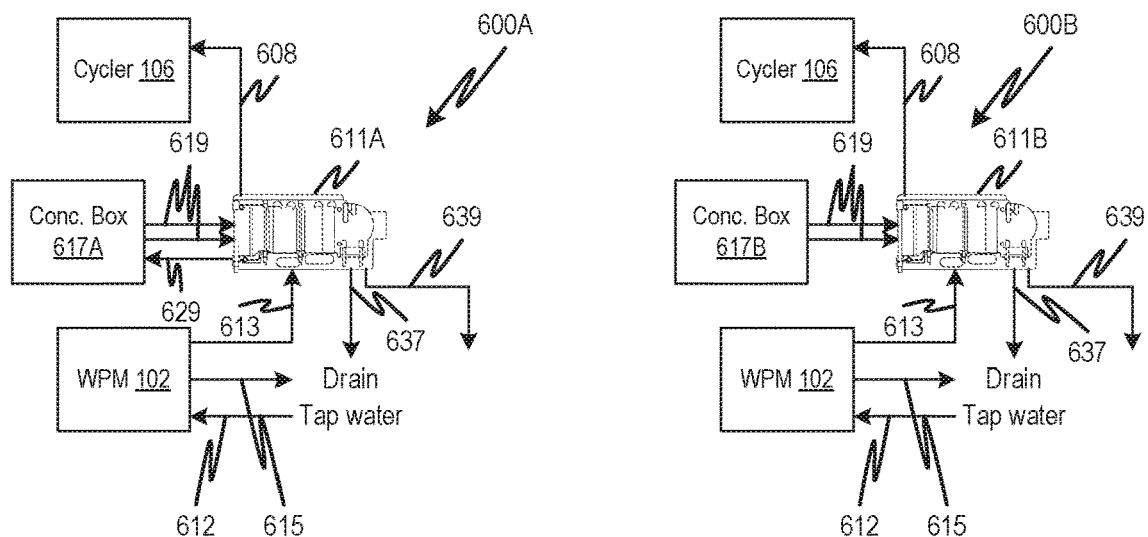

FIGS. 13C, 13D, and 13E show connection schemes according to the disclosed embodiments. A medicament preparation system 600 which is similar to those discussed elsewhere uses replaceable components 640, 641, 658, and 659, as in FIG. 13A and as described elsewhere. An interconnection scheme is illustrated for allowing the attachment of the water purification components of a water purification module 102 housed in the housing 601 of the medicament preparation system 600 to tap water (received through tap water line 612) and drains some water as explained above (through drain line 615), as well as connecting a product water output to a medicament proportioning module 104 whose fluid circuits are entirely disposable. The medicament concentrate disposable package 617 is connected to the cartridge 611 to receive concentrate through lines 619. A medical treatment device such as a cycler receives product medicament from the cartridge through a product medicament line 608 connected to the cartridge 611. The cartridge receives pure water through pure water inlet line 613. In the case where dry buffer is provided in the medicament concentrate disposable package 617 rather than a liquid concentrate buffer or a mixed concentrate with acid and buffer already mixed (e.g., lactate or acetate buffer), pure water received by the dry medicament cartridge 611A in disposable package 617 through a pure water bridge line 629 which is connected to the pure water inlet line 613 and controlled by an actuator in the receiving slot 606 for the cartridge 611. Product medicament 639 and waste 637 may exit from the cartridge 611B, the former being connected to a drain and the latter to a consuming device.

As in system 600, the medicament preparation system 600A may combine water purification module 102 and medicament proportioning module 104 that with a support for a cycler 106 which can be positioned in a track 603. As in the earlier embodiments, the replaceable components are a cation resin bed 659 and an anion resin bed 658 that together form a primary stage of a deionization filter, a carbon filter 640, and a mixed (cation/anion resin) bed 641 that forms a secondary stage of the deionization filter. Together these correspond, respectively to activated carbon filter 204, primary resin cation stage 205, primary resin anion stage 206, mixed resin bed 208, which were discussed above. An output line for product medicament 608 is shown with a connector 610, as in the embodiment of FIG. 13A, and may be connected to a cycler 106 or other medicament consuming device that may sit on top of a housing 601 of the medicament preparation system 600A. Connection mechanisms are as described above for the cation resin bed 659, anion resin bed 659, carbon filter 640, and mixed bed 641, respectively as are the support fixtures.

The control and cartridge receiving module 618 has a user interface with control keys and a display 651. In the embodiment of FIG. 13C, the receiving slot 606 may receive a cartridge 611A adapted for interfacing with a fluid circuit that uses a bicarbonate cartridge (contained in the medicament concentrate disposable package 617A) as described with reference to FIG. 8B, 15B (infra) and elsewhere. Actuators and sensors within the receiving slot 606 engage the pumping and valve tubes and sensors as well as electrical contacts of the cartridge 611A. Ultrafilter module 616 and medicament concentrate disposable package 617A (similar to medicament concentrate disposable package 617) are as discussed elsewhere.

A tap water line 612 conveys water from a tap to the water purification module (which may be as in any of the disclosed embodiments consistent with the present description). Pure water inlet line 613 directs pure product water from the cartridge to the medicament concentrate disposable package 617 for use in creating a saturated bicarbonate solution using the bicarbonate cartridge as discussed elsewhere. The medicament preparation system 600A may also have a drain line 637 leading from the cartridge 611A to a drain (See for example waste line 422 outlet line 544 outline line 545 and other similar examples of cartridges that may be employed in the present embodiment). Medicament concentrate lines 619 bring medicament concentrate from the medicament concentrate disposable package 617 to the cartridge 611A for proportioning with the purified water carried through line 613. Connectors 610 provide connections to the various ports for the identified fluid lines. An additional pure water line 629A conveys some of the pure water conveyed through 613 that creates a saturated concentrate from powdered solute in embodiments of medicament concentrate disposable package 617 may be provided in variations of the medicament preparation system 600A. The embodiment 600A shown schematically in FIG. 13D uses a medicament concentrate disposable package 617 that contains a dry buffer cartridge and therefore receives pure water through additional pure water line 629. The embodiment 600B shown schematically in FIG. 13E uses a liquid medicament concentrate buffer in medicament concentrate disposable package 617 and therefore does not have an additional pure water line 629 for the cartridge 611B.

Figure 14A:
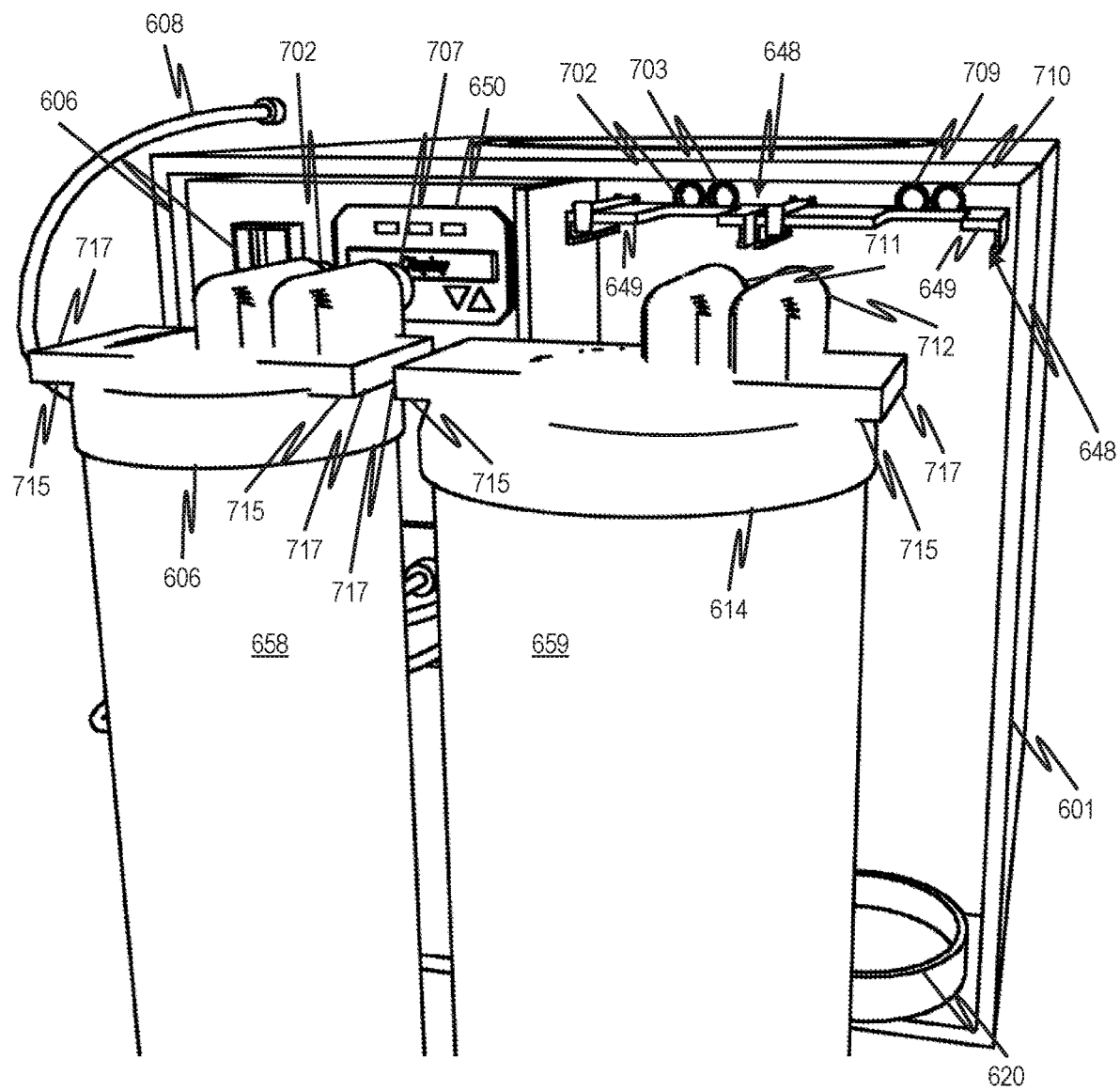
FIGS. 14A through 14D illustrate disposable filter cartridge connection and other mechanical features of a medicament preparation system, according to embodiments of the disclosed subject matter.
Figure 14C:
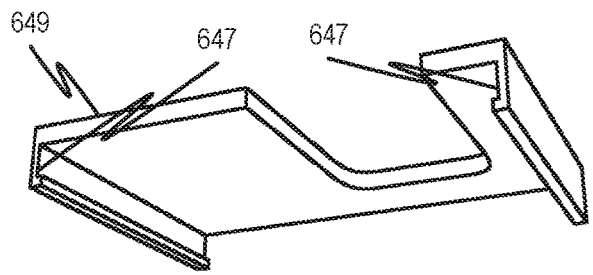
Figure 14B:
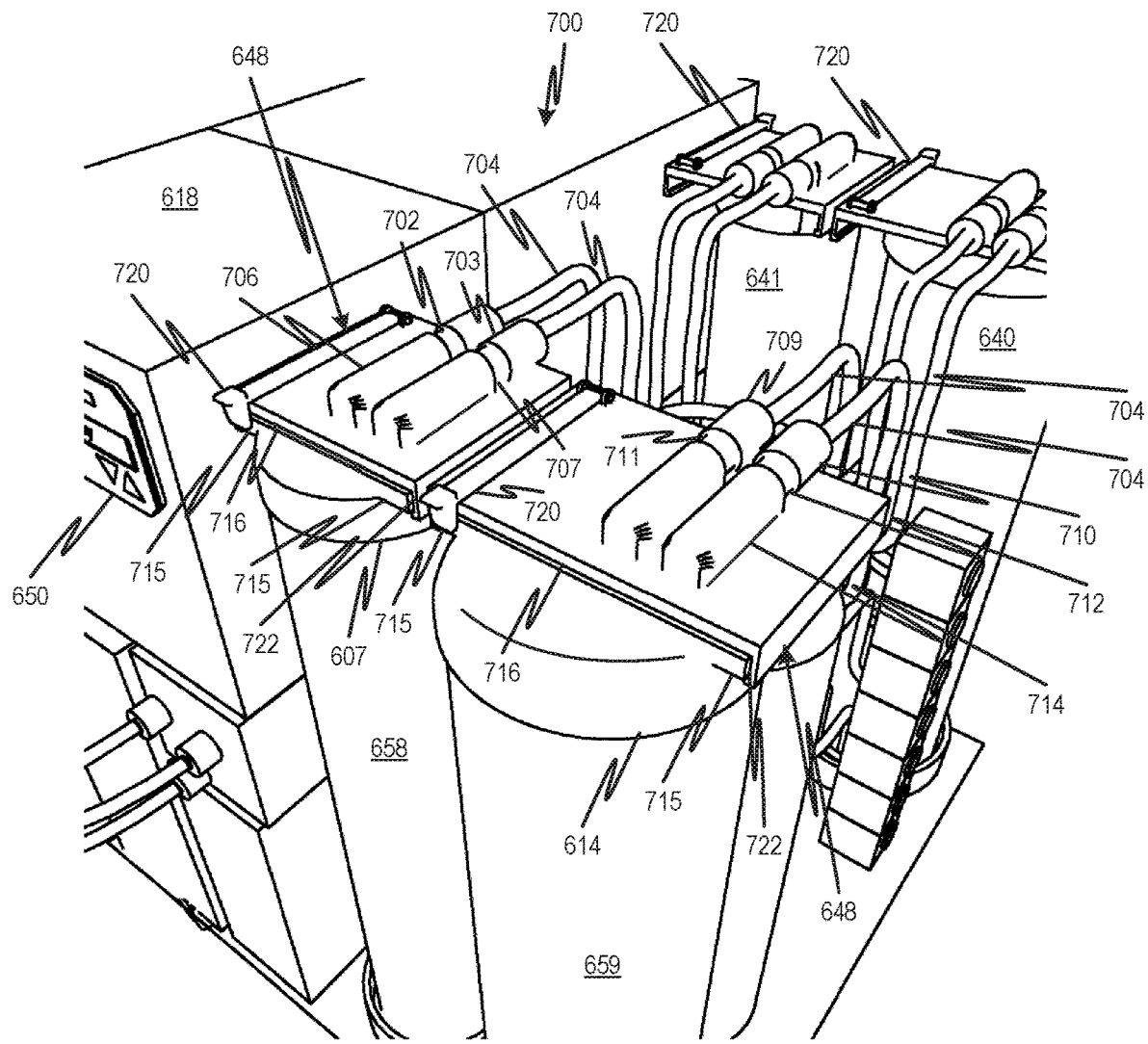
Figure 14D:
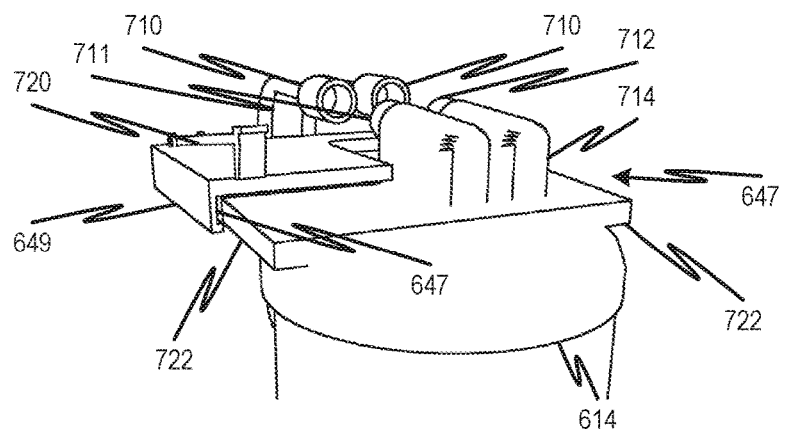

FIGS. 14A and 14B illustrate disposable filter cartridge connection and other mechanical features of a water purification module 700 module of the medicament preparation system 600, according to embodiments of the disclosed subject matter. Guide engagement caps 607 and 614 form a first part of the catch mechanisms 648 mentioned above which secure the cation resin bed 659, anion resin bed 658, carbon filter 640, and mixed bed 641 in place and make the fluid connections therefore. That is, each of the modules for the cation resin bed 659, anion resin bed 658, carbon filter 640, and mixed bed 641 has a respective guide engagement cap 614, 607, 645 and 644. Each engagement cap has alignment portions 715 shown FIG. 14B that have straight side tabs 717 the fit into slots 647 of a bracket 649 of each catch mechanism 648. The bracket is shown separately in FIG. 14C. The straight side tabs 717 are aligned in the vertical direction with the slots 647 when each of the cation resin bed 659, anion resin bed 658, carbon filter 640, and mixed bed 641 is placed in a respective lower receiving support fixture 620. In order to slide into each slot 647, the respective guide engagement cap 614, 607, 644, 645 has to be oriented with its edge 717 parallel to the slot 647. This forces the fluid couplings 702, 707 of anion resin bed 658 and fluid couplings 711, 712 of cation resin bed 659 to align respectively with receiving couplings 702, 703, 709, 710 of the medicament preparation system 600. The receiving couplings 702, 703, 709, 710 may be provided with a spring device that pushes the fluid couplings 702, 707 of anion resin bed 658 and fluid couplings 711, 712 of cation resin bed 659 away so as to force the installer to push against this force until a latch 720 on each catch mechanism 648 engages and retains the respective alignment portion 715, 716. In this way fluid lines 704 are connected with respective portions of the medicament preparation system 600. The above details of catch mechanism 648 of anion resin bed 658 and cation resin bed 659 were described, however the same details may apply to those of carbon filter 640 and mixed bed 641 and associated fluid couplings and receiving couplings. FIG. 14D shows the latch 720 in a raised position where it may be held by a user during the positioning of a respective guide engagement cap 614, 607, 645 and 644. When released, the latch 720 is urged into a retaining position as indicated in FIG. 14B and others. Although the with its edges 715, 717 for example (and similar elements) and the bracket 648, 649 slots 647 are illustrated as straight, to reduce tolerance one or both may be curved at radii corresponding to a radius whose center is near the lower receiving support fixture 620 to reduce the tolerance required. Alternatively one or both may beveled to cause a low tolerance fit near the final position of engagement.

Figure 15A:
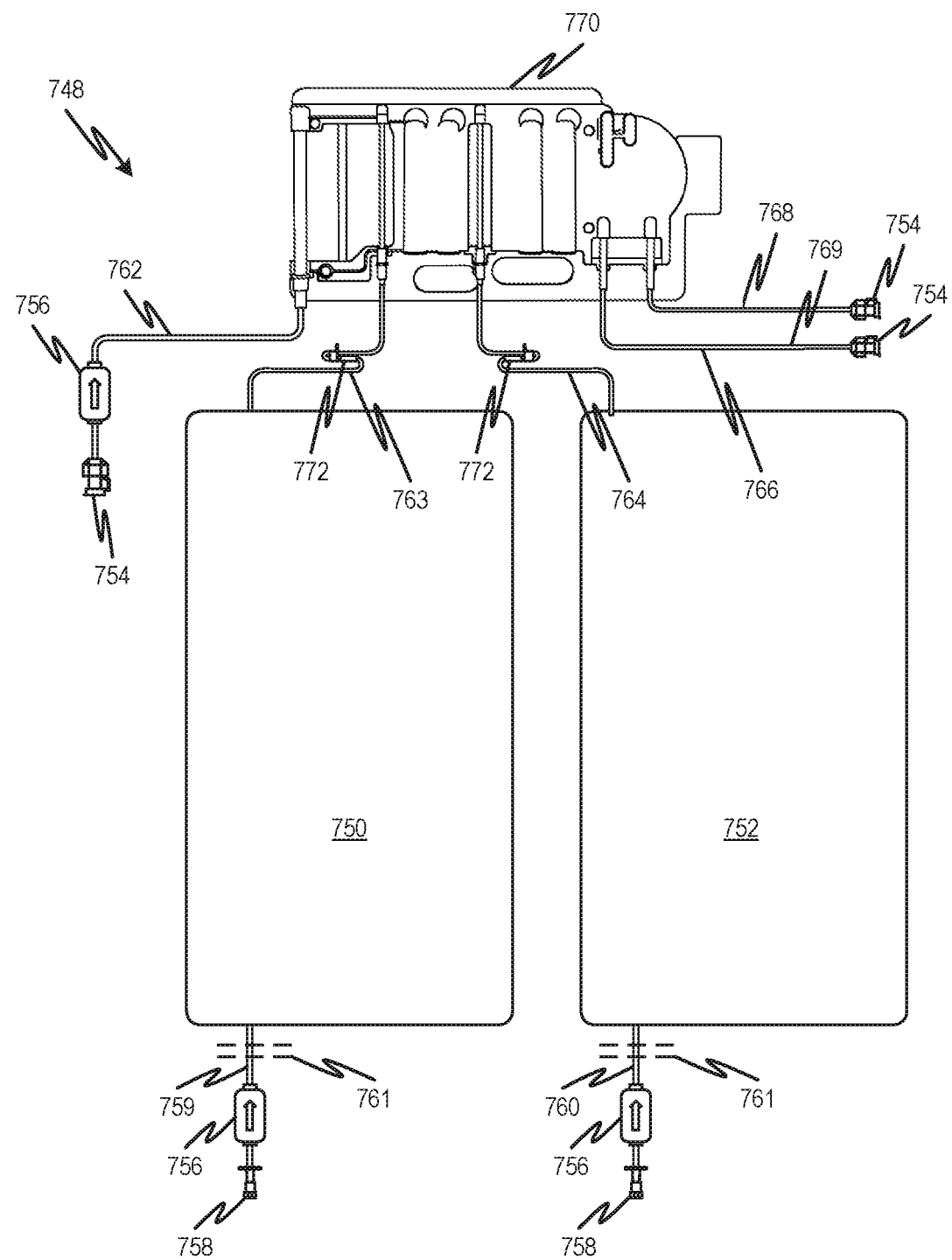
FIGS. 15A and 15B illustrate disposable fluid circuits and features involved in their assembly, according to embodiments of the disclosed subject matter.

Referring now to FIG. 15A, a cartridge 770 may provide the fluid circuit elements described with reference to any of the above cartridge embodiments including concentration sensor stations, accumulator, valve clamping tube segments, and pumping tube segments which are oriented and positioned by mounting the cartridge. The cartridge 770 may also have a data carrier as described that provides data concerning characteristics of the cartridge and all the fluid circuit elements of the fluid circuit 748 indicated by reference-numeral 748, including the composition of medicament concentrates contained in attached containers 750 and 752. An inlet line 762 has an inline sterile filter 756 and a primary inlet 754 connectable to a source of pure water which is capped and sealed. A first medicament concentrate line 763 and a second medicament concentrate line 764 are connected to allow concentrate to be pumped into a medicament supply line in a predefined proportion with water pumped through inlet line 762. Kink-type clamps, which are described in, for example, International Publication No. WO 2007/118235 (see, for example, FIGS. 30A through 32 of said publication) seal the first medicament concentrate line 763 and the second medicament concentrate line 764, respectively. Waste line 769 and product medicament line 768 lead out from a common medicament supply line and capped and sealed as indicated at 754. Concentrate feed inlets 759 and 760 are provided to fill the concentrate containers 750 and 752, respectively, through sterile filters 756. The entire fluid circuit may be sealed, including the kink-type clamps 772, and respective medicament supplies may be connected to connectors 758. Medicament concentrate may be pumped into the concentrate feed inlets 759 and 760 until a predefined quantity is supplied, then the concentrate feed inlets 759 and 760 can be welded to seal them at a point therealong as indicated at 761. The welding can simultaneously cut off the filter 756 and 758. Then the entire fluid circuit 748 may be sterilized. In alternative embodiments, the fluid circuit 748 is sterilized before medicament concentrate is pumped in, the sterile filters 756 ensuring no contamination enters the sealed fluid circuit 748. If the fluid circuit is sterilized after filling with medicament concentrate, the sterile filters 756 on the concentrate feed inlets 759 and 760 may be omitted. In any of the embodiments, instead of welding a line to seal it, a non-reopenable clamp may be applied to the line to seal it. In other alternatives, other types of sealing may be employed. In any embodiments where a kink-type clamp is used (e.g. 772) a frangible valve may be used instead.

Note in any of the embodiments described herein, other types of tubing closures may be used. For example, frangible-seal valve-type closures may be used. An example of a frangible-seal valve is described in U.S. Pat. No. 4,586, 928. The medicament proportioning module 104 may be equipped with an actuator to open a frangible-seal valve automatically during a set-up procedure. In a method, after installing the fluid cartridge, a linear actuator aligned with a frangible-seal valve by the positioning of the cartridge, may be controlled to open the valve in response to a command from a controller. The command may follow the complete preparation for a treatment, for example and a user input to a user interface indicating that the system should begin priming in preparation for treatment.

Figure 16A:
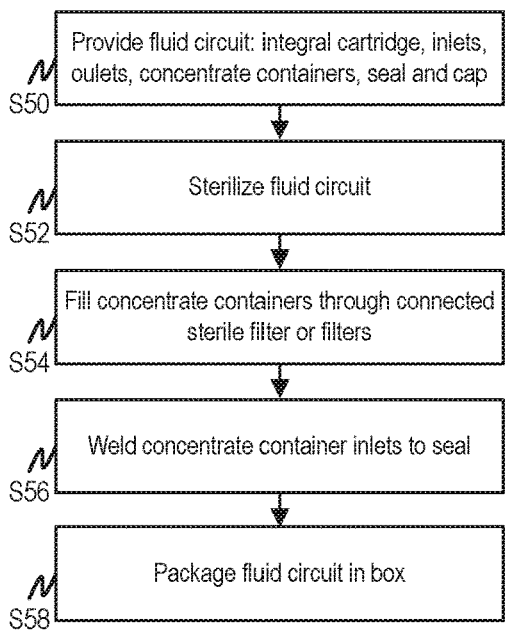
FIGS. 16A and 16B are flow charts showing methods of making the fluid circuits of FIGS. 15A and 15B, respectively, and others, according to embodiments of the disclosed subject matter.

FIG. 16A is a flow chart of a process for making the fluid circuit 748. At S50, the fluid circuit 748 is assembled by permanently welding or otherwise bonding the elements of the fluid circuit 748 together. The fluid circuit 748 may be sterilized at S52. Medicament concentrate may be pumped into the concentrate feed inlets 759 and 760 until a predefined quantity is supplied at S54. The concentrate feed inlets 759 and 760 can be welded to seal them a point therealong as indicated at 761 at S56. The complete fluid circuit with concentrate may then be packaged in a box or other container with the cartridge 770 either attached or stored within the box or other container S58.

Figure 15B:
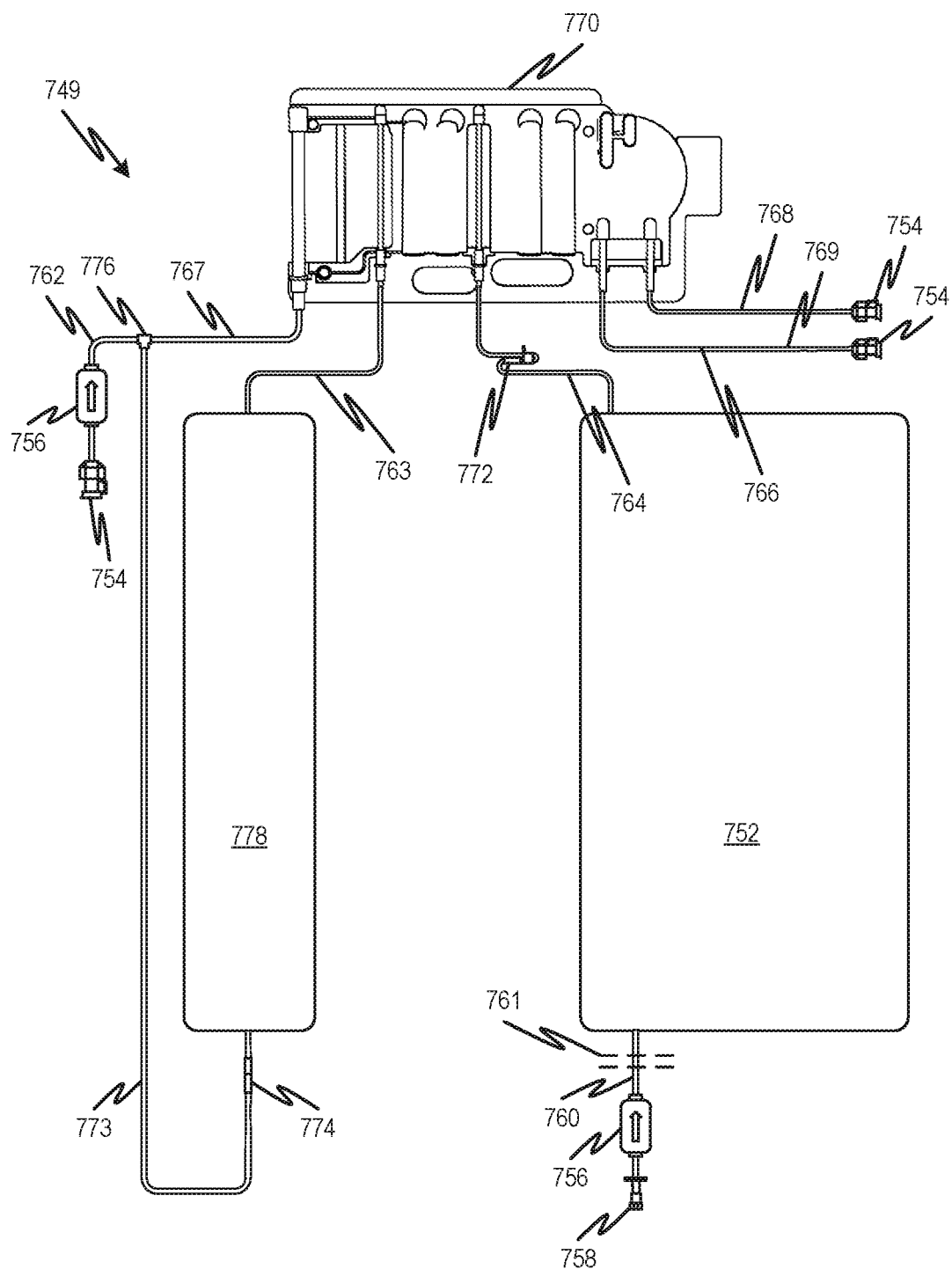

Referring now to FIG. 15B, a cartridge 770 may provide the fluid circuit elements described with reference to any of the above cartridge embodiments including concentration sensor stations, accumulator, valve clamping tube segments, and pumping tube segments which are oriented and positioned by mounting the cartridge. The cartridge 770 may also have a data carrier as described that provides data concerning characteristics of the cartridge and all the fluid circuit elements of the fluid circuit 749 indicated by reference-numeral 749, including the composition of medicament concentrates or dry medicament solute contained in the attached container 752 and cartridge 778 of a type that receives water at an inlet 480 and produces a saturated solution from dry solute stored in the cartridge. An inlet line 762 has an inline sterile filter 756 and a primary inlet 754 connectable to a source of pure water which is capped and sealed. A first medicament concentrate line 763 and a second medicament concentrate line 764 are connected to allow concentrate to be pumped into a medicament supply line in a predefined proportion with water pumped through inlet line 762. Kink-type clamps, which are described in, for example, International Publication No. WO 2007/118235 (see, for example, FIGS. 30A through 32 of said publication) seal the second medicament concentrate line 764. A junction 776 connects the water inlet 762 to water inlet line branches 767 and 773. The branch 773 leads to inlet of the cartridge 778 through a connector 774. Waste line 769 and product medicament line 768 lead out from a common medicament supply line and are capped and sealed as indicated at 754. Concentrate feed inlet 760 is provided to fill the concentrate container 752 through sterile filters 756. The entire fluid circuit may be sealed, including the kink-type clamp 772, and respective medicament supplies may be connected to connectors 758. Medicament concentrate may be pumped into the concentrate feed inlets 759 and 760 until a predefined quantity is supplied, then the concentrate feed inlets 759 and 760 can be welded to seal them a point therealong as indicated at 761. The welding can simultaneously cut off the filter 756 and 758. Then the entire fluid circuit 749 may be sterilized. In alternative embodiments, the fluid circuit 749 is sterilized before medicament concentrate is pumped in, the sterile filters 756 ensuring no contamination enters the sealed fluid circuit 749. If the fluid circuit is sterilized after filling with medicament concentrate, the sterile filters 756 on the concentrate feed inlets 760 may be omitted.

Note in any of the embodiments, a single sterilizing filter may be used to fill the concentrate containers of multiple fluid circuits like sealed fluid circuit 749. This may be done by connecting multiple fluid circuits to a single filter with a manifold. The latter may be sterilized prior to use. The fluid circuits connected to the filter and manifold may be sterilized after connection to prevent touch contamination from making the connection or the connection may be done in a sterile environment. The circuits may be filled and then sealed as 761, discussed above.

Figure 16B:
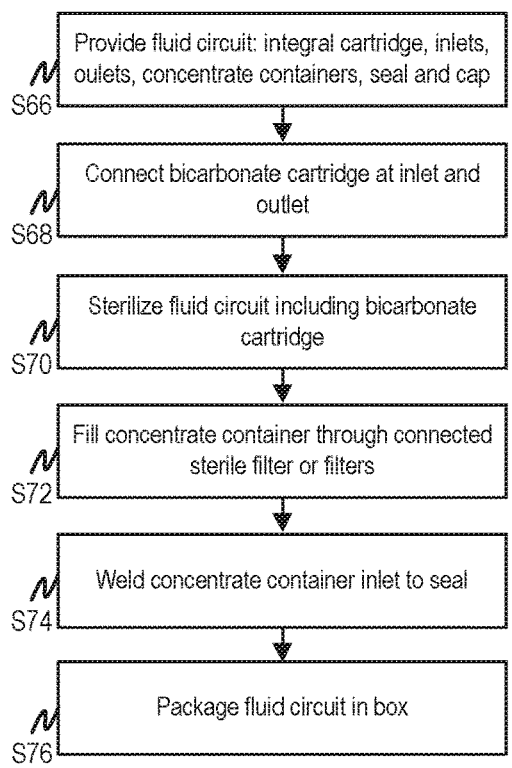

FIG. 16B is a flow chart of a process for making the fluid circuit 749. At S66, the fluid circuit 749 is assembled by permanently welding or otherwise bonding the elements of the fluid circuit 749 together. The buffer cartridge 778 may be connected to the water inlet branch 773 S68. The fluid circuit 749 may be sterilized at S70. Medicament concentrate may be pumped into the concentrate feed inlet 760 until a predefined quantity is supplied at S72. The concentrate feed inlet 760 can be welded to seal it a point therealong as indicated at 761 at S74. The complete fluid circuit 749 with concentrate may then be packaged in a box or other container with the cartridge 770 either attached or stored within the box or other container S76.

Figure 17:
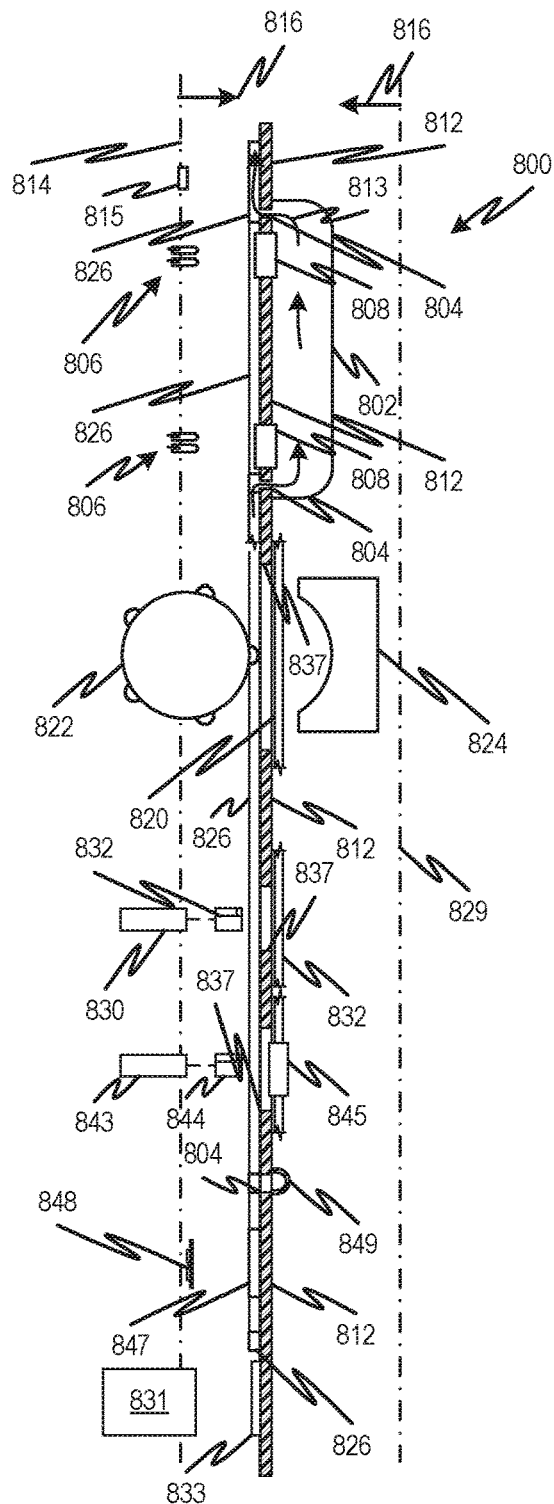
FIG. 17 shows an arrangement of elements that show how electrical, thermal, and mechanical engagement (contact) with sensor instrumentation and actuated elements can be made according to embodiments of the disclosed subject matter.

FIG. 17 shows a portion of a fluid circuit cartridge 800 to illustrate how electrical, thermal, and mechanical engagement of actuators and sensors are provided using the fluid circuit cartridge device. A fluid circuit base planar element 812, for example, injection molded plastic has molded walls that define channels 826 having a generally uniform cross section and may be covered by film by welding or adhesive. The wall extend from a base portion of the planar element forming a trough and the edges of the walls remote from the base element are then sealed with the film, fully closing the trough to form the channel. The film may be thin to minimize thermal resistance between a temperature sensor 815 (supported on a support 814) and the fluid carried by the channel 826. A channel 826 portion for engagement with temperature sensor 815 may be flattened out to reduce edge flux effects on the temperature measurement. In general, the channels 826 may be straight or curved segments that convey fluid with minimal resistance. Openings such as indicated at 804 allow the flow in the channels 826 to flow (see arrows 813) into other features such as a column channel 802 for measuring conductivity using electrodes 808 and the accumulator (not shown). The electrodes make electrical contact with contact pins 806 (which may be four in number for measuring contact resistance and for four-point measurement to minimize the effect of contact resistance on the conductance signal) also supported on an opposing planar actuator support indicated by dot-dash line 814 but which may be any type of support or supports. The temperature sensor 815 and contact pins 806 may be backed by urging elements such as springs. Pumping tube segments 820 can be clamped between a roller actuator 822 and a race 824, respectively supported on support 814 and an opposing support 829. A pinch clamp segment 832 of tubing can be positioned between clamping elements 830 supported on support 814 and clamped by a pinch clamp tubing segment. All of the engagements required are conveniently provided by moving the supports 814 and 929 in opposing directions as indicated by arrows 816 around the fluid circuit base planar element 812. Further, some of the fluid carrying features are formed by the fluid circuit base planar element 812 including the channels. Connections to the tube segments can be formed in the channel by molding as well. A tubing segment with a valve 845 such as a frangible-seal valve may be positioned to be opened at a time of set up and priming by an actuator motor 843 and actuator 844. Here the fluid circuit base planar element 812 may serve as a backstop to resist the force applied to the valve 845 or the actuator 844 may provide a clamping or scissor action that does not require an opposing support. Windows Another fluid circuit feature that can be formed in the fluid circuit base planar element 812 is a pressure sensor region 847, which may be formed similarly to the temperature channels 826. The overlying film provides a compliant surface that can apply force to a strain gauge 848 pressed into engagement with the overlying film of the pressure sensor region 847 when the 816 are positioned to engage the fluid circuit cartridge 800 elements. Openings 804 and elbows 849 (See example 863 in FIG. 18A of elbow that communicates with a concentrate pumping tube segment 864 shown in FIG. 18A and discussed relative thereto) may also be made in the fluid circuit base planar element 812 with to flow fluid from channels 826 to tubular portions such as a pinch clamp tubing segment 832, a valve 845, or pumping tube segment 820 attached at the opposite side of the fluid circuit base planar element 812.

As discussed above, the fluid circuit base planar element 812 may also support a data carrier 833 that is positioned when the cartridge is installed, to be read by a reader 831.

In embodiments, the fluid circuit base planar element 812 may be molded such that all the all the side action mold parts can be drawn in the same direction. As may be verified by inspection of elbows 863 on FIG. 18A (same features unlabeled in FIG. 18B), may be molded in the same directions as column channel 802 using a single side action in the molding process. This is disclosed clearly in FIG. 18A and discussed in connection with flow column housing element 891 which is formed as an open ended element with a sealing member 894 to close it after molding.

In embodiments, the fluid circuit cartridge 800 may position all the sensor and actuator surfaces on one side of the fluid circuit base planar element 812. This allows all the actuators and sensors and their associated wiring and circuitry to be positioned on a first side and supported by only the support 814. The opposing support 829 can be passive. In the example shown, the opposing support 829 supports only the race 824 (a member often called a "shoe"). To facilitate tight packing of the elements, some of the larger elements such as column channel 802, pinch clamp tubing segment 832, a valve 845, and pumping tube segment 820 can be attached on the opposite side. This allows the sensors and actuators to be larger than they would be able to be if these elements were on the other side. Rather, most of the first side is flat or open. This can allow the cartridge to be much smaller than otherwise possible.

Figure 18A:
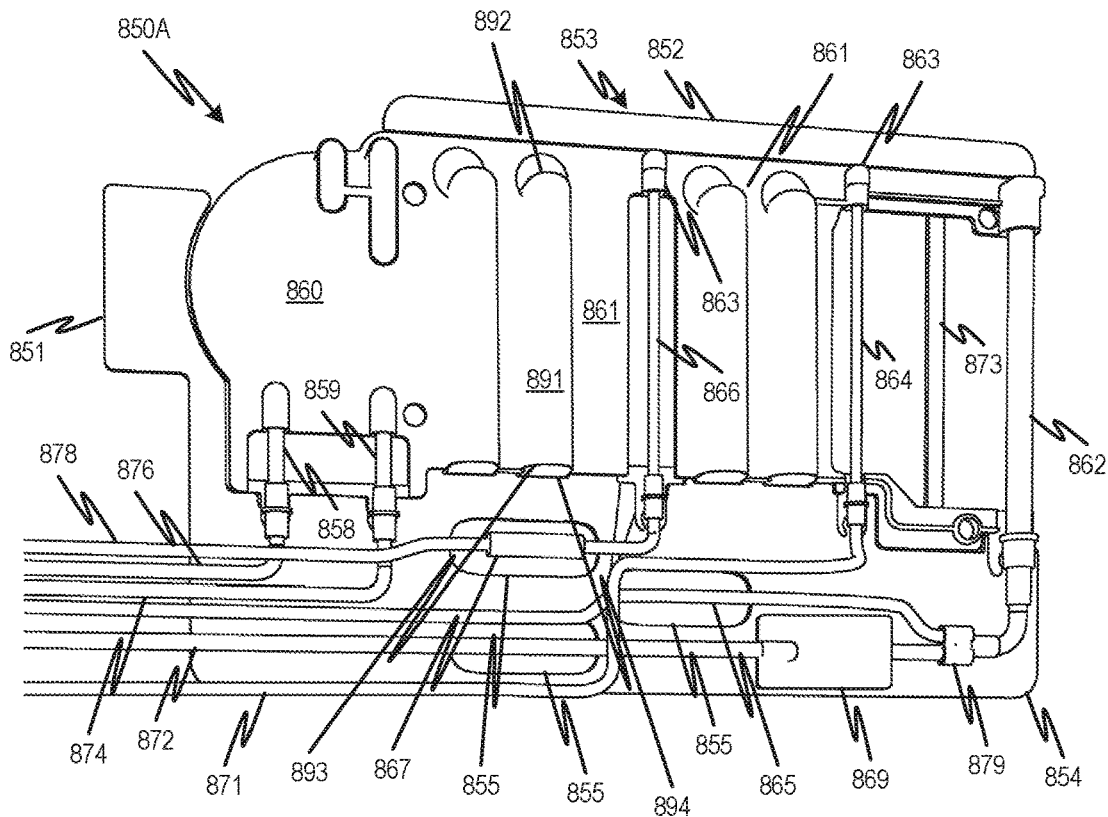
FIGS. 18A and 18B show details of fluid circuit cartridges according to embodiments of the disclosed subject matter.
Figure 18B:
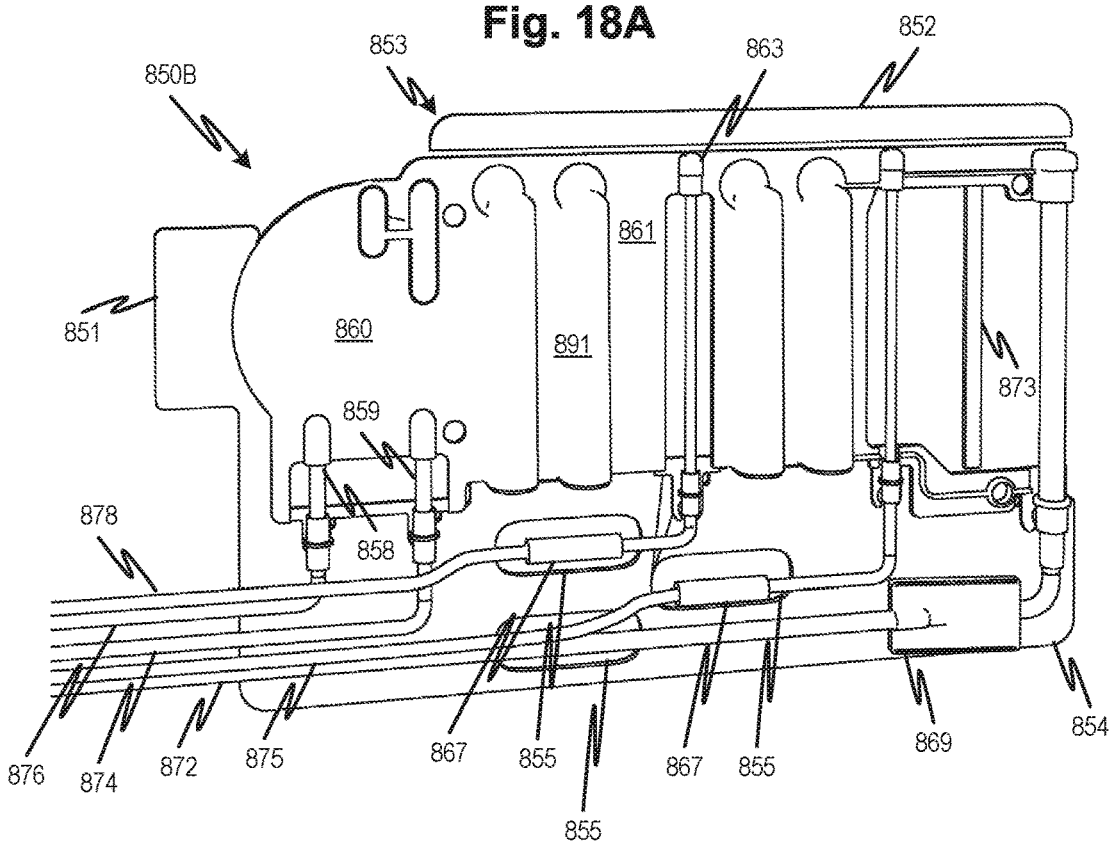

FIGS. 18A and 18B show details of fluid circuit cartridges according to embodiments of the disclosed subject matter. The fluid circuit cartridge 850A is optimized for use with a dry medicament cartridge in medicament concentrate disposable package 617 and fluid circuit cartridge 850B is optimized for use with liquid concentrates in medicament concentrate disposable package 617. A cartridge structural element 853 has a cartridge support element top edge 852, a cartridge support element lower edge 854 and a cartridge support element grip edge 851. A support strut 873 may be provided to stiffen a fluid circuit planar element 861. The cartridge support element top edge 852, cartridge support element grip edge 851, and cartridge support element lower edge 854 may be one piece attached to the fluid circuit planar element 861, or separate elements that are interattached through the fluid circuit planar element 861. The cartridge support element grip edge 851 segment of cartridge structural element 853 has an extended portion that facilitates insertion and removal of the fluid circuit cartridge 850A and 85B. Fluid circuit planar element 861 may correspond to, for example, fluid circuit planar element fluid circuit base planar element 812. An accumulator, as discussed in other embodiments, is located in the region 860 behind the viewpoint of FIG. 18A. Fluid channels (see reference-numeral 826 and attending discussion) as described above are formed in fluid circuit planar element 861 to interconnect the various elements of the fluid circuit cartridge 850A. As described elsewhere in the present application, fluid circuit cartridges such as fluid circuit cartridge 850A may have conductivity sensors with column channels, temperature measurement cells, pinch clamp segments, valve such as frangible-seal valves, pumping tube segments, electrodes, data carriers, etc. The fluid conveying elements may be interconnected by fluid channels as described with reference to reference-numeral 826.

Two concentrate pumping tube segments 866 and 864 draw concentrate through a first medicament concentrate line 878 and a second medicament concentrate line 878. The first pumping tube segment 866 and second medicament concentrate line 864 communicate with channels formed in fluid circuit planar element 861 (on the other side of fluid circuit planar element 861 but see FIG. 17 for description) via elbows 863 molded into the fluid circuit planar element 861. A frangible-seal valve 867 is openable by an actuator as discussed with reference to FIG. 17 to allow the medicament concentrate from a connected container to flow through it. See FIGS. 15A and 15B for discussion of connected medicament concentrate containers or dry solute cartridges. Fluid circuit cartridge 850B has two frangible-seal valves 867, one each for two medicament concentrate lines 878 and 875. Fluid circuit cartridge 850A may not need a frangible-seal valve 867 for the dry medicament cartridge used in the medicament concentrate disposable package 617 where dry bicarbonate powder or other dry solute is used instead of a liquid concentrate. In a method, the cartridge 850A or 850B is inserted in a receiving slot (e.g. 606 of FIG. 13C) and prior to the generation of product medicament during a setup procedure, the frangible-seal valve 867 seal is broken so that liquid medicament concentrate thereafter can be pumped. This may be done in preparation for, or to fully complete, a priming operation. Windows 855 in the cartridge structural element 853 provide access to the frangible-seal valve 867 for actuators in the receiving slot (e.g. 606) to open the frangible-seal valves 867 as well as to a pinch valve segment 865 presently discussed.

An additional pure water line 872, which has the function described of pure water line 629 of FIG. 13E, sends pure water, under control of a pinch valve segment 865. The pure water is drawn through a junction 879 connected to the pure water inlet line 871 from the water purification module 102. The pinch valve segment 865 may be controlled by a valve pinching actuator in the receiving slot (e.g., receiving slot 606). By providing the additional pure water line 872 in the cartridge 850A, the valve pinching actuator for controlling the flow in additional pure water line 872 can be conveniently positioned with respect to the pinch valve segment 865. The additional pure water line 872 has an inline sterilizing filter 869 that guards against the entry of desterilizing contaminants into the product medicament. Pumping of the pure water is accomplished by an actuator in engagement with pumping segment 862. Product medicament passes into the accumulator which opens to pinch valve segments 858 and 859 which pass product (or waste, depending on a state of the medicament proportioning module 104, through product medicament line 876 or waste line 874.

The drawings of the fluid circuit cartridge 800A, 800B and fluid circuit planar element 861 illustrate another feature that may be provided. The concentration measuring stations include flow column housing elements 891. In an alternative embodiment, which is illustrated, most of the body of each flow column housing element 891 is integrally formed with the fluid circuit planar element 861, with one closed end, using a side action molding part. The open end 893 is closed by a sealing member 894 after the formation of the fluid circuit planar element 861. This may be done to form all the flow column housing elements 891 (only one of which is labeled, but there may be four, as illustrated, and as discussed in foregoing embodiments). The features such as 863 may be formed using the same side action mold and these parts may be ganged to provide a single molding operation.

Figure 19:
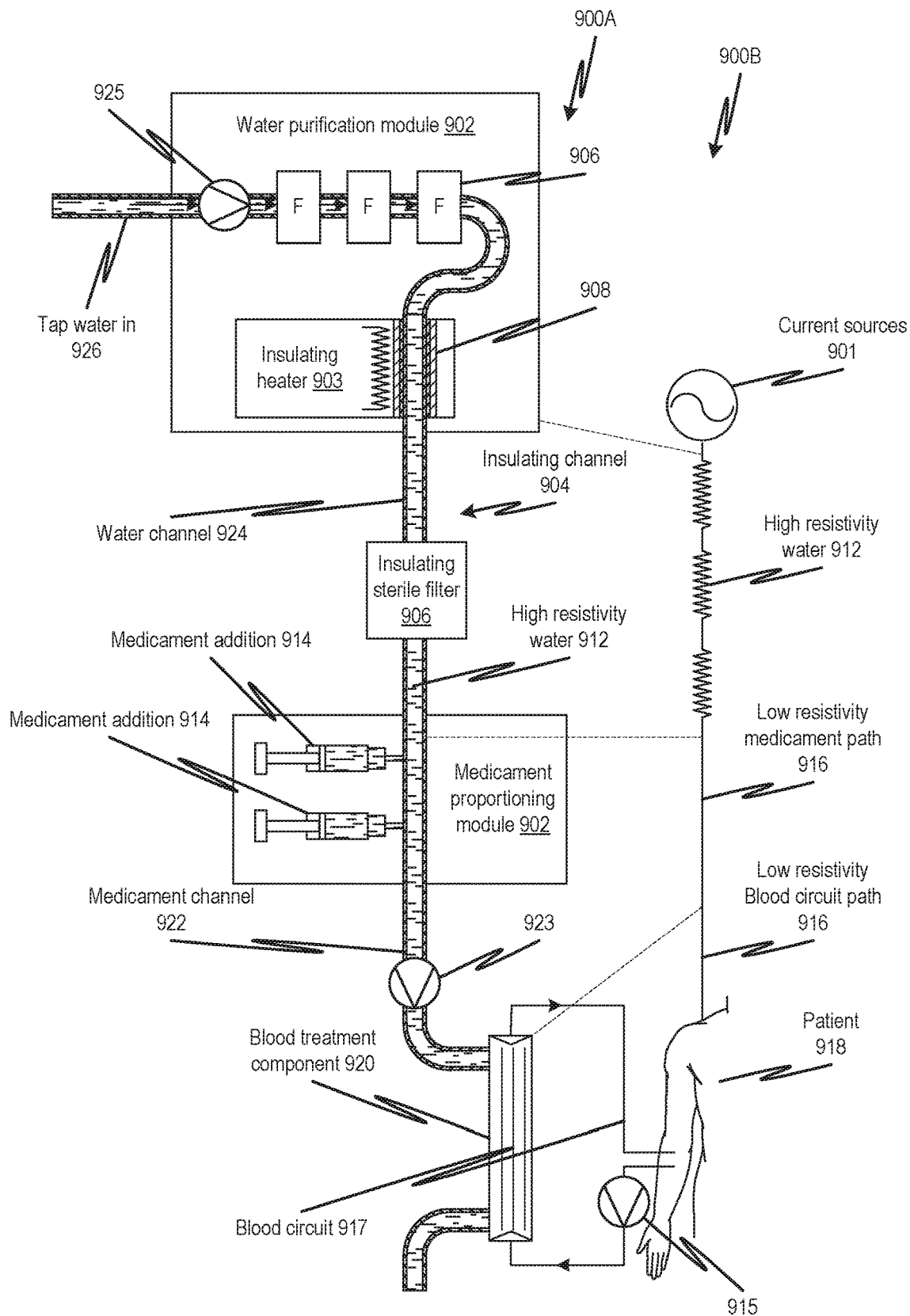
FIG. 19 shows schematically and figuratively a combined water purification, medicament proportioning and treatment system to highlight a feature by which leakage current is minimized, according to embodiments of the disclosed subject matter.

FIG. 19 shows schematically and figuratively a combined water purification, medicament proportioning and treatment system to highlight a feature by which leakage current is minimized, according to embodiments of the disclosed subject matter. A medicament supply and treatment system 900A is illustrated figuratively at 900A and schematically as an electrical circuit transferring leakage current to a patient at 900B. The medicament supply and treatment system 900A supports a blood treatment systems susceptible to leakage current from electric heater used to heat medicament due to the inherent formation of a conductive fluid path between the current sources and the patient 918. In FIG. 19, the sources are indicated collectively by the symbol 901. Many of the sources of leakage current can be capacitive and inductive sources that can generate a current in a fluid line carrying fluid of limited conductivity, such as a medicament line. An electrical heater 903 can be a particularly strong source of leakage current. In embodiments, the electric heater 903 is a variable heater under feedback control of a controller to maintain a target temperature. In embodiments, the target temperature is based on the patient properties or measurements. The temperature of fluid in thermal contact with the blood of a patient can affect the raising or lowering of the body temperature of the patient 918. In dialysis, for example, the dialysate has a high concentration of electrolytes that is pumped, by a pump 923, and circulated in direct contact (wetting contact) across the pores of the membrane of a blood treatment component 920 (in this case a dialyzer), with the blood of the patient circulating in a blood circuit 917 under the urging of a blood pump 915. Thermal contact, as well as the electrical continuity poses the problem of leakage current transfer to the patient. Note the blood treatment component 920 may be a dialyzer, hemofilter, hemodiafilter, liver dialysis filter, or the patient's peritoneal membrane as in peritoneal dialysis or other devices that cause the electrical circuit to exist. Thus, in extracorporeal blood treatments, the medicament is pumped through a device that exchanges both heat and electric current with the patient's blood.

A water purification module 902 may have a pump 925 and a controller (not shown). The water purification module 902 may have deionization filters of sufficient capacity and the pump may be controlled such that the water is purified to a level of purity exceeding a predefined resistivity. A predefined resistivity may be, for example, 1 megohm-cm. In an example embodiment, the predefined rate is 2 megohm-cms. In further examples it is 3 megohm-cms, 5 megohm-cms or up to 10 megohm-cms. Various parameters, depending on the type of water purification system can provide resistivity levels as high as the predefined resistivity. For example, reverse osmosis can be used for achieving such high resistivity although deionization resin beds may be more practical for such levels of purity. Here the drawing illustrates multiple stages of filters 906 used for water purification and these may be as described elsewhere herein in connection with water purification modules or other types of water purification systems. The purified water with the predefined resistivity or higher passes through a heater 903. Note in embodiments, the heating may occur at an earlier stage such that the resistivity of the water is not as high as the predefined resistivity or higher. A feature of the present embodiment is that there exists a high resistivity water stream 912 (exceeding the predefined resistivity) between the heater 906 and other current sources 901 and the remainder of the fluid circuit including a low resistivity medicament path 916 and a low resistivity blood circuit path 916. Thus, to provide heat, the system 900A interposes a high resistivity fluid path between current sources including the heater 903 and the patient 918. The heater 903 is regulated to control the temperature of the patient. This may be done by controlling the temperature of the medicament circulating in the blood treatment component 920.

In embodiments of the above system, medicament concentrate is added to the water of a predefined resistivity to make the medicament that is ultimately used for treatment. Medicament concentrate 914 is injected in the high resistivity water forming medicament and flows through a medicament channel 922. The medicament then flows through the blood treatment component 920 forming an electrical circuit with the patient as discussed. Medicament concentrate addition may be of any suitable form including as described with reference to the embodiments disclosed herein.

A beneficial feature of the system 900A may be for the fluid channels to be of electrically insulating material such as polyvinyl chloride or silicone to ensure the high resistivity fluid channel is not undermined by conduction through the channel materials. The high resistivity water channel 924 length and cross-sectional area (local and varying over the length thereof or constant) may be selected to ensure a predefined leakage current target is met. The electric heater 903 may be of a type that places the product water in direct contact with permanent non-disposable surfaces of a flow channel in the electric heater 903. The electric heater may contain double-insulated rod-type heaters or other devices for minimizing the level or risk of undesired electric current in the fluid being heated. The flow channel in the heater may be electrically insulated. A sterile filter 906 may be placed in the interconnection between the heater and the medicament proportioning module 902. The sterile filter 906 may be multiple stages. In the above embodiments, the use of a sterile filter at the outlet of the water purification module 102 ensures that sterile water flows from the water purification module 102 and the risk of touch contamination caused by interconnecting the disposable fluid circuit for the medicament proportioning module 104 is eliminated by permanently affixing a sterile filter in the inlet of the disposable fluid circuit.

A controller for the heater 903 may be adapted for controlling the electric heater 903 responsively to a measured temperature and/or a temperature target selected for maintaining the body temperature of the human patient 918. The controller of the electric heater 903 may compensate for a heat load caused by the addition of medicament concentrate to the flow of product purified water. This heat load arises if the medicament concentrate is a lower temperature than the target temperature for the medicament used in treatment.

A length of the water channel and a resistivity of the product water may be sufficient to ensure that said electric heater produces less than 50 microamperes of leakage current through said continuous fluid path to said patient access. As a result, heat required to maintain body temperature of a patient being treated by the blood treatment benefits from an electrically insulating convective flow of pure water used for the generation of medicament used in the treatment.

Figure 20A:
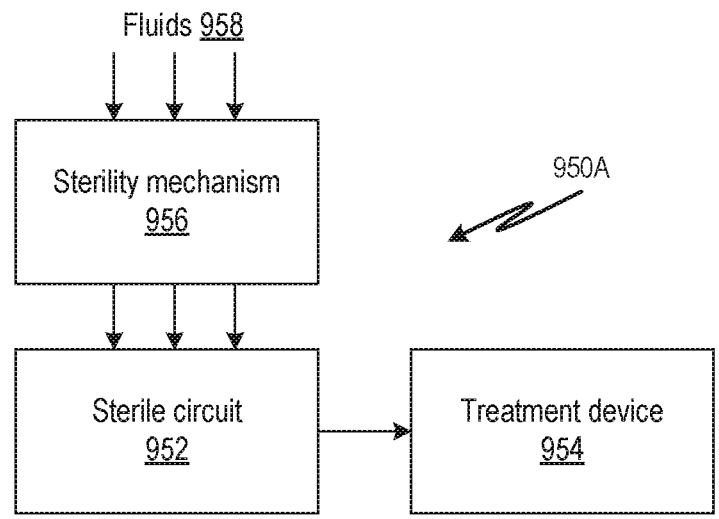
FIGS. 20A through 20D illustrate embodiments of fluid proportioning systems that illustrate features of the disclosed embodiment, according to embodiments of the disclosed subject matter.

FIG. 20A shows a medicament proportioning system 950A that provides a medicament mixture using a sterile circuit 952 that can be used for preparing medicament for multiple treatments by a treatment device 954. The sterility of the sterile circuit 952 permits the sterile circuit 952 to be used multiple times (at least two, for example) spaced apart by a period of hours or days without the risk of a growth of bacteria within the sterile circuit causing a risk to a patient being treated by treatment device 954. To provide the function, the sterile circuit 952 must be sterile before use and remain sterile during and between treatments. The function of the sterile circuit 952 includes transferring fluids, and may include mixing fluid components, as well as taking property measurements, providing pumping and flow rate control and other functions as required. The treatment device 954 is one that may require a sterile medicament. According to embodiments, mechanisms for ensuring sterility may include a sterilization process or the provision of a replacement sterile circuit 952 that has been previously sterilized, such as a disposable fluid circuit as described with reference to various embodiments described herein. In embodiments, the sterile circuit 952 may be subjected to a sterilization process to make it initially sterile and then some sterility mechanism 956 ensures that the sterility helps to maintain the sterile condition of the sterile circuit 956 while providing enough fluid (one or more fluids 958) for multiple treatments. The sterility mechanism 956 may be embodied in several ways, as exemplified by the further embodiments shown in FIGS. 20B to 20D. Note, the embodiments of FIGS. 20B, 20C, and 20D are examples of the embodiment of FIG. 20A.

Figure 20B:
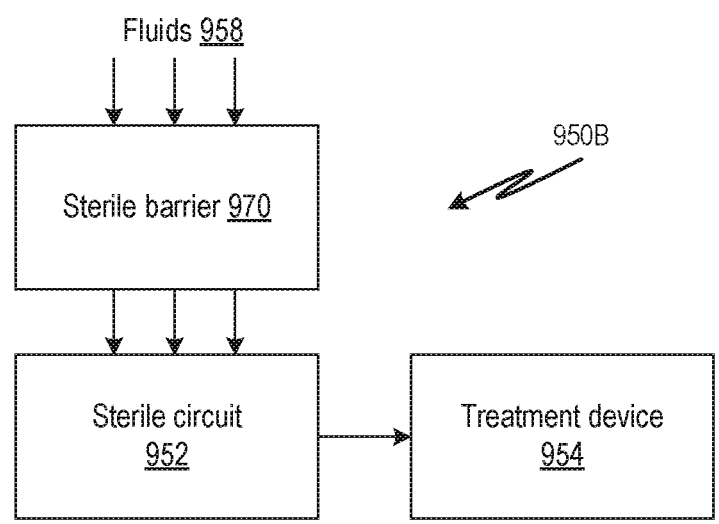
Figure 20C:
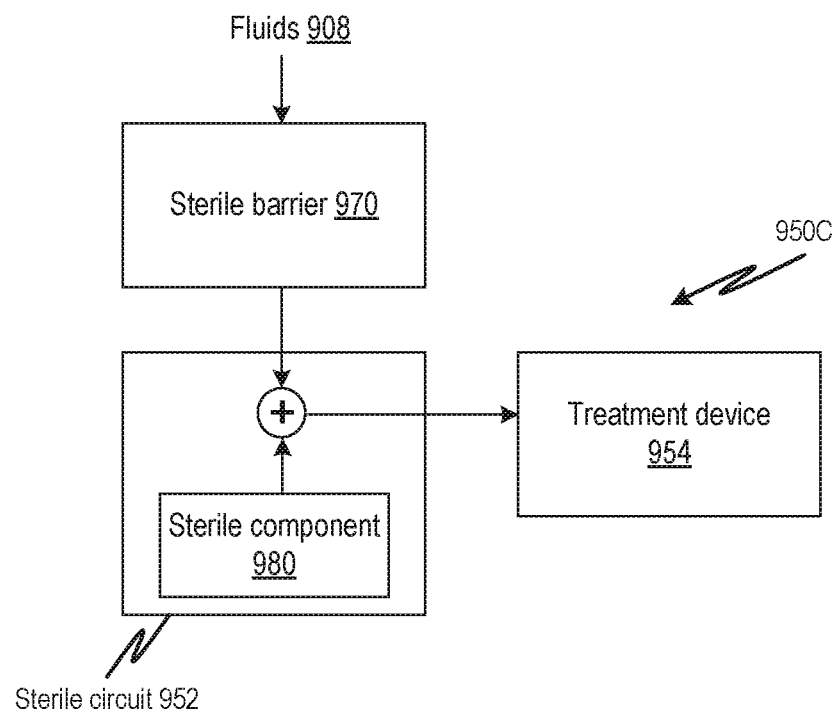
Figure 20D:
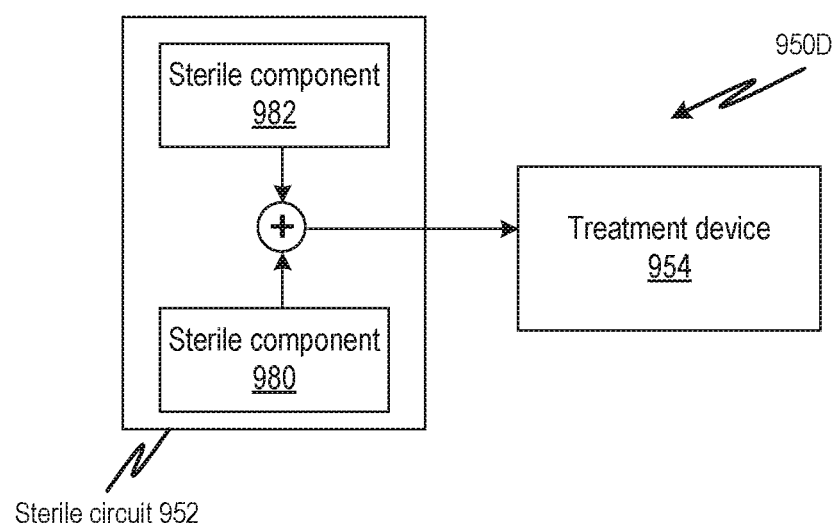

Referring to FIG. 20B, an example of a sterility mechanism is a sterile barrier 970. The sterile barrier 970 includes a fluid impermeable fluid circuit and one or more sterile filters through which all fluids required for the multiple treatments is/are passed. One or more of the fluids 958 may be transferred in real time during consumption into the sterile circuit 952, or transferred and stored at some time prior to treatment and thereafter consumed. The sterile barrier 970 may be combined with other sterility mechanism 956 embodiments, for example a sterile component 980 as in FIG. 20C where the sterile component 980 is a fluid which has been sterilized by some means and fluidly connected to the sterile circuit 952 such that an impermeable barrier (e.g., fluid channel) connects it to the sterile circuit 952. Sterile component 980 may be permanently connected to the sterile circuit 952 such that intrusion of contaminants is prevented. FIG. 20C shows a medicament preparation system 950C with a sterile barrier 970 that is used in conjunction with a sterile component 980 and conforms to the example embodiments in which pure water 908 (which may include other fluids) is supplied with a sterile barrier 970 in place, the sterile barrier may include flowing water and other fluid through a sterilizing filter. Another sterile component 980 is provided as part of the sterile circuit 932 and may be pre-sterilized medicament concentrate, for example, as described in embodiments herein. The sterile component 980 may be pre-attached to the sterile circuit 932 by fluid lines as in embodiments described herein or may be held in a capsule of a cassette or connected in any suitable manner so as to be subject to the sterile guarantee of the sterile barrier 970. FIG. 20D shows an embodiment of a medicament preparation system 950D in which all the sterile components 982, 980 are pre-connected to the sterile circuit 953.

Figure 21:
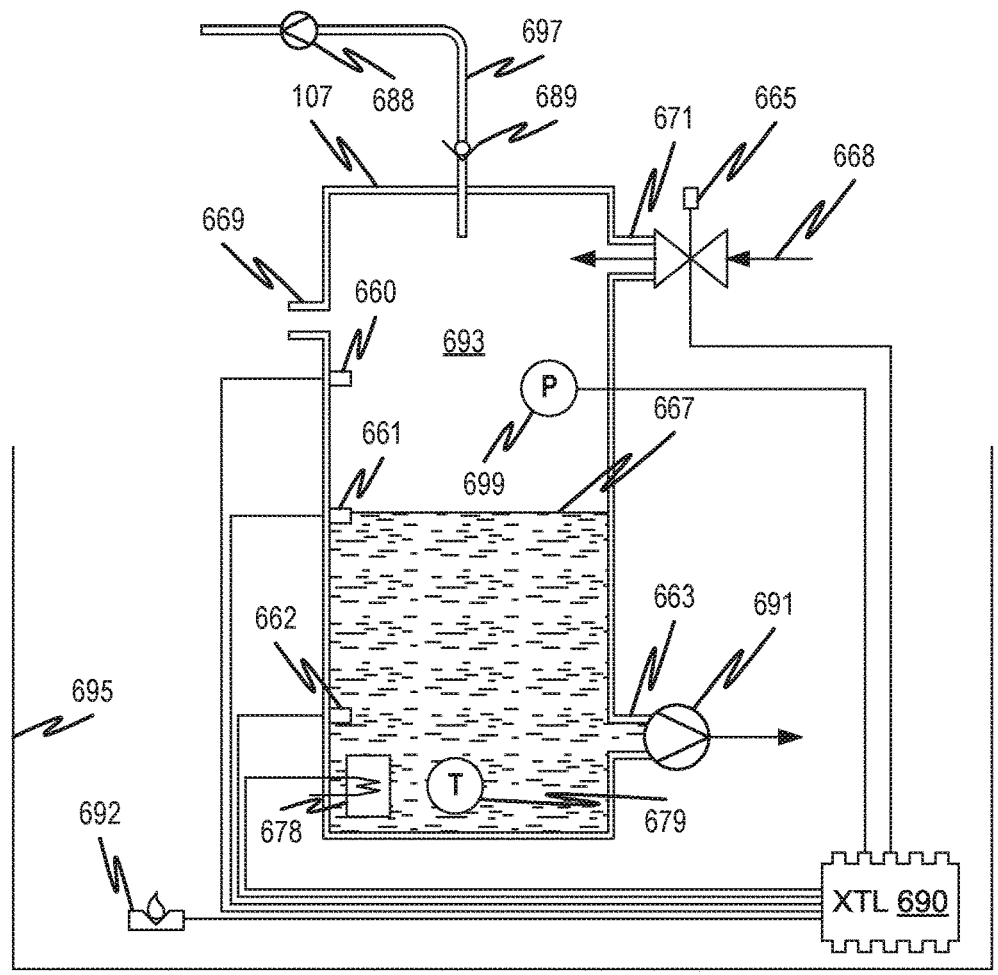
FIG. 21 shows an air break according to embodiments of the disclosed subject matter.

Referring now to FIG. 21, an air break 107 ensures safe connection to a water mains supply and provides the protection of a backflow preventer while avoiding the disadvantageous requirement of inspection and testing. The air break 107 may be included at an inlet of any of the water purification module 102 or medicament preparation system embodiments disclosed above and variants suggested by the present disclosure. See also, for example, FIGS. 1, 2, 4, 8A, 8B, and 22. Note that the air break 107 may be placed at any point in the water system effective to protect against undesirable backflow into the system or as required by local or national plumbing codes or other legal or regulatory requirements. In an example embodiment, the air break is placed in the tap water inlet line of a water purification module 102 and downstream of features such as inlet shutoff valve, pressure regulator, inlet pressure sensor, a sediment filter. Other components may be included upstream or downstream of the air break 107.

A water inlet 671 may receive water 668 delivered by mains pressure under control of a control valve 665 which may be controlled by a controller 690. The controller 690 may be independent, dedicated to control of a water purification module 102 or one that controls an integrated medicament preparation system or integrated treatment system. The controller may receive level signals from water level indicators 660, 661, 662. Although high 660, middle 661, and low 662 level indicators are shown, other numbers of level indicators may be provided. The controller maintains the level of water 667 within a predefined range (i.e., within deadband=control goal achieved) or such that a predefined level 667 is continuously pursued (i.e., specific level estimate=control goal achieved). The level indicators 660, 661, 662 may be optical, wet-detection sensors, floats, or any other type of level detector. In embodiments, the controller prevents the starvation of flow through an outlet 663, as demanded by a pump 691 which may be part of a water purification module 102 or a medicament preparation system or any other system. That is the controller maintains a level 667 sufficient to allow water to be demanded as required through the outlet 663 by permitting water through the control valve 665 until a level 667 below an overflow outlet 669, is reached. If a reverse pressure arises, pressure in the internal volume 693 cannot rise due to the free flow through the overflow outlet 669.

To permit the level 667 of water in internal volume 693 to rise, air can be vented through an air vent line 697 which may have a check valve 689 to permit flow only out from the internal volume 693. The pressure in the internal volume may be detected by a pressure sensor 699 and if a positive pressure arises, for example due to an abnormal condition such as a blockage of the air vent line 697 and/or the overflow outlet 669, the controller 690 may output an error or prevent the operation of a pump 691 demanding water. A resistivity sensor 678 may be provided to detect abnormal water resistivity and the controller 690 may output an error indication signal in response, for example a warning on a user interface and/or a command signal to terminate the use of the water which may cause one or more pumps to stop operating and an error indication to be displayed or otherwise output. A wetness detector 692 may be placed under the air break 107 within a housing 695 to output an indication of water leak or overflow through overflow outlet 669. The wetness detector may also apply an output signal to the controller 690 to cause the latter to output an error indication and to take the steps of preventing further operation until the fault is cleared.

Figure 22:
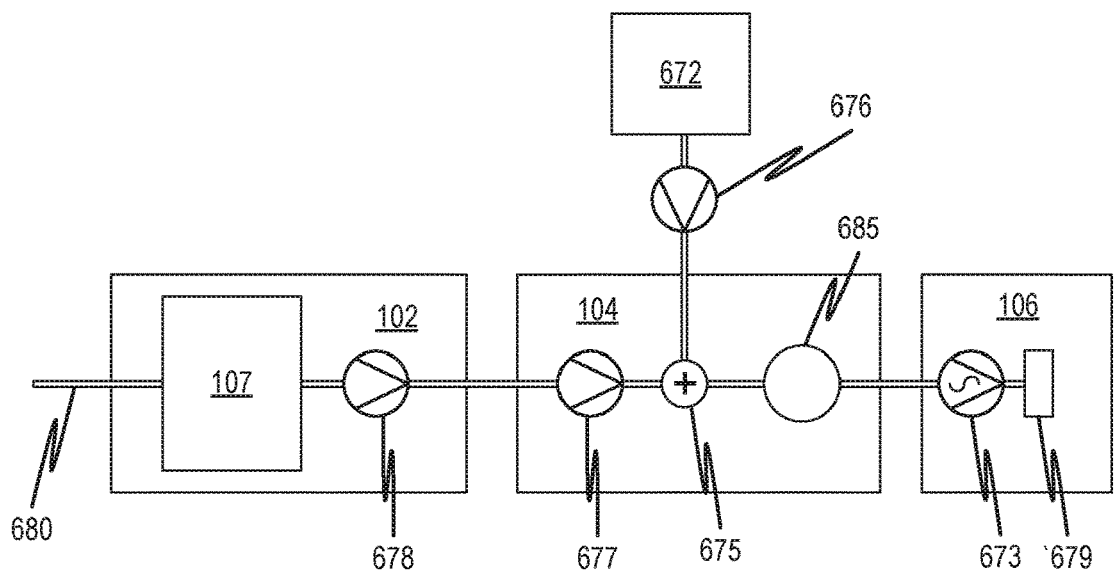
FIG. 22 shows a treatment system with an air break for purposes of discussing its function in a medicament preparation system or a treatment system, according to embodiments of the disclosed subject matter.

FIG. 22 illustrates the advantages of the air break 107 in system embodiments such as described in connection with principal embodiments. Tap water enters a water inlet 680 which flows into the air break 107, which may include all the features described with reference to FIG. 21 and any others identified herein such that the air break level 667 is maintained and error conditions are detected. A pump 678 of a water purification module 102 draws water from the air break as required to supply a medicament proportioning module 104 which is able to, by virtue of the support of on-demand draw capability of the air break 107, control pumps 677 and one or more pump(s) 676 for medicament concentrate 672 for accurate mixing. Further, the pressure of the fluid may be consistent and unaffected by pressure variations from the mains supply 668. That is, the air break 107 prevents the transmission of pressure fluctuations downstream from the outlet 663 from, for example, the mains supply 668. For example, pumps 677 and one or more pump(s) 676 for medicament concentrate 672 may provide the most accurate mixing when they are operated at a constant or slowly varying rate and with a constant inlet pressure. Fluids are combined in a junction 675. The cycler 106 also may draw fluid at time-varying rates using a respective pumping device 673, such as a flow balancing mechanism, to provide medicament to a treatment component 679 using the flow-rate matching capability of the accumulator 685 as described with respect to embodiments thereof.

In variations of the embodiment of FIG. 13A, 13B, the anion resin bed 658, cation resin bed 659, carbon filter 640, and mixed bed 641 may be separated so that they reside at the corners of the housing 601 with the cartridge receiving module 618, medicament concentrate disposable package 617, and medicament module 161 in the central volume between them. Other variations are also possible and the disclosed subject matter is not limited to these particular arrangements.

Figure 23A:
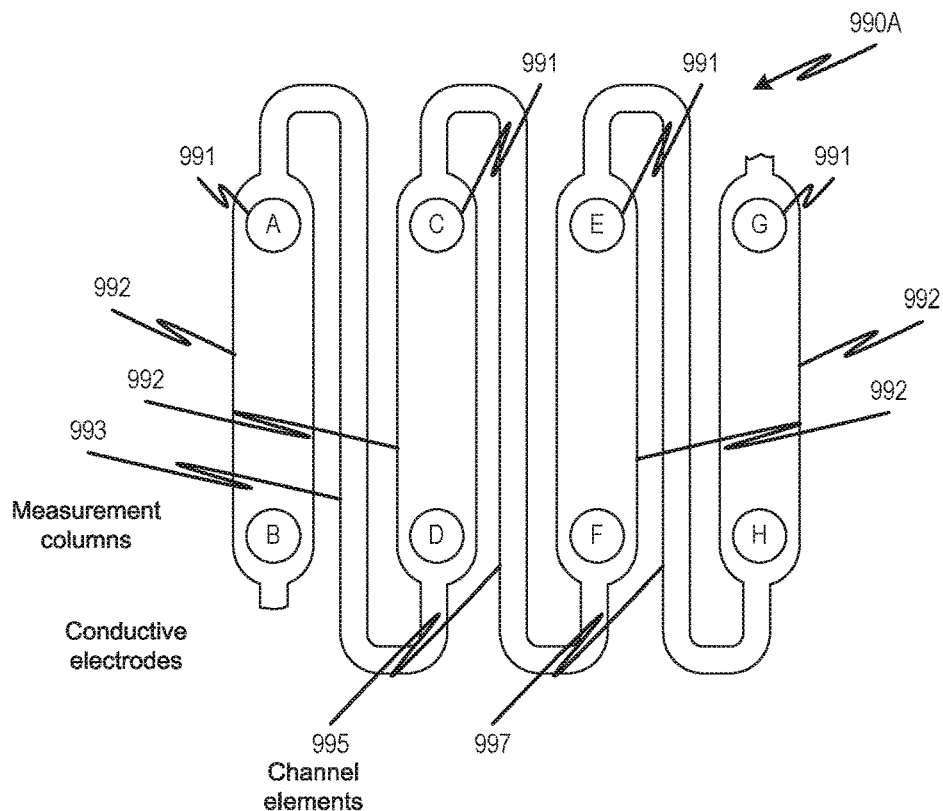
FIGS. 23A and 23B show embodiments of a conductivity measurement component that may be used with any cartridge embodiments, or substituted with equivalent conductivity measurement components thereof in any of the embodiments disclosed or claimed.
Figure 23B:
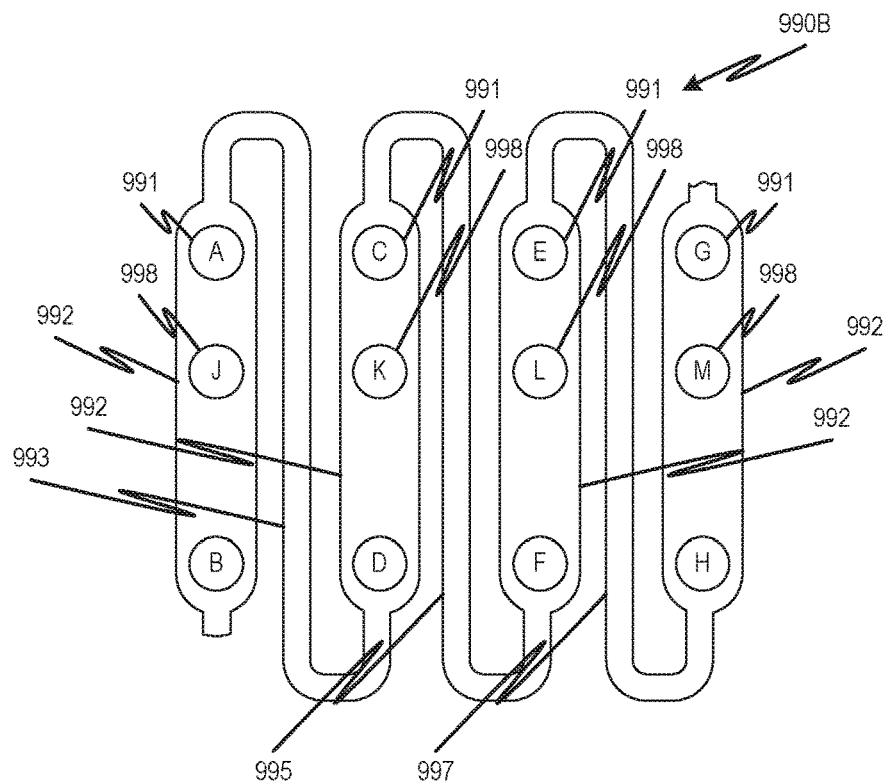

Referring now to FIG. 23A, as in the fluid circuit 533, conductivity may be measured using a series concentration measurement modules that are connected in series or series/parallel as described with reference to FIG. 10. In the present embodiment, which may be substituted into any of the foregoing or following embodiments, conductivity is measured based on multiple paths as well as the fluid column in a respective measurement column, such as columns 992. A fluid flows through columns 992 which are joined by channel elements 995. Additional channel elements may be included such as to inject concentrates or diluents as described with reference to FIG. 10. In the latter embodiment, the resistance of fluid to the flow of current was obtained between conductive electrodes at either end of a respective measurement column. In embodiments, additional measurements using the same conductive electrodes may be made. In FIG. 23A, conductive electrodes 991 are labeled A through H. Contact resistance on the dry side of each electrode may be made between current contacts and voltage sense contacts which are provided and used according to the well-known four-point resistance measurement technique. In the present embodiment, resistance is measured between multiple pairs that share a given conductive electrode 991. Not all the conductive electrodes are indicated by a reference numeral to avoid clutter but each is labeled with a respective letter. Here, conductive electrode pair A-B is used for a resistance measurement through a respective fluid column 992. Further, conductive electrode pairs A-D and A-C are also used for a resistance measurement through a respective fluid column 992 plus channel element 993 and a respective fluid column 992 plus channel element 993 plus fluid column 992, which form respective longer fluid paths. The same may be done with conductive electrode pairs B-C, B-D, and C-D. Given known properties of the respective channels, which may be stored explicitly or tacitly (e.g., by way of a formula or look up table), the fluid conductivity can be derived from these resistance measurements. Further measurement columns 992, receiving the same fluid, may be added to provide additional fluid paths between additional conductive electrode pairs, such as A-E, A-F, E-F, E-H and so on. Additional conductive electrodes may also be added to each measurement column such as the conductive electrodes labeled J through M in FIG. 23B. In the latter example, additional conductive electrode pairs can be used for additional measurements of fluid conductivity, for example, A-J and A-K. Not all combinations of conductive electrodes are enumerated herein as it is straightforward to make a comprehensive list of conductive electrode pairs that can be formed with any such a conductivity measurement system based on a desired number and allocation of conductive electrodes. As in the embodiment of FIG. 23A, branch lines that admit diluent or concentrate may be included at any point, of course with diminution of the number of combinations of conducting electrodes that may be available for conductivity measurement.

In the foregoing embodiments, by forming multiple electrical conduction paths through interconnected conductivity cells, using additional conductive electrodes for each measurement column, and/or by measuring across fluid paths between measurement columns, additional measurements of the same fluid conductivity or measurements that include additional variables such as the electrode "wet-side resistance," i.e., the resistance between an electrode and the fluid can be better gauged, at least for purposes of determining the reliability of a conductivity measurement. Where a resistance measurement appears faulty due to an unexpected resistance associated with an electrode, the multiple paths provide multiple equations to solve for the unknown additional resistance correction term that is used to compensate the resistance. The controller may perform these calculations automatically.

In any embodiments, an accumulator, such as accumulator 502, can be omitted and an inline pressure sensor alone may be employed thereby relying on the compliance of tubing for providing smooth pressure signals for control. The elimination or reduction in size of the accumulator may be an optimization variable. Reducing this volume may speed the synchronization process.

In any of the embodiments, including the claims, two medicament concentrates may be diluted by a medicament proportioning system or module. In these arrangements where there is concentration detection, the buffer may be diluted first and then the acid may be diluted to form a dialysate or replacement fluid product. This has benefits in that the concentration signal of the acid is stronger than that of the dilute buffer thereby causing more sensitive concentration detection.

In any of the embodiments including cycler 106, the latter may be replaced by any medicament consuming device or article such as a storage container for product medicament or a peritoneal dialysis cycler. In any of the foregoing embodiments, a pressure sensor 127 may be positioned within at an inlet or outlet of the accumulator to allow the controller to control flow through the accumulator. This may in effect be a mechanical pressure control signal from the device that demands fluid from any of the disclosed medicament proportioning system, medicament proportioning module, or other device. See discussion of pressure transducer 155 for relevant context and function for an example.

In any of the foregoing embodiments, the flow channels and pumping mechanisms may be replaced with any equivalent elements adapted for fluid conveyance. They may be selected to handle flow rates in the range, in respective systems or in a single system to provide medicament to a consuming device at a rate of 25 through 400 ml/min. Any of the embodiments may be modified to provide an intermediate storage of medicament if the instantaneous demand of a consuming device exceeds the selected maximum generation rate of medicament. The medicament formed by the foregoing embodiments may be dialysate or replacement fluid for use any type of renal replacement therapy system, for example, peritoneal dialysis, hemodialysis, liver dialysis, and hemofiltration. The consuming appliance for any of the above systems may be a storage container to generate medicament to support a vacationing patient. It will be observed that in the embodiments disclosed, spent fluid (e.g., spent dialysate) from an attached cycler can be disposed of such that it never enters the medicament proportioning module 104 or any element upstream of the cycler. In embodiments, the cycler 106 is configured to prevent a backflow of fluid into the medicament proportioning module 104. For example, a check valve may be provided in-line between the medicament proportioning module 104 and cycler 106 for such a purpose.

By providing ultrapure water that has been reliably sterilized and guarded against touch contamination, it is possible to ensure against risk for a primed medicament proportioning module 104 to treat multiple patients within a long time period, in an exemplary embodiment, up to 24 hours apart. Also the medicament proportioning module 104 may be primed and readied for a treatment to occur many hours, for example up to 24 hours, from the time of set-up.

In any of the foregoing cartridge embodiments, the cartridge may include a data carrier (e.g., 519) which may be or incorporate devices such as a bar code, RFID, smart chip, memory chip, or other device that includes data related to the concentrate or dry compound attached thereto for generation of medicament. Thus, by installing the cartridge, details related to the attached medicament concentrate can be communicated to the controller of the medicament proportioning module 104 or medicament preparation system (e.g., 600). For example, the data carrier may include data responsive to an expiration date, whether the fluid circuit attached to the cartridge has been used prior to the most recent installation, how much fluid has been generated from it, how long since it was first primed with fluid, the makeup of the concentrates attached to the fluid circuit. The pre-attachment of the concentrates to the circuit cartridge (e.g., 500, cartridge 406 and others), when the cartridge includes a data carrier that refers to information about the concentrates and other components of the fluid circuit, provides the two benefits (1) of allowing the cartridge, which may be of a types that is registered in a specific position and therefore convenient to allow for reading of data on the data carrier by means of a reader and (2) preventing contamination of fluid circuit by avoiding the need to make a new connection to combine the concentrate containers with the other elements of the fluid circuit. The precise positioning of the cartridge, for engagement of actuators and sensors therewith, can ensure predictable and reliable interaction between the data carrier and a reader co-located with the sensors and actuators. Also, the cartridge may be of a type that is convenient and relatively small, making handling easier for less able-bodied users, since the cartridge may be tethered to the heavier concentrate containers which may be placed in separate positions and, in embodiments, with less accuracy. In embodiments, a receiving support for the concentrate containers may be low down next to the floor while the cartridge receiving position may be located above that receiving support for the concentrate containers. See for example the configuration shown in FIG. 13A where the medicament concentrate disposable package 617, which may contain the medicament concentrates as discussed with reference to the various embodiments, is positioned on a low shelf. A slide out tray (on roller rails for example) may be provided (not shown) to allow the medicament concentrate disposable package 617 to rested thereon so that the medicament concentrate disposable package 617 can be pushed into position without sliding. Similarly for the ultrafilter module 616 and any other similar components.

The controller of the medicament proportioning module 104 or medicament preparation system 700 or any other of the modules or systems herein described may have an identifier of one or more patients correlated with the medicament that is prescribed for that patient. The data included in the data carrier may be used by the controller to confirm that the correct fluid circuit is loaded by verifying the circuit cartridge data carrier. The control of the proportioning by pumps may be regulated to conform to the required medicament product. When the cycler is attached to the medicament preparation system (e.g., 600) or module 104, a signal communication between the controller of the medicament proportioning module 104 or medicament preparation system 700 and the attached consuming device, such as cycler 106 (e.g., see lines 124) may contain data indicating the type of medicament required, an identification of the patient, a prescription, or other information that may be correlated by any of the controller with the parameters of the connected fluid circuit as indicated on the data carrier of the cartridge and a signal indicating permitted or non-permitted component installation generated by any of the controllers. Such a signal may cause the generation of an output indication or prevent further operation of the equipment, if a non-permitted component installation is performed.

The data carrier may also establish expected reading ranges for measured concentration of medicament concentrate indicated by concentration measurement module 535A-535D. These data may be used to control the dilution rate of the respective medicament concentrates using feedback control from the concentration measurement modules or conductivity/temperature sensors in accord with the respective embodiments. Note that as used herein, a combination of a conductivity sensor and a temperature sensor may also be referred to as a concentration measurement module for example the combinations shown in FIGS. 8A and 8B. The data carrier may include calibration data or data used for ensuring the accuracy of measurement using the cartridge or other parts of the fluid circuit. For example, in embodiments, the data carrier may communicate to the controller the cell constants or dimensions of the conductivity sensors of the cartridge for use in computing conductivity and thereby concentration. The data relating to disposables attached to and used with the system (e.g., water purification module 102 and medicament proportioning module 104) may be logged in a maintenance and/or procedure log for troubleshooting and service. The latter may be output by the user interface by maintenance, treatment, or service personnel. Solute concentration is used to set target conductivity values. Reading in solute concentration allows addition of new catalogue numbers without requiring a software update. [not clear what this means]

The replaceable components used for water purification may include replaceable tagged components with data carriers permitting various similar functions as the data carriers 519 and other relevant to the cartridge. Generally, the function of the water purification module 102 (or the water purifying function of an integrated medicament preparation system), is to purify water to a same standard. However the performance characteristics of the replaceable tagged components may vary. The control of the water purification module 102 may include determining whether the replaceable tagged component is correct for the particular water purification module 102. In embodiments the controller may predict a total amount of fluid that may be processed before replacement of certain replaceable tagged components is appropriate.

Referring now to FIG. 23A, a conductivity measurement portion 990A of a fluid circuit includes multiple measurement columns 992 connected in series by channel elements 993, 995, 997. Additional junctions may be provided as described in reference to FIG. 10. Four pairs of conductive electrodes A-B, C-D, E-F, G-H are shown but the number of columns and number of electrodes can vary. As described with reference to FIG. 10, each conductive electrode pair can be used for an independent measurement of a conductivity of fluid (or fluids) flowing therethrough. In the present embodiments, resistance is measured across other pairs of conductive electrodes than the pairs, A-B, for example, at opposite ends of each measurement column 992. For example, the resistance between conductive electrodes A-C and A-D as well as B-C and B-D may also be measured. With predefined channel properties between these pairs of conductive electrodes stored in a controller (or effectively stored in a lookup table or formula for computing fluid conductivity, multiple equations with multiple unknowns that include the contact resistances of the electrical contacts used to measure conductivity can be obtained.

In any of the foregoing embodiments, fluid circuits may include inline chambers (accumulators) to reduce water hammer due to interaction between interconnected peristaltic pumps. Additional (extra—more than required) lengths of tubing may also be included the same purpose. Also, tubing diameters of pump tubing segments may be selected to minimize interaction issues which may reduce accuracy or cause breakage of circuit elements.

According to first embodiments, the disclosed subject matter includes a fluid circuit for preparation of a medicament for renal replacement therapy. A flexible bag contains acid concentrate connected for flow communication, through a first pumping tube segment, to a medicament supply line that has been capped and sterile-sealed at an outlet end thereof. A bicarbonate cartridge contains dry bicarbonate buffer compound. The bicarbonate cartridge is of a type that admits water in a cartridge inlet thereby forming a saturated bicarbonate solution which is received at a cartridge outlet. The cartridge outlet is connected for flow communication, through a second pumping tube segment, to the medicament supply line. A water inlet line is capped and sterile-sealed and connected for flow communication, through a third pumping tube segment, to the medicament supply line and further connected for flow communication to the bicarbonate cartridge inlet. The first, second, and third pumping tube segments are supported by a circuit cartridge which orients, aligns, and exposes for access the first, second, and third pumping tube segments with respective actuators of a predefined medicament preparation device. The circuit cartridge contains a first concentration sensor station positioned in the medicament supply line downstream of a first junction where a first of the first and second pumping tube segments connects to the medicament supply line. The circuit cartridge contains a second concentration sensor station positioned in the medicament supply line downstream of both the first junction and a second junction where a second of the first and second pumping tube segments connects to the medicament supply line.

The entire fluid circuit is sterile. In embodiments, the entire fluid circuit is sealed and sterilized as a unit so that there is no need to connect the medicament containers to the rest of the fluid circuit and the only opportunities for ingress of contaminants into the fluid circuit is through a sterile filter, which prevents ingress of contaminating bacteria. Since other connections are outlets only, for example for product dilute medicament and waste, the pumping ensures that bacteria cannot otherwise enter.

Variations of the first embodiments may be provided to form additional first embodiments in which the circuit cartridge includes a fluid accumulator fluidly coupled between the water inlet line and the medicament supply line outlet end that includes a pressure-regulating urging element that biases a flexible wall of the accumulator such that transient changes of fluid pressure therein cause expansion of the volume of the accumulator. Variations of the first embodiments may be provided to form additional first embodiments in which the fluid circuit is packaged with a box such that the circuit cartridge can be detached or removed from the box while leaving the flexible bag and bicarbonate cartridge intact therein with lengths of connecting lines between the circuit cartridge and the box, thereby permitting the circuit cartridge to be installed in a position remote form a position where the box is installed. Variations of the first embodiments may be provided to form additional first embodiments in which the fluid circuit is packaged within a box such that the circuit cartridge can be removed from the box while leaving the flexible bag and bicarbonate cartridge intact therein with lengths of connecting lines between the circuit cartridge and the box, thereby permitting the circuit cartridge to be installed in a position remote form a position where the box is installed.

Further variations of the first embodiments may be provided to form additional first embodiments in which the fluid circuit is attached to a box in such a way that the circuit cartridge can be detached from the box while leaving the flexible bag and bicarbonate cartridge intact therein with lengths of connecting lines between the circuit cartridge and the box, thereby permitting the circuit cartridge to be installed in a position remote form a position where the box is installed. The Variations of the first embodiments may be provided to form additional first embodiments in which the box is principally of cardboard. Variations of the first embodiments may be provided to form additional first embodiments in which each of the concentration sensor stations includes a liquid conductivity sensor and temperature sensor portions. Variations of the first embodiments may be provided to form additional first embodiments in which the temperature sensor portion includes a flow chamber with a flat surface to permit a temperature sensor to be placed against the flat surface of a predefined sensor of the predefined medicament preparation device. Variations of the first embodiments may be provided to form additional first embodiments in which each of the concentration stations includes, connected in series, two independent conductivity sensors and two independent temperature sensor portions. Variations of the first embodiments may be provided to form additional first embodiments in which the medicament supply line includes a waste outlet branch that is in direct fluid communication with the accumulator, the waste outlet line is capped and sterile-sealed, the medicament supply line outlet line and waste outlet branches has pinching portions supported in an open section of the circuit cartridge to permit access by pinching actuators.

According to second embodiments, the disclosed subject matter includes a fluid circuit for preparation of a medicament for renal replacement therapy. A first container contains acid concentrate connected for flow communication, through a first pumping tube segment, to a medicament supply line that has been capped and sterile-sealed at an outlet end thereof.

A second container contains a buffer concentrate connected for flow communication, through a second pumping tube segment, to the medicament supply line. A water inlet line is capped and sterile-sealed and connected for flow communication, through a third pumping tube segment, to the medicament supply line. The first, second, and third pumping tube segments are supported by a circuit cartridge which orients, aligns, and exposes for access the first, second, and third pumping tube segments with respective actuators of a predefined medicament preparation device. The circuit cartridge contains a first concentration sensor station positioned in the medicament supply line downstream of a first junction where a first of the first and second pumping tube segments connects to the medicament supply line. The circuit cartridge contains a second concentration sensor station positioned in the medicament supply line downstream of both the first junction and a second junction where a second of the first and second pumping tube segments connects to the medicament supply line.

The entire fluid circuit is sterile. In embodiments, the entire fluid circuit is sealed and sterilized as a unit so that there is no need to connect the medicament containers to the rest of the fluid circuit and the only opportunities for ingress of contaminants into the fluid circuit is through a sterile filter, which prevents ingress of contaminating bacteria. Since other connections are outlets only, for example for product dilute medicament and waste, the pumping ensures that bacteria cannot otherwise enter.

Variations of the second embodiments may be provided to form additional second embodiments in which the circuit cartridge includes a fluid accumulator fluidly coupled between the water inlet line and the medicament supply line outlet end that includes a pressure-regulating urging element that biases a flexible wall of the accumulator such that transient changes of fluid pressure therein cause expansion of the volume of the accumulator. Variations of the second embodiments may be provided to form additional second embodiments in which the fluid circuit is packaged with a box such that the circuit cartridge can be detached or removed from the box while leaving the first and second containers intact therein with lengths of connecting lines between the circuit cartridge and the box, thereby permitting the circuit cartridge to be installed in a position remote form a position where the box is installed. Variations of the second embodiments may be provided to form additional second embodiments in which the fluid circuit is packaged within a box such that the circuit cartridge can be removed from the box while leaving the first and second containers intact therein with lengths of connecting lines between the circuit cartridge and the box, thereby permitting the circuit cartridge to be installed in a position remote form a position where the box is installed.

Further variations of the second embodiments may be provided to form additional second embodiments in which the fluid circuit is attached to a box in such a way that the circuit cartridge can be detached from the box while leaving the first and second containers intact therein with lengths of connecting lines between the circuit cartridge and the box, thereby permitting the circuit cartridge to be installed in a position remote form a position where the box is installed.

The Variations of the second embodiments may be provided to form additional second embodiments in which the box is principally of cardboard. Variations of the second embodiments may be provided to form additional second embodiments in which each of the concentration sensor stations includes a liquid conductivity sensor and temperature sensor portions. Variations of the second embodiments may be provided to form additional second embodiments in which the temperature sensor portion includes a flow chamber with a flat surface to permit a temperature sensor to be placed against the flat surface of a predefined sensor of the predefined medicament preparation device. Variations of the second embodiments may be provided to form additional second embodiments in which each of the concentration stations includes, connected in series, two independent conductivity sensors and two independent temperature sensor portions. Variations of the second embodiments may be provided to form additional second embodiments in which the medicament supply line includes a waste outlet branch that is in direct fluid communication with the accumulator, the waste outlet line is capped and sterile-sealed, the medicament supply line outlet line and waste outlet branches has pinching portions supported in an open section of the circuit cartridge to permit access by pinching actuators.

According to third embodiments, the disclosed subject matter includes a fluid handling system. A multiple stage water filtration module has a fluid circuit with a pump positioned in the fluid circuit to pump water therethrough, an inlet, an outlet, and at least two filtration stages each has a replaceable filter component. A controller has a signal output and a water quality sensor connected to fluid circuit and positioned to detect the quality of water upstream of the at least two filtration stages and output a water quality signal. The controller further has a signal output and further is connected to control the pump. the controller includes a processor and a data store, the processor is programmed to generate cumulative load data, stored in the data store and indicative of a cumulative amount of filterable material in water processed through the fluid circuit up to a point of time prior to a change of at least one of the replaceable filter components, wherein the cumulative load data is responsive to multiple samples of the water quality signal. The controller generating a control or data output signal responsive to the cumulative load data for use in replacing the at least one of the replaceable filter components.

Further variations of the third embodiments may be provided to form additional third embodiments in which the water quality sensor includes a water conductivity sensor. Further variations of the third embodiments may be provided to form additional third embodiments in which the controller prevents operation of the pump until the at least one of the replaceable filter components is changed. Further variations of the third embodiments may be provided to form additional third embodiments in which the at least one of the replaceable filter components includes a deionization filter. Further variations of the third embodiments may be provided to form additional third embodiments in which the at least one of the replaceable filter components includes an activated carbon filter. Further variations of the third embodiments may be provided to form additional third embodiments in which the control or data output signal includes data indicating an amount of time before the at least one of the replaceable filter components is exhausted. Further variations of the third embodiments may be provided to form additional third embodiments in which the control or data output signal includes a user interface output indicating that the at least one of the replaceable filter components should be changed. Further variations of the third embodiments may be provided to form additional third embodiments in which the cumulative load data is responsive to a total volume of water processed by the at least one of the replaceable filter components. Further variations of the third embodiments may be provided to form additional third embodiments in which the total volume is indicated by the operating time or number of cycles of the pump.

According to fourth embodiments, the disclosed subject matter includes a medicament preparation system. A fluid management element has a controller, pump actuators, sensors, a valve actuator, a data reader, and a cartridge support for a fluid handling cartridge. The fluid management element has a support for a medicament concentrate container positioned remotely from the cartridge support. The data reader is located adjacent the cartridge support so as to permit the reading of a data carrier on a cartridge positioned to engage the pump actuators, sensors, and valve actuator. The controller is configured to store data read by the data reader indicating a characteristic of concentrate in the medicament concentrate container and to control the fluid management element responsively thereto.

Further variations of the fourth embodiments may be provided to form additional fourth embodiments that include a replaceable fluid circuit with a medicament concentrate container and a fluid handling cartridge, the fluid handling cartridge has pumping tube segments sized and shaped to engage the pump actuators and a data carrier positioned to convey data to the data reader. Further variations of the fourth embodiments may be provided to form additional fourth embodiments in which the data carrier includes a bar code. Further variations of the fourth embodiments may be provided to form additional fourth embodiments in which the fluid handling cartridge and the medicament concentrate container are connected by one or more tubes which allow the fluid handling cartridge to be installed in the fluid management element remotely from the fluid handling cartridge. The Further variations of the fourth embodiments may be provided to form additional fourth embodiments in which the controller includes a processor programmed to compare the characteristics of concentrate with predefined characteristic data stored by the controller and to output data responsive to the comparison, the controller controlling the fluid management element responsively to a result of the comparison. Further variations of the fourth embodiments may be provided to form additional fourth embodiments in which the controller includes a user interface and a processor programmed to compare the characteristics of concentrate with predefined characteristic data stored by the controller and to output data responsive to the comparison, the processor outputting data to the user interface responsive to a result of the comparison, includes indicting a correct or incorrect type of medicament concentrate in the medicament concentrate container. Further variations of the fourth embodiments may be provided to form additional fourth embodiments in which the concentrate container includes an acid and a buffer. Further variations of the fourth embodiments may be provided to form additional fourth embodiments in which the data carrier includes an RFID. Further variations of the fourth embodiments may be provided to form additional fourth embodiments in which the fluid handling cartridge includes temperature sensor portions that are aligned with temperature sensors when the cartridge is with respect to the cartridge such that the data reader is able to read data from the data carrier. Further variations of the fourth embodiments may be provided to form additional fourth embodiments in which the fluid handling cartridge is removably housed within in the medicament concentrate container. Further variations of the fourth embodiments may be provided to form additional fourth embodiments in which the fluid handling cartridge is removably attached to the medicament concentrate container.

According to fifth embodiments, the disclosed subject matter includes a medicament preparation system. A medicament generation system has actuators and sensors positioned and shaped to interface a fluid circuit. The fluid circuit includes a first container contains acid concentrate connected for flow communication, through a first pumping tube segment, to a medicament supply line that has been capped and sterile-sealed at an outlet end thereof; a second container contains a buffer concentrate connected for flow communication, through a second pumping tube segment, to the medicament supply line; and a water inlet line of the medicament supply line, capped and sterile-sealed, connected for flow communication, through a third pumping tube segment, to the medicament supply line. A sterile filter in the water inlet line is positioned to filter all water entering the medicament supply line. The fluid circuit is disposable replaceable component and provided as a sterile sealed unit. A water purification plant is connectable to the inlet, the water purification plant has a sterile filter positioned in an outlet thereof, which is connectable to the inlet, has a pore size that ensures sterility of the water entering the water inlet line. A controller has a processor configured to calculate a permissible life for utilization thereof responsively to at least one of a volume of fluid passing through the medicament supply line, a volume of water passing through the water inlet, and a length of time since water first flowed through the water inlet.

Further variations of the fifth embodiments may be provided to form additional fifth embodiments in which the first, second, and third pumping tube segments are supported by a circuit cartridge which orients, aligns, and exposes for access the first, second, and third pumping tube segments with respective actuators of a predefined medicament preparation device. Further variations of the fifth embodiments may be provided to form additional fifth embodiments in which the circuit cartridge contains a first concentration sensor station positioned in the medicament supply line downstream of a first junction where a first of the first and second pumping tube segments connects to the medicament supply line. Further variations of the fifth embodiments may be provided to form additional fifth embodiments in which the circuit cartridge contains a second concentration sensor station positioned in the medicament supply line downstream of both the first junction and a second junction where a second of the first and second pumping tube segments connects to the medicament supply line. Further variations of the fifth embodiments may be provided to form additional fifth embodiments in which the circuit cartridge contains a second concentration sensor station positioned in the medicament supply line downstream of both the first junction and a second junction where a second of the first and second pumping tube segments connects to the medicament supply line.

Further variations of the fifth embodiments may be provided to form additional fifth embodiments in which the circuit cartridge includes a fluid accumulator fluidly coupled between the water inlet line and the medicament supply line outlet end that includes a pressure-regulating urging element that biases a flexible wall of the accumulator such that transient changes of fluid pressure therein cause expansion of the volume of the accumulator. Further variations of the fifth embodiments may be provided to form additional fifth embodiments in which the fluid circuit is packaged with a box such that the circuit cartridge can be detached or removed from the box while leaving the first and second containers therein with lengths of connecting lines between the circuit cartridge and the box, thereby permitting the circuit cartridge to be installed in a position remote form a position where the box is installed. Further variations of the fifth embodiments may be provided to form additional fifth embodiments in which the fluid circuit is packaged within a box such that the circuit cartridge can be removed from the box while leaving the first and second containers therein with lengths of connecting lines between the circuit cartridge and the box, thereby permitting the circuit cartridge to be installed in a position remote form a position where the box is installed. Further variations of the fifth embodiments may be provided to form additional fifth embodiments in which the fluid circuit is attached to a box in such a way that the circuit cartridge can be detached from the box while leaving the first and second containers therein with lengths of connecting lines between the circuit cartridge and the box, thereby permitting the circuit cartridge to be installed in a position remote form a position where the box is installed.

Still further variations of the fifth embodiments may be provided to form additional fifth embodiments in which the box is principally of cardboard. Further variations of the fifth embodiments may be provided to form additional fifth embodiments in which each of the concentration sensor stations includes a liquid conductivity sensor and temperature sensor portions. Further variations of the fifth embodiments may be provided to form additional fifth embodiments in which the temperature sensor portion includes a flow chamber with a flat surface to permit a temperature sensor to be placed against the flat surface of a predefined sensor of the predefined medicament preparation device. Further variations of the fifth embodiments may be provided to form additional fifth embodiments in which each of the concentration stations includes, connected in series, two independent conductivity sensors and two independent temperature sensor portions. Further variations of the fifth embodiments may be provided to form additional fifth embodiments in which the medicament supply line includes a waste outlet branch that is in direct fluid communication with the accumulator, the waste outlet line is capped and sterile-sealed, the medicament supply line outlet line and waste outlet branches has pinching portions supported in an open section of the circuit cartridge to permit access by pinching actuators.

According to sixth embodiments, the disclosed subject matter includes a medicament preparation system. A water purification module and a medicament proportioning module are housed together in a single housing of generally cubic shape with a maximum dimension of less than 0.8 m. The water purification module has a carbon filter, a two stage deionization filter, the first stage has separate cation and anion beds. A second stage has a mixed cation-anion bed, each of the carbon filter. The cation and anion beds and the mixed cation-anion bed is in four respective cylindrical containers whose lengths are within 80% of the maximum dimension and receivable with their respective axes vertically aligned in respective support bays located with a pair of each of the four on, and accessible from, an opposite face of the housing. An ultraviolet filter, a heater, a sediment filter, and an air break occupying a volume between the two pairs of cylindrical containers. Adjacent to and to the side of the volume, or within the volume, is a control module stacked atop a replaceable component receiving space. The replaceable component receiving space is open to one of the faces and housing a medicament concentrate container. The control module has actuators and sensors and a receiving opening sized for a predefined fluid circuit cartridge with which the pumping actuators and sensors engage and a user interface facing the one of the faces. The controller is programmed to control pumping actuators to mix water from the water purification module with concentrate from a medicament concentrate container in a prescribed ratio to generate a product medicament.

Variations of the sixth embodiments may be provided to form additional sixth embodiments having a fluid circuit that includes a medicament concentrate and a fluid circuit cartridge interconnected by a length of tubing that permits the cartridge to be inserted in the receiving opening and the medicament concentrate to be inserted in the replaceable component receiving space without connecting or disconnecting. The fluid circuit is a product of a process according to which the fluid circuit cartridge and medicament concentrate have been interconnected and sealed from the external environment and thereafter sterilized as a unit. Variations of the sixth embodiments may be provided to form additional sixth embodiments in which the medicament concentrate is stored within a first container containing acid concentrate and a second container containing a buffer concentrate, the first container is connected for flow communication, through a first pumping tube segment, to a medicament supply line that has been capped and sterile-sealed at an outlet end thereof and the second container is connected for flow communication, through a second pumping tube segment, to the medicament supply line. Variations of the sixth embodiments may be provided to form additional sixth embodiments in which the fluid circuit further includes a water inlet line connected for flow communication, through a third pumping tube segment, to the medicament supply line. Variations of the sixth embodiments may be provided to form additional sixth embodiments in which the fluid circuit cartridge contains a first concentration sensor station positioned in the medicament supply line downstream of a first junction where a first of the first and second pumping tube segments connects to the medicament supply line. Variations of the sixth embodiments may be provided to form additional sixth embodiments in which the fluid circuit cartridge containing a second concentration sensor station positioned in the medicament supply line downstream of both the first junction and a second junction where a second of the first and second pumping tube segments connects to the medicament supply line. Variations of the sixth embodiments may be provided to form additional sixth embodiments in which the fluid circuit cartridge includes a fluid accumulator fluidly coupled between the water inlet line and the medicament supply line outlet end that includes a pressure-regulating urging element that biases a flexible wall of the accumulator such that transient changes of fluid pressure therein cause expansion of the volume of the accumulator. Variations of the sixth embodiments may be provided to form additional sixth embodiments in which the fluid circuit is packaged within a box such that the fluid circuit cartridge can be removed from the box while leaving the first and second containers therein with lengths of connecting lines between the fluid circuit cartridge and the box. Variations of the sixth embodiments may be provided to form additional sixth embodiments in which the fluid circuit is attached to a box in such a way that the circuit cartridge can be detached from the box while leaving the first and second containers therein with lengths of connecting lines between the fluid circuit cartridge and the box. Variations of the sixth embodiments may be provided to form additional sixth embodiments in which each of the concentration stations includes, connected in series, two independent conductivity sensors and two independent temperature sensor portions.

According to seventh embodiments, the disclosed subject matter includes a medicament preparation system. A fluid circuit cartridge has a product medicament output port and a first pumping tube segment connectable to a pure water supply and the product medicament output port. Respective first and second concentrate containers are connected by second and third pumping tube segments to the medicament output port at respective first and second junctions. A first concentration measurement sensor station positioned a flow path of the fluid circuit cartridge between the first and second junctions. A second concentration measurement station is positioned in the flow path of the fluid circuit cartridge between the second junction and the product medicament output port. A controller is programmed to calculate iteratively a concentration of the first concentrate and water from a signal generated by the first concentration measurement station and to regulate a one or both of a first pumping actuator engaged with the first pumping tube segment and a second pumping actuator engaged with the pump second pumping tube segment responsively to the concentration of the first concentrate and water. The controller is programmed to calculate iteratively a concentration of the second concentrate and the first concentrate and water from a signal generated by the second concentration measurement station and to regulate at least two of the first, second pumping actuators and a third pumping actuator engaged with the third pumping tube segment responsively to the concentration of the first and second concentrates and water.

According to eighth embodiments, the disclosed subject matter includes a fluid circuit. A planar member has a pattern of uniform fluid channels formed therein, has a water inlet and generally uniform cross-section, and defining a product solution channel with multiple concentration measurement stations therealong, each following a respective one of junctions at which respective solutes are injected into the product solution channel. Each concentration measurement station including an inlet opening in the planar member defining a passage between a portion of the uniform fluid channels and an expanded fluid flow column. The column channel has electrodes spaced apart along the column. Each concentration measurement station further including an outlet opening in the planar member defining a passage between a first portion of the uniform fluid channels and the expanded fluid flow column. The inlet and outlet openings are at opposite ends of the fluid flow column. The outlet opening leading from the fluid flow column into an expanded section of the fluid channels has a flat face covered by a film, and the outlet opening is at an edge of the expanded section. A return opening opposite the outlet opening leading to a second portion of the uniform fluid channels downstream from the first portion. The electrodes has flat external contact surfaces that are parallel to the flat face such that electrical contacts and a temperature probe can be brought into thermal and electrical contact by moving the fluid circuit in a direction that is perpendicular to the flat face and the external contact surfaces relative to electrical contacts and a temperature sensor until thermal and electrical contact is made.

Variations of the eighth embodiments may be provided to form additional eighth embodiments in which the concentration measurement stations are arranged pairs to permit redundant concentration measurement of a flow following each of the junctions.

Variations of the eighth embodiments may be provided to form additional eighth embodiments in which the junctions are connected to medicament concentrate containers. Variations of the eighth embodiments may be provided to form additional eighth embodiments in which the junctions are connected to medicament concentrate containers containing concentrate, the fluid circuit is a product of a process that includes filling the concentrate containers with medicament concentrates of different compounds, sealing the fluid circuit from the external environment, sterilizing the filled and sealed fluid circuit, and packaging it as sealed sterilized unit for storage or delivery. Variations of the eighth embodiments may be provided to form additional eighth embodiments in which the process further includes filling the concentrate containers through one or more sterile filters attached to containers through a fill line and welding the fill line shut to seal them. Variations of the eighth embodiments may be provided to form additional eighth embodiments in which one of the junctions is connected to medicament concentrate container containing concentrate and the other is connected to a dry buffer cartridge outlet, an inlet of the dry buffer cartridge is connected to the water inlet, the fluid circuit is a product of a process that includes filling the concentrate containers with medicament concentrates of different compounds, sealing the fluid circuit from the external environment, sterilizing the filled and sealed fluid circuit, and packaging it as sealed sterilized unit for storage or delivery.

According to ninth embodiments, the disclosed subject matter includes a medicament preparation system. A housing contains a water purification module that includes multiple filtration stages. A medicament proportioning module is connected to receive purified product water generated by the water purification module and to dilute medicament concentrate in predefined proportions to generate a predefined medicament at a medicament product outlet. The housing has outwardly-facing receiving bays for filter media containers corresponding respectively to the multiple filtration stages. The housing has housing fluid connectors for connecting to the containers and the filter media containers has container connectors. Each filter media container has a guide engagement portion that fit into respective guides of the housing to force the each filter media container into an orientation and vertical position that aligns the housing and container fluid connectors.

Variations of the ninth embodiments may be provided to form additional ninth embodiments in which the filter media containers contain, respectively, carbon filtration and separated-bed and mixed bed deionization filter beds. Variations of the ninth embodiments may be provided to form additional ninth embodiments in which the receiving bays have recessed receiving support fixtures arranged to permit the bottom of each of the filter media containers to be inserted in the receiving support fixtures first and tilted to a position where the guide engagement portion fit into the respective guides of the housing. Variations of the ninth embodiments may be provided to form additional ninth embodiments in which the housing connectors have urging devices that urge the container connectors away from them. Variations of the ninth embodiments may be provided to form additional ninth embodiments that include a water quality sensor positioned to detect the quality of water received by the water purification module and a programmable controller programmed to output a limit signal used to limit the amount of water processed through the water purification module responsively to historical data responsive to the water quality indication over time and data indicating characteristics of media of the filter media containers. Variations of the ninth embodiments may be provided to form additional ninth embodiments in which the controller is programmed to limit the amount of water processed by controlling a pump responsively to the limit signal. Variations of the ninth embodiments may be provided to form additional ninth embodiments in which the controller is programmed to limit the amount of water processed by outputting an error indication on a user interface responsively to the limit signal. Variations of the ninth embodiments may be provided to form additional ninth embodiments that include a first water quality sensor positioned to detect the quality of water received by the water purification module and a second water quality sensor positioned to detect the quality of water processed by the water purification module, and a programmable controller programmed to output a limit signal used to limit the amount of water processed through the water purification module responsively to historical data responsive to the water quality indication over time and data indicating characteristics of media of the filter media containers. Variations of the ninth embodiments may be provided to form additional ninth embodiments in which the controller is programmed to limit the amount of water processed by controlling a pump responsively to the limit signal. Variations of the ninth embodiments may be provided to form additional ninth embodiments in which the controller is programmed to limit the amount of water processed by outputting an error indication on a user interface responsively to the limit signal. Variations of the ninth embodiments may be provided to form additional ninth embodiments in which the characteristics include data indicating whether the media have been used prior to installation thereof on the water purification module. Variations of the ninth embodiments may be provided to form additional ninth embodiments in which the characteristics include data indicating whether the media have ever been exhausted prior to installation thereof on the water purification module. Variations of the ninth embodiments may be provided to form additional ninth embodiments that include a data reader that reads data from data carriers installed on the filter media containers wherein the characteristics include data from the data carriers indicating whether the media have ever been exhausted prior to installation thereof on the water purification module.

According to tenth embodiments, the disclosed subject matter includes a medicament preparation system with a housing containing a water purification module that includes multiple filtration stages. A medicament proportioning module is connected to receive purified product water generated by the water purification module and to dilute medicament concentrate in predefined proportions to generate a predefined medicament at a medicament product outlet thereof. Each filter media container has a data carrier with data indicating characteristics of the each filter media container. The housing has a data reader that reads data from the data carriers installed on the filter media containers.

Variations of the tenth embodiments may be provided to form additional tenth embodiments in which the characteristics include data from the data carriers indicating whether the media have ever been exhausted prior to installation thereof on the water purification module. Variations of the tenth embodiments may be provided to form additional tenth embodiments in which the characteristics include data indicating whether the media have ever been exhausted prior to installation thereof on the water purification module. Variations of the tenth embodiments may be provided to form additional tenth embodiments in which the filter media containers contain, respectively, carbon filtration and separated-bed and mixed bed deionization filter beds. Variations of the tenth embodiments may be provided to form additional tenth embodiments that include a water quality sensor positioned to detect the quality of water received by the water purification module and a programmable controller programmed to output a limit signal used to limit the amount of water processed through the water purification module responsively to historical data responsive to the water quality indication over time and the data indicating characteristics of media of the filter media containers. Variations of the tenth embodiments may be provided to form additional tenth embodiments in which the characteristics include data from the data carriers indicating whether the media have ever been exhausted prior to installation thereof on the water purification module. Variations of the tenth embodiments may be provided to form additional tenth embodiments in which the characteristics include data indicating whether the media have ever been exhausted prior to installation thereof on the water purification module. Variations of the tenth embodiments may be provided to form additional tenth embodiments in which the filter media containers contain, respectively, carbon filtration and separated-bed and mixed bed deionization filter beds. Variations of the tenth embodiments may be provided to form additional tenth embodiments in which the controller is programmed to limit the amount of water processed by controlling a pump responsively to the limit signal. Variations of the tenth embodiments may be provided to form additional tenth embodiments in which the controller is programmed to limit the amount of water processed by outputting an error indication on a user interface responsively to the limit signal. Variations of the tenth embodiments may be provided to form additional tenth embodiments that include a first water quality sensor positioned to detect the quality of water received by the water purification module and a second water quality sensor positioned to detect the quality of water processed by the water purification module, and a programmable controller programmed to output a limit signal used to limit the amount of water processed through the water purification module responsively to historical data responsive to the water quality indication over time and data indicating characteristics of media of the filter media containers.

Variations of the tenth embodiments may be provided to form additional tenth embodiments in which the controller is programmed to limit the amount of water processed by controlling a pump responsively to the limit signal. Variations of the tenth embodiments may be provided to form additional tenth embodiments in which the controller is programmed to limit the amount of water processed by outputting an error indication on a user interface responsively to the limit signal. Variations of the tenth embodiments may be provided to form additional tenth embodiments in which the characteristics include data indicating whether the media have been used prior to installation thereof on the water purification module. Variations of the tenth embodiments may be provided to form additional tenth embodiments in which the characteristics include data indicating whether the media have ever been exhausted prior to installation thereof on the water purification module. In other variations, the filter media containers contain at least one of a carbon filtration, separated-bed, and mixed bed deionization filter beds.

According to eleventh embodiments, the disclosed subject matter includes a fluid circuit for preparation of a medicament for renal replacement therapy. A concentrate container of concentrate connected for flow communication, through a first pumping tube segment, to a medicament supply line is capped and sterile-sealed at an outlet end thereof. A bicarbonate cartridge contains dry bicarbonate buffer compound, the cartridge is of a type that admits water into a cartridge inlet thereby forming a saturated bicarbonate solution which is received at a cartridge outlet, the cartridge outlet is connected for flow communication, through a second pumping tube segment, to the medicament supply line. A water inlet line has a sterile filter positioned to ensure that all water entering the fluid circuit passes therethrough, the water inlet is capped and sterile-sealed, and connected for flow communication, through a third pumping tube segment, to the medicament supply line and connected for flow communication to the bicarbonate cartridge inlet. The entire fluid circuit is a product of a process in which the entire circuit is pre-connected and sterile-sealed, sterilized as a whole includes the bicarbonate cartridge and the concentrate container is either filled before the entire circuit is sterilized as a whole or a sterile filter is pre-connected to the fluid circuit which is sterilized as a whole and the medicament concentrate is filled into the container through the filter whereupon a channel between the container and the filter is permanently sealed in such a way that no contaminants can thereafter enter the fluid circuit.

Variations of the eleventh embodiments may be provided to form additional eleventh embodiments in which the first, second, and third pumping tube segments are supported by a circuit cartridge which orients, aligns, and exposes for access the first, second, and third pumping tube segments with respective actuators of a predefined medicament preparation device. Variations of the eleventh embodiments may be provided to form additional eleventh embodiments in which the circuit cartridge containing a first concentration sensor station positioned in the medicament supply line downstream of a first junction where a first of the first and second pumping tube segments connects to the medicament supply line. Variations of the eleventh embodiments may be provided to form additional eleventh embodiments in which the circuit cartridge containing a second concentration sensor station positioned in the medicament supply line downstream of both the first junction and a second junction where a second of the first and second pumping tube segments connects to the medicament supply line. Variations of the eleventh embodiments may be provided to form additional eleventh embodiments in which the circuit cartridge includes a fluid accumulator fluidly coupled between the water inlet line and the medicament supply line outlet end that includes a pressure-regulating urging element that biases a flexible wall of the accumulator such that transient changes of fluid pressure therein cause expansion of the volume of the accumulator. Variations of the eleventh embodiments may be provided to form additional eleventh embodiments in which the fluid circuit is packaged with a box such that the circuit cartridge can be detached or removed from the box while leaving the concentrate container and bicarbonate cartridge intact therein with lengths of connecting lines between the circuit cartridge and the box, thereby permitting the circuit cartridge to be installed in a position remote form a position where the box is installed. Variations of the eleventh embodiments may be provided to form additional eleventh embodiments in which the fluid circuit is packaged within a box such that the circuit cartridge can be removed from the box while leaving the concentrate container and bicarbonate cartridge intact therein with lengths of connecting lines between the circuit cartridge and the box, thereby permitting the circuit cartridge to be installed in a position remote form a position where the box is installed. Variations of the eleventh embodiments may be provided to form additional eleventh embodiments in which the fluid circuit is attached to a box in such a way that the circuit cartridge can be detached from the box while leaving the concentrate container and bicarbonate cartridge intact therein with lengths of connecting lines between the circuit cartridge and the box, thereby permitting the circuit cartridge to be installed in a position remote form a position where the box is installed. Variations of the eleventh embodiments may be provided to form additional eleventh embodiments in which the box is principally of cardboard. In other variations, wherein each of the concentration sensor stations includes a liquid conductivity sensor and temperature sensor portions. Variations of the eleventh embodiments may be provided to form additional eleventh embodiments in which the temperature sensor portion includes a flow chamber with a flat surface to permit a temperature sensor to be placed against the flat surface of a predefined sensor of the predefined medicament preparation device. Variations of the eleventh embodiments may be provided to form additional eleventh embodiments in which each of the concentration stations includes, connected in series, two independent conductivity sensors and two independent temperature sensor portions. Variations of the eleventh embodiments may be provided to form additional eleventh embodiments in which the medicament supply line includes a waste outlet branch that is in direct fluid communication with the accumulator, the waste outlet line is capped and sterile-sealed, the medicament supply line outlet line and waste outlet branches has pinching portions supported in an open section of the circuit cartridge to permit access by pinching actuators.

According to twelfth embodiments, the disclosed subject matter includes a fluid circuit for preparation of a medicament for renal replacement therapy. The circuit includes least one container of concentrate connected for flow communication, through at least one first pumping tube segment respective for each of the at least one container, to a medicament supply line that has been capped and sterile-sealed at an outlet end thereof. A water inlet line has a sterile filter positioned to ensure that all water entering the fluid circuit passes therethrough, the water inlet is capped and sterile-sealed, and connected for flow communication, through a second pumping tube segment, to the medicament supply line. The entire fluid circuit is a product of a process in which the fluid circuit is pre-connected and sterile-sealed, sterilized as a whole and the concentrate container is either filled before the entire circuit is sterilized as a whole or a sterile filter is pre-connected to a filling port of each of the at least one container, the fluid circuit which is sterilized as a whole, and at least one medicament concentrate is filled into the at least one container through a respective one the sterile filters whereupon a channel between the container and the filter is permanently sealed in such a way that no contaminants can thereafter enter the fluid circuit.

Variations of the twelfth embodiments may be provided to form additional twelfth embodiments in which the first, second, and third pumping tube segments are supported by a circuit cartridge which orients, aligns, and exposes for access the first, second, and third pumping tube segments with respective actuators of a predefined medicament preparation device. Variations of the twelfth embodiments may be provided to form additional twelfth embodiments in which the circuit cartridge containing a first concentration sensor station positioned in the medicament supply line downstream of a first junction where a first of the first and second pumping tube segments connects to the medicament supply line. Variations of the twelfth embodiments may be provided to form additional twelfth embodiments in which the circuit cartridge containing a second concentration sensor station positioned in the medicament supply line downstream of both the first junction and a second junction where a second of the first and second pumping tube segments connects to the medicament supply line. Variations of the twelfth embodiments may be provided to form additional twelfth embodiments in which the circuit cartridge includes a fluid accumulator fluidly coupled between the water inlet line and the medicament supply line outlet end that includes a pressure-regulating urging element that biases a flexible wall of the accumulator such that transient changes of fluid pressure therein cause expansion of the volume of the accumulator. Variations of the twelfth embodiments may be provided to form additional twelfth embodiments in which the fluid circuit is packaged with a box such that the circuit cartridge can be detached or removed from the box while leaving the at least one container intact therein with lengths of connecting lines between the circuit cartridge and the box, thereby permitting the circuit cartridge to be installed in a position remote form a position where the box is installed. Variations of the twelfth embodiments may be provided to form additional twelfth embodiments in which the fluid circuit is packaged within a box such that the circuit cartridge can be removed from the box while leaving the at least one container intact therein with lengths of connecting lines between the circuit cartridge and the box, thereby permitting the circuit cartridge to be installed in a position remote form a position where the box is installed. Variations of the twelfth embodiments may be provided to form additional twelfth embodiments in which the fluid circuit is attached to a box in such a way that the circuit cartridge can be detached from the box while leaving the at least one container intact therein with lengths of connecting lines between the circuit cartridge and the box, thereby permitting the circuit cartridge to be installed in a position remote form a position where the box is installed. Variations of the twelfth embodiments may be provided to form additional twelfth embodiments in which the box is principally of cardboard. In other variations, wherein each of the concentration sensor stations includes a liquid conductivity sensor and temperature sensor portions. Variations of the twelfth embodiments may be provided to form additional twelfth embodiments in which the temperature sensor portion includes a flow chamber with a flat surface to permit a temperature sensor to be placed against the flat surface of a predefined sensor of the predefined medicament preparation device. Variations of the twelfth embodiments may be provided to form additional twelfth embodiments in which each of the concentration stations includes, connected in series, two independent conductivity sensors and two independent temperature sensor portions. Variations of the twelfth embodiments may be provided to form additional twelfth embodiments in which the medicament supply line includes a waste outlet branch that is in direct fluid communication with the accumulator, the waste outlet line is capped and sterile-sealed, the medicament supply line outlet line and waste outlet branches has pinching portions supported in an open section of the circuit cartridge to permit access by pinching actuators.

According to thirteenth embodiments, the disclosed subject matter includes a compact medicament supply system to support blood treatment systems susceptible to leakage current from electric heater used to heat medicament due to the inherent formation of a fluid path between the heater and the patient. A water purification module has a pump and a controller, the water purification module has deionization filters of sufficient capacity and the pump controlled to purify water to a level of purity exceeding 1 megohm-cm and providing product water at at least that level of purity to a product water output connected to an electric heater. A water channel of a predefined length and of electrically insulating material connects the electric heater to a medicament proportioning module disposable fluid circuit, the water channel receiving the product water from the electric heater. The electric heater is of a configuration that places the product water in direct contact with permanent non-disposable surfaces of a flow channel in the electric heater. A sterile filter is connected to receive the product water at a point along the water channel, and the water channel has a output connector for connecting to the medicament proportioning system. The medicament proportioning system, principally of electrically insulating material, is connected to supply a conductive medicament solution to a treatment component connected to a patient via a blood circuit includes a patient access such that a continuous fluid path between the electric heater and the patient access at times during a treatment. A controller is adapted for controlling the electric heater responsively to a measured temperature and temperature target selected for maintaining the body temperature of a human patient connected via the blood circuit to the treatment component, the controller compensating for heat load due the addition of medicament concentrate to the flow of product water. A length of the water channel and a resistivity of the product water therein is sufficient to ensure that the electric heater produces less than 50 microamperes of leakage current through the continuous fluid path to the patient access, whereby heat required to maintain body temperature of a patient is treated by a blood treatment is provided through an electrically insulating convective flow of pure water used for the generation of medicament used in the treatment.

Variations of the thirteenth embodiments may be provided to form additional thirteenth embodiments in which the electric heater has double-insulated heating elements.

According to fourteenth embodiments, the disclosed subject matter includes a method for regulating a temperature of medicament for extracorporeal blood processing. The method includes providing pure water of a predefined resistivity. The method further includes using an electric heating element, heating the pure water. The method further includes flowing the purified water through an electrically insulating channel of such length and cross-section, and the predefined resistivity is such as to ensure that a leakage current of less than 50 microamperes reaches and end thereof. The method further includes diluting or dissolving medicament solute with a flow of the purified water starting at the end at a rate to achieve a concentration of a product medicament resulting from the diluting or dissolving is suitable for immediate use in a blood treatment. The method further includes regulating a rate of the heating water to ensure that a temperature of the product maintains a temperature of a human patient during an extracorporeal blood treatment that consumes the product medicament, whereby a resistive water path is effective to electrically insulate the electric heating element from a patient receiving treatment to safeguard against a health risk from current leakage therefrom.

Variations of the fourteenth embodiments may be provided to form additional fourteenth embodiments in which the providing includes deionizing water to produce the pure water. Variations of the fourteenth embodiments may be provided to form additional fourteenth embodiments that include sterile-filtering the water prior to the diluting or dissolving. Variations of the fourteenth embodiments may be provided to form additional fourteenth embodiments in which the diluting or dissolving includes injecting medicament concentrate into a flow of pure water using a disposable fluid circuit. Variations of the fourteenth embodiments may be provided to form additional fourteenth embodiments that include regulating a rate of pure water production responsively to the rate of consumption of medicament by the extracorporeal blood treatment. Variations of the fourteenth embodiments may be provided to form additional fourteenth embodiments that include regulating a patient temperature by regulating a rate of heat addition to pure water that with a resistivity of at 100 kiloohm-cms. Variations of the fourteenth embodiments may be provided to form additional fourteenth embodiments that include regulating a rate of pure water production responsively to the rate of consumption of medicament by the extracorporeal blood treatment. Variations of the fourteenth embodiments may be provided to form additional fourteenth embodiments that include regulating a rate of purified water production, the heat applied to purified water production is proportional to a rate of heat addition to responsively to the rate of consumption of medicament by the extracorporeal blood treatment.

According to fifteenth embodiments, the disclosed subject matter includes a mobile medicament supply system to support blood treatment systems susceptible to leakage current from electric heater used to heat medicament due to the inherent formation of a fluid path between the heater and the patient. A source of pure water provides pure water with a resistivity exceeding 1 megohm-cm. The source is connected to an electric heater. A water channel has a predefined length and of electrically insulating material connecting the electric heater to a medicament proportioning module disposable fluid circuit. The water channel receives the pure water from the electric heater. The medicament proportioning system is principally of electrically insulating material and connected to supply a conductive medicament solution to a treatment component connected to a patient via a blood circuit includes a patient access such that a continuous fluid path between the electric heater and the patient access at times during a treatment. A controller is adapted for controlling the electric heater to achieve a target temperature selected to maintain the body temperature of a human patient connected via the blood circuit to the treatment component, the controller providing additional heat to compensate for heat load resulting from the cooing effect of adding medicament concentrate to the flow of pure water. A length of the water channel, a cross-section thereof, and a resistivity of the pure water therein is sufficient to ensure that the electric heater produces less than 50 microamperes of leakage current through the continuous fluid path to the patient access, whereby heat required to maintain body temperature of a patient is treated by a blood treatment is provided through an electrically insulating convective flow of pure water used for the generation of medicament used in the treatment.

Variations of the fifteenth embodiments may be provided to form additional fifteenth embodiments in which the source of pure water includes a water purification module. Variations of the fifteenth embodiments may be provided to form additional fifteenth embodiments in which the water purification module has a pump and a controller. Variations of the fifteenth embodiments may be provided to form additional fifteenth embodiments in which the water purification module has deionization filters of sufficient capacity to purify water to a resistivity exceeding 1 megohm-cm. Variations of the fifteenth embodiments may be provided to form additional fifteenth embodiments in which the electric heater is of a configuration that places the product water in direct contact with permanent non-disposable surfaces of a flow channel in the electric heater. Variations of the fifteenth embodiments may be provided to form additional fifteenth embodiments that include a sterile filter connected to receive the pure water at a point along the water channel, and the water channel has a output connector for connecting to the medicament proportioning system. Variations of the fifteenth embodiments may be provided to form additional fifteenth embodiments in which the electric heater has double-insulated heating elements.

According to sixteenth embodiments, the disclosed subject matter includes a medicament proportioning system with a disposable fluid circuit that has a generally planar element with a base portion and wall elements formed thereon. The wall elements define trough-shaped channels which are sealed by a film sealingly attached to the edges of the walls opposite an edge of each wall that attaches to the base element to enclose the trough shaped channels. The trough shaped channels include elongate portions that interconnect fluid circuit elements. First of the fluid circuit elements include widened portions of the trough shaped channels that are positioned on the base portion to engage one or both of temperature and pressure sensors of a predefined medicament proportioning module. Second of the fluid circuit elements include at least one pumping tube segment or at least one pinch-clamping actuator of the predefined medicament proportioning module that engages with a pumping actuator or pinch-clamping actuator of the predefined medicament proportioning module. The second of the fluid circuit elements interface with a junction part defining a recess has an access and blind end spaced apart along an axis of the junction part recess that is parallel with a major plane of the planar element base portion. An opening is formed in the planar element to form a fluid communication channel between each junction part recess and a region of the trough shaped channels.

Variations of the sixteenth embodiments may be provided to form additional sixteenth embodiments in which the second of the fluid circuit elements has a tubular portion inserted in the junction part recess, and the tubular portion has a longitudinal axis collinear with the recess axis. Variations of the sixteenth embodiments may be provided to form additional sixteenth embodiments in which the second of the fluid circuit elements include at least one pumping tube segment that engages with a pinch-clamping actuator of the predefined medicament proportioning module. Variations of the sixteenth embodiments may be provided to form additional sixteenth embodiments in which the trough shaped channels and the first fluid circuit elements are located on a first major face of the planar element base portion that is opposite a second major face, the second fluid circuit elements is attached to the second major face. Variations of the sixteenth embodiments may be provided to form additional sixteenth embodiments in which the trough shaped channels and the first fluid circuit elements are located on a first major face of the planar element base portion that is opposite a second major face, the second fluid circuit elements is attached to the second major face.

Variations of the sixteenth embodiments may be provided to form additional sixteenth embodiments that include third of the fluid circuit elements that include at least one column-shaped channel with electrodes on a side thereof, where the electrodes are positioned in the planar element base portion and extend between a first major face of the planar element base portion to an opposite second major face thereof.

Variations of the sixteenth embodiments may be provided to form additional sixteenth embodiments in which the trough shaped channels and the first fluid circuit elements are located on the first major face of the planar element base portion and the second and third fluid circuit elements are attached to the second major face. Variations of the sixteenth embodiments may be provided to form additional sixteenth embodiments in which the column-shaped channel defines a recess has an access and blind end spaced apart along an axis of the column-shaped part recess that is parallel with a major plane of the planar element base portion. Variations of the sixteenth embodiments may be provided to form additional sixteenth embodiments in which the column-shaped part recess access is closed with an end plate. Variations of the sixteenth embodiments may be provided to form additional sixteenth embodiments in which the column-shaped channel defines a recess has an access and blind end spaced apart along an axis of the column-shaped part recess that is parallel with a major plane of the planar element base portion. Variations of the sixteenth embodiments may be provided to form additional sixteenth embodiments in which the column-shaped part recess access is closed with an end plate. Variations of the sixteenth embodiments may be provided to form additional sixteenth embodiments in which the planar element has an opening to form a fluid communication channel between each column-shaped channel recess and a region of the trough shaped channels.

Variations of the sixteenth embodiments may be provided to form additional sixteenth embodiments in which the second of the fluid circuit elements include at least one pumping tube segment that engages with a pumping actuator of the predefined medicament proportioning module, wherein the trough shaped channels and the first fluid circuit elements are located on a first major face of the planar element base portion that is opposite a second major face, the second fluid circuit elements is attached to the second major face, and the planar element has openings to permit actuators of the predefined medicament proportioning module to reach from the first side to the second side to engage the at least one pumping tube segment. Variations of the sixteenth embodiments may be provided to form additional sixteenth embodiments in which the second of the fluid circuit elements include at least one pinch tube segment that engages with a pinch clamp actuator of the predefined medicament proportioning module, wherein the trough shaped channels and the first fluid circuit elements are located on a first major face of the planar element base portion that is opposite a second major face, the second fluid circuit elements is attached to the second major face, and the planar element has openings to permit actuators of the predefined medicament proportioning module to reach from the first side to the second side to engage the at least one pinch tube segment. Variations of the sixteenth embodiments may be provided to form additional sixteenth embodiments in which the second of the fluid circuit elements include at least one pumping tube segment that engages with a pumping actuator of the predefined medicament proportioning module, wherein the trough shaped channels and the first fluid circuit elements are located on a first major face of the planar element base portion that is opposite a second major face, the second fluid circuit elements is attached to the second major face, and the planar element has openings to permit actuators of the predefined medicament proportioning module to reach from the first side to the second side to engage the at least one pumping tube segment. Variations of the sixteenth embodiments may be provided to form additional sixteenth embodiments in which the second of the fluid circuit elements include at least one pinch tube segment that engages with a pinch clamp actuator of the predefined medicament proportioning module, wherein the trough shaped channels and the first fluid circuit elements are located on a first major face of the planar element base portion that is opposite a second major face, the second fluid circuit elements is attached to the second major face, and the planar element has openings to permit actuators of the predefined medicament proportioning module to reach from the first side to the second side to engage the at least one pinch tube segment. Variations of the sixteenth embodiments may be provided to form additional sixteenth embodiments that include third of the fluid circuit elements that include at least one column-shaped channel with electrodes on a side thereof, where the electrodes are positioned in the planar element base portion and extend between a first major face of the planar element base portion to an opposite second major face thereof.

Variations of the sixteenth embodiments may be provided to form additional sixteenth embodiments that include third of the fluid circuit elements that include at least one column-shaped channel with electrodes on a side thereof, where the electrodes are positioned in the planar element base portion and extend between a first major face of the planar element base portion to an opposite second major face thereof Variations of the sixteenth embodiments may be provided to form additional sixteenth embodiments that include third of the fluid circuit elements that include at least one column-shaped channel with electrodes on a side thereof, where the electrodes are positioned in the planar element base portion and extend between a first major face of the planar element base portion to an opposite second major face thereof. Variations of the sixteenth embodiments may be provided to form additional sixteenth embodiments that include third of the fluid circuit elements that include at least one column-shaped channel with electrodes on a side thereof, where the electrodes are positioned in the planar element base portion and extend between a first major face of the planar element base portion to an opposite second major face thereof. Variations of the sixteenth embodiments may be provided to form additional sixteenth embodiments in which the column-shaped channel defines a recess has an access and blind end spaced apart along an axis of the column-shaped part recess that is parallel with a major plane of the planar element base portion, the junction part recess axis and the column shaped part recess axis is parallel to permit a single action to form both during molding.

Variations of the sixteenth embodiments may be provided to form additional sixteenth embodiments in which the column-shaped part recess access is closed with an end plate. Variations of the sixteenth embodiments may be provided to form additional sixteenth embodiments in which the column-shaped channel defines a recess has an access and blind end spaced apart along an axis of the column-shaped part recess that is parallel with a major plane of the planar element base portion, the junction part recess axis and the column shaped part recess axis is parallel to permit a single action to form both during molding. Variations of the sixteenth embodiments may be provided to form additional sixteenth embodiments in which the column-shaped part recess access is closed with an end plate. Variations of the sixteenth embodiments may be provided to form additional sixteenth embodiments in which the planar element has an opening to form a fluid communication channel between each column-shaped channel recess and a region of the trough shaped channels. Variations of the sixteenth embodiments may be provided to form additional sixteenth embodiments in which the wall elements coincide with a single plane. Variations of the sixteenth embodiments may be provided to form additional sixteenth embodiments in which the trough shaped channels and the first fluid circuit elements are located on a first major face of the planar element base portion that is opposite a second major face, the second fluid circuit elements is attached to the second major face.

According to seventeenth embodiments, the disclosed subject matter includes a medicament proportioning system. A medicament proportioning module has a pump with a pumping actuator or a pinch-clamp actuator, and at least one temperature or pressure sensor. A disposable fluid circuit has a generally planar element has a base portion and wall elements formed thereon, the wall elements defining trough-shaped channels which are sealed by a film sealingly attached to the edges of the walls opposite an edge of each wall that attaches to the base element to enclose the trough shaped channels. The trough shaped channels include elongate portions that interconnect fluid circuit elements. The medicament proportioning module has one or both of a temperature and pressure sensor. First of the fluid circuit elements include widened portions of the trough shaped channels that are positioned on the base portion to engage the one or both of the at least one temperature or pressure sensor of the medicament proportioning module. Second of the fluid circuit elements include at least one pumping tube segment or at least one pinch-clamping actuator of the medicament proportioning module that engages with a pumping actuator or pinch-clamping actuator of the medicament proportioning module. The second of the fluid circuit elements interface with a junction part defining a recess has an access and blind end spaced apart along an axis of the junction part recess that is parallel with a major plane of the planar element base portion. An opening is formed in the planar element to form a fluid communication channel between each junction part recess and a region of the trough shaped channels.

Variations of the seventeenth embodiments may be provided to form additional seventeenth embodiments in which the second of the fluid circuit elements has a tubular portion inserted in the junction part recess, and the tubular portion has a longitudinal axis collinear with the recess axis. Variations of the seventeenth embodiments may be provided to form additional seventeenth embodiments in which the second of the fluid circuit elements include at least one pumping tube segment that engages with a pinch-clamping actuator of the medicament proportioning module. Variations of the seventeenth embodiments may be provided to form additional seventeenth embodiments in which the trough shaped channels and the first fluid circuit elements are located on a first major face of the planar element base portion that is opposite a second major face, the second fluid circuit elements is attached to the second major face. Variations of the seventeenth embodiments may be provided to form additional seventeenth embodiments in which the trough shaped channels and the first fluid circuit elements are located on a first major face of the planar element base portion that is opposite a second major face, the second fluid circuit elements is attached to the second major face.

Variations of the seventeenth embodiments may be provided to form additional seventeenth embodiments that include third of the fluid circuit elements that include at least one column-shaped channel with electrodes on a side thereof, where the electrodes are positioned in the planar element base portion and extend between a first major face of the planar element base portion to an opposite second major face thereof, the medicament proportioning module has electrical contacts facing the first major face and positioned to contact the electrodes. Variations of the seventeenth embodiments may be provided to form additional seventeenth embodiments in which the trough shaped channels and the first fluid circuit elements are located on the first major face of the planar element base portion and the second and third fluid circuit elements are attached to the second major face. Variations of the seventeenth embodiments may be provided to form additional seventeenth embodiments in which the column-shaped channel defines a recess has an access and blind end spaced apart along an axis of the column-shaped part recess that is parallel with a major plane of the planar element base portion. Variations of the seventeenth embodiments may be provided to form additional seventeenth embodiments in which the column-shaped part recess access is closed with an end plate. Variations of the seventeenth embodiments may be provided to form additional seventeenth embodiments in which the column-shaped channel defines a recess has an access and blind end spaced apart along an axis of the column-shaped part recess that is parallel with a major plane of the planar element base portion. Variations of the seventeenth embodiments may be provided to form additional seventeenth embodiments in which the column-shaped part recess access is closed with an end plate. T Variations of the seventeenth embodiments may be provided to form additional seventeenth embodiments in which the planar element has an opening to form a fluid communication channel between each column-shaped channel recess and a region of the trough shaped channels. Variations of the seventeenth embodiments may be provided to form additional seventeenth embodiments in which the medicament proportioning module has a pumping actuator and the second of the fluid circuit elements include at least one pumping tube segment that engages with the pumping actuator of the medicament proportioning module, wherein the trough shaped channels and the first fluid circuit elements are located on a first major face of the planar element base portion that is opposite a second major face, the second fluid circuit elements is attached to the second major face, and the planar element has openings to permit actuators of the medicament proportioning module to reach from the first side to the second side to engage the at least one pumping tube segment. Variations of the seventeenth embodiments may be provided to form additional seventeenth embodiments in which the medicament proportioning module has a pinch clamp actuator and the second of the fluid circuit elements include at least one pinch tube segment that engages with the pinch clamp actuator of the medicament proportioning module, wherein the trough shaped channels and the first fluid circuit elements are located on a first major face of the planar element base portion that is opposite a second major face, the second fluid circuit elements is attached to the second major face, and the planar element has openings to permit actuators of the medicament proportioning module to reach from the first side to the second side to engage the at least one pinch tube segment.

Variations of the seventeenth embodiments may be provided to form additional seventeenth embodiments in which the medicament proportioning module has a pumping actuator and the second of the fluid circuit elements include at least one pumping tube segment that engages with the pumping actuator of the medicament proportioning module, wherein the trough shaped channels and the first fluid circuit elements are located on a first major face of the planar element base portion that is opposite a second major face, the second fluid circuit elements is attached to the second major face, and the planar element has openings to permit actuators of the medicament proportioning module to reach from the first side to the second side to engage the at least one pumping tube segment. Variations of the seventeenth embodiments may be provided to form additional seventeenth embodiments in which the medicament proportioning module has a pinching actuator and the second of the fluid circuit elements include at least one pinch tube segment that engages with the pinch clamp actuator of the medicament proportioning module, wherein the trough shaped channels and the first fluid circuit elements are located on a first major face of the planar element base portion that is opposite a second major face, the second fluid circuit elements is attached to the second major face, and the planar element has openings to permit actuators of the medicament proportioning module to reach from the first side to the second side to engage the at least one pinch tube segment. Variations of the seventeenth embodiments may be provided to form additional seventeenth embodiments that include third of the fluid circuit elements that include at least one column-shaped channel with electrodes on a side thereof, where the electrodes are positioned in the planar element base portion and extend between a first major face of the planar element base portion to an opposite second major face thereof. In other variations, the system further comprises third of the fluid circuit elements that include at least one column-shaped channel with electrodes on a side thereof, where the electrodes are positioned in the planar element base portion and extend between a first major face of the planar element base portion to an opposite second major face thereof, the medicament proportioning module has a conductivity detection circuit with contacts positioned to make electrical contact with the electrodes.

Variations of the seventeenth embodiments may be provided to form additional seventeenth embodiments that include third of the fluid circuit elements that include at least one column-shaped channel with electrodes on a side thereof, where the electrodes are positioned in the planar element base portion and extend between a first major face of the planar element base portion to an opposite second major face thereof, the medicament proportioning module has a conductivity detection circuit with contacts positioned to make electrical contact with the electrodes. In other variations, the system further comprises third of the fluid circuit elements that include at least one column-shaped channel with electrodes on a side thereof, where the electrodes are positioned in the planar element base portion and extend between a first major face of the planar element base portion to an opposite second major face thereof, the medicament proportioning module has a conductivity detection circuit with contacts positioned to make electrical contact with the electrodes. Variations of the seventeenth embodiments may be provided to form additional seventeenth embodiments in which the column-shaped channel defines a recess has an access and blind end spaced apart along an axis of the column-shaped part recess that is parallel with a major plane of the planar element base portion, the junction part recess axis and the column shaped part recess axis is parallel to permit a single action to form both during molding. Variations of the seventeenth embodiments may be provided to form additional seventeenth embodiments in which the column-shaped part recess access is closed with an end plate.

Variations of the seventeenth embodiments may be provided to form additional seventeenth embodiments in which the column-shaped channel defines a recess has an access and blind end spaced apart along an axis of the column-shaped part recess that is parallel with a major plane of the planar element base portion, the junction part recess axis and the column shaped part recess axis is parallel to permit a single action to form both during molding. Variations of the seventeenth embodiments may be provided to form additional seventeenth embodiments in which the column-shaped part recess access is closed with an end plate. Variations of the seventeenth embodiments may be provided to form additional seventeenth embodiments in which the planar element has an opening to form a fluid communication channel between each column-shaped channel recess and a region of the trough shaped channels. Variations of the seventeenth embodiments may be provided to form additional seventeenth embodiments in which the medicament proportioning module has a data reader and the planar element base portion has a data carrier readable by the data reader. Variations of the seventeenth embodiments may be provided to form additional seventeenth embodiments in which the data carrier is attached to the first major face and the data reader is positioned on the medicament proportioning module on a side of the first side of the planar element base portion toward which the first major face faces. Variations of the seventeenth embodiments may be provided to form additional seventeenth embodiments in which the wall elements coincide with a single plane. Variations of the seventeenth embodiments may be provided to form additional seventeenth embodiments in which the trough shaped channels and the first fluid circuit elements are located on a first major face of the planar element base portion that is opposite a second major face, the second fluid circuit elements is attached to the second major face.

According to eighteenth embodiments, the disclosed subject matter includes a medicament proportioning system with a water purification module that has a tap water inlet, deionization filters, and a purified water outlet. A medicament proportioning module is connected to receive water from the purified water outlet, and the medicament proportioning module is interoperable with a replaceable medicament fluid circuit by engaging sensors, actuators, and a controller incorporated therein. The replaceable medicament fluid circuit is a replaceable unit with at least one inlet and two outlets, and includes: (1) a water inlet for water, (2) a medicament outlet for product medicament output, and (3) a waste outlet for waste fluid. The replaceable medicament fluid circuit has, permanently attached thereto, at least one concentrate container filled with medicament concentrate and is entirely sealed from an external environment such that the at least one inlet is the exclusive mechanism for admission of fluid into the replaceable medicament fluid circuit. The at least one inlet has a sterile filter to block the movement of any contaminants from entering the replaceable medicament fluid circuit due to the making of the connection between the water outlet and the water inlet or otherwise. The replaceable medicament fluid circuit has an interior volume that is sterile with the at least one inlet and outlets is openably sealed, whereby the replaceable medicament fluid circuit may be provided as a sterile unit with a minimum of connections to be made.

Variations of the eighteenth embodiments may be provided to form additional eighteenth embodiments in which the replaceable medicament fluid circuit has water pumping tube segment connected to convey water from the water inlet toward the medicament outlet, and at least one medicament pumping tube segment connected to convey the at least one medicament into a product fluid channel connecting the water inlet to the medicament outlet. Variations of the eighteenth embodiments may be provided to form additional eighteenth embodiments in which the medicament proportioning module has a water pump actuator shaped and positioned to pump water through the water pumping tube segment at least one medicament pump actuator shaped and positioned to pump medicament through the medicament pumping tube segment, wherein the at least one medicament pumping tube segment connects the at least one medicament concentrate container to the product fluid channel. Variations of the eighteenth embodiments may be provided to form additional eighteenth embodiments in which the at least one inlet and two outlets all include a respective sterile filter. Variations of the eighteenth embodiments may be provided to form additional eighteenth embodiments in which the at least two outlets include a check valve.

Variations of the eighteenth embodiments may be provided to form additional eighteenth embodiments in which the replaceable medicament fluid circuit has a self-supporting container containing the at least one concentrate container connected by tubes to a cartridge, the cartridge has the sensor and actuator portions of the medicament fluid circuit that engage with the sensors and actuators of the medicament proportioning module. Variations of the eighteenth embodiments may be provided to form additional eighteenth embodiments in which the cartridge has a data carrier that transmits data to the controller. Variations of the eighteenth embodiments may be provided to form additional eighteenth embodiments in which the data carrier contains data that indicates the composition of the medicament concentrate in the at least one concentrate container. Variations of the eighteenth embodiments may be provided to form additional eighteenth embodiments in which the at least one concentrate container includes a concentrate container with a dry solute has a diluent water inlet, and the cartridge has a pinch valve segment for controlling water flow from the water inlet to the diluent water inlet. Variations of the eighteenth embodiments may be provided to form additional eighteenth embodiments in which the controller is programmed to regulate flow to the diluent water inlet responsively to a demand for medicament from a device connected to the medicament outlet.

According to nineteenth embodiments, the disclosed subject matter includes a medicament proportioning system with a water purification module that has a tap water inlet and a purified water outlet. The system has deionization filters positioned between the tap water inlet and purified water outlet to purify water. A medicament proportioning module is connected to receive water from the purified water outlet, and the medicament proportioning module is interoperable with a replaceable medicament fluid circuit. The medicament proportioning module has a medicament proportioning fluid circuit with a concentrate pump section and a water pump section that engage respective pump actuators to transfer purified water and concentrate to a medicament supply channel of the medicament proportioning fluid circuit, the medicament supply channel has a product medicament outlet that is connected to supply a mixture of the water and concentrates transferred to the medicament supply channel. The medicament supply channel includes an accumulator with an internal volume whose size is selected to be no more than twice a volume predetermined to be necessary to permit the respective pump actuators to operate a constant speed without starving flow to a predefined consuming device connectable to the product medicament outlet, where the predefined consuming device draws medicament at variable rate.

According to twentieth embodiments, the disclosed subject matter includes a medicament proportioning system with a water purification module, a tap water inlet, and a purified water outlet. Deionization filters are positioned between the tap water inlet and purified water outlet to purify water. A medicament proportioning module is connected to receive water from the purified water outlet, and the medicament proportioning module is interoperable with a replaceable medicament fluid circuit. The medicament proportioning module has a medicament proportioning fluid circuit with a concentrate pump section and a water pump section that engage respective pump actuators to transfer purified water and concentrate to a medicament supply channel of the medicament proportioning fluid circuit. The medicament supply channel has a product medicament outlet that is connected to supply a mixture of the water and concentrates transferred to the medicament supply channel. The medicament supply channel includes an accumulator with rigid button portion supporting, in an expansion direction of expansion and contraction of an internal volume of the accumulator, an elastic web and is supported by the elastic web in one or more directions or moments other than the expansion direction. The rigid button is urged by an urging element positioned and oriented to resist the expansion the accumulator internal volume. The rigid button makes no friction-causing sliding engagement with other portions of the accumulator. As a result, a pressure-volume characteristic of the accumulator internal volume is determined by the urging element.

According to twenty-first embodiments, the disclosed subject matter includes a medicament proportioning system that has a water purification module with a tap water inlet and a purified water outlet. Deionization filters are positioned between the tap water inlet and purified water outlet to purify water. A medicament proportioning module is connected to receive water from the purified water outlet, and the medicament proportioning module is interoperable with a replaceable medicament fluid circuit. The medicament proportioning module has a medicament proportioning fluid circuit with a concentrate pump section and a water pump section that engage respective pump actuators to transfer purified water and concentrate to a medicament supply channel of the medicament proportioning fluid circuit. The medicament supply channel has a product medicament outlet that is connected to supply a mixture of the water and concentrates transferred to the medicament supply channel. The product medicament outlet is connectable to a predefined medicament consuming device that draws medicament at a periodic non-uniform rate of flow. The medicament supply channel includes an accumulator that has a variable internal volume that includes an urging element that provides a progressive pressure-volume characteristic thereof. A pressure transducer is arranged in the medicament supply channel to output a pressure signal indicative of a pressure in the accumulator internal volume, a controller that controls the pump actuators responsively to the pressure signal to operate the pump actuators at a rate that lacks a periodicity of the periodic non-uniform rate of flow.

Variations of the nineteenth and twentieth embodiments may be provided to form additional nineteenth and twentieth embodiments in which the product medicament outlet is connected to a predefined medicament consuming device. Variations of the nineteenth and twentieth embodiments may be provided to form additional nineteenth and twentieth embodiments in which the consuming device is a blood treatment system. Variations of the nineteenth and twentieth embodiments may be provided to form additional nineteenth and twentieth embodiments in which the consuming device is a hemodialysis system. Variations of the nineteenth and twentieth embodiments may be provided to form additional nineteenth and twentieth embodiments in which the consuming device is a volumetric balancing component of a blood treatment system. Variations of the twenty-first embodiments may be provided to form additional twenty-first embodiments in which the product medicament outlet is connected to a predefined medicament consuming device. Variations of the twenty-first embodiments may be provided to form additional twenty-first embodiments in which the consuming device is a blood treatment system. Variations of the twenty-first embodiments may be provided to form additional twenty-first embodiments in which the consuming device is a hemodialysis system. Variations of the twenty-first embodiments may be provided to form additional twenty-first embodiments in which the consuming device is a volumetric balancing component of a blood treatment system.

According to twenty-second embodiments, the disclosed subject matter includes a blood treatment system with a water purification module that has a product water outlet. A medicament proportioning module is connected to receive product water through the product water outlet and has pumps for concentrate and water that are controlled to mix product medicament and convey it through a product medicament channel, connected to a product medicament outlet. A blood treatment module is connected to the product medicament outlet, and the blood treatment module has a pump to draw product medicament from the product medicament outlet. The medicament proportioning module pumps at rate that is responsive to a mechanical signal generated by the blood treatment module, whereby flow between the medicament proportioning module and the blood processing module may be governed without the need for electrical control signals.

Variations of the twenty-second embodiments may be provided to form additional twenty-second embodiments in which the product medicament channel includes an accumulator with an expandable interior volume. Variations of the twenty-second embodiments may be provided to form additional twenty-second embodiments in which the accumulator is at least partly integrated in a replaceable cartridge. Variations of the twenty-second embodiments may be provided to form additional twenty-second embodiments in which the accumulator has a spring that is biased against expansion of an interior volume thereof. Variations of the twenty-second embodiments may be provided to form additional twenty-second embodiments in which the blood processing module includes a volumetric balancing system that draws medicament from the product medicament outlet at an unsteady rate that has a periodic component that is smoothed or canceled by the accumulator, such that rates of flow of the medicament proportioning module pumps responsive to the periodic component is diminished. Variations of the twenty-second embodiments may be provided to form additional twenty-second embodiments in which the blood processing module includes a volumetric balancing system that draws medicament from the product medicament outlet at an unsteady rate that has a periodic component that is canceled by the accumulator, such that rates of flow of the medicament proportioning module pumps responsive to the periodic component is eliminated.

According to twenty-third embodiments, the disclosed subject matter includes a medicament supply system with a water purification module that has a product water outlet. A medicament proportioning module is connected to receive product water through the product water outlet and has pumps for concentrate and water that are controlled to mix product medicament and convey it through a product medicament channel, connected to a product medicament outlet. The medicament proportioning module pumps at rate controlled to maintain a target average pressure at the product medicament outlet such that an attached medicament consuming device can draw fluid at a current pressure at the product medicament outlet on-demand. The medicament proportioning module has an accumulator upstream of the product medicament outlet to permit irregular or periodic draw of medicament therefrom without a need for a concomitant irregular or periodic change in the pumping rate of the medicament proportioning module pumps.

Variations of the twenty-third embodiments may be provided to form additional twenty-third embodiments in which the product medicament channel includes an accumulator with an expandable interior volume. Variations of the twenty-third embodiments may be provided to form additional twenty-third embodiments in which the accumulator is at least partly integrated in a replaceable cartridge. Variations of the twenty-third embodiments may be provided to form additional twenty-third embodiments in which the accumulator has a spring that is biased against expansion of an interior volume thereof. Variations of the twenty-third embodiments may be provided to form additional twenty-third embodiments in which the blood processing module includes a volumetric balancing system that draws medicament from the product medicament outlet at an unsteady rate that has a periodic component that is smoothed or canceled by the accumulator, such that rates of flow of the medicament proportioning module pumps responsive to the periodic component is diminished. Variations of the twenty-third embodiments may be provided to form additional twenty-third embodiments in which the blood processing module includes a volumetric balancing system that draws medicament from the product medicament outlet at an unsteady rate that has a periodic component that is canceled by the accumulator, such that rates of flow of the medicament proportioning module pumps responsive to the periodic component is eliminated.

According to twenty-fourth embodiments, the disclosed subject matter includes a blood treatment system. A water purification module has a product water outlet. A medicament proportioning module is connected to receive product water through the product water outlet and has pumps for concentrate and water that are controlled to mix product medicament and convey it through a product medicament channel, connected to a product medicament outlet. A blood treatment module, separately housed from the water purification and medicament proportioning modules, is connected to the product medicament outlet, and the blood treatment module has a pump to draw product medicament from the product medicament outlet. The blood treatment module has a self-contained replaceable fluid circuit for receiving product medicament from the medicament proportioning module and conveying through a blood treatment device thereby generating waste medicament, the replaceable fluid circuit is connected directly to a drain outlet for disposal of waste medicament without the waste medicament passing through the medicament proportioning module.

Variations of the twenty-fourth embodiments may be provided to form additional twenty-fourth embodiments in which the product medicament channel includes an accumulator with an expandable interior volume. Variations of the twenty-fourth embodiments may be provided to form additional twenty-fourth embodiments in which the accumulator is at least partly integrated in a replaceable cartridge. Variations of the twenty-fourth embodiments may be provided to form additional twenty-fourth embodiments in which the accumulator has a spring that is biased against expansion of an interior volume thereof. Variations of the twenty-fourth embodiments may be provided to form additional twenty-fourth embodiments in which the blood processing module includes a volumetric balancing system that draws medicament from the product medicament outlet at an unsteady rate that has a periodic component that is smoothed or canceled by the accumulator, such that rates of flow of the medicament proportioning module pumps responsive to the periodic component is diminished. Variations of the twenty-fourth embodiments may be provided to form additional twenty-fourth embodiments in which the blood processing module includes a volumetric balancing system that draws medicament from the product medicament outlet at an unsteady rate that has a periodic component that is canceled by the accumulator, such that rates of flow of the medicament proportioning module pumps responsive to the periodic component is eliminated.

According to twenty-fifth embodiments, the disclosed subject matter includes a medicament preparation system with a medicament generation system that has actuators and sensors positioned and shaped to interface a fluid circuit. The fluid circuit includes: (1) a first container containing a first concentrate connected for flow communication, through a first pumping tube segment, to a medicament supply line with an outlet, (2) a second container containing a second concentrate connected for flow communication, through a second pumping tube segment, to the medicament supply line, and (3) a water inlet line of the medicament supply line connected for flow communication, through a third pumping tube segment, to the medicament supply line. A sterile filter in the water inlet line is positioned to filter water entering the medicament supply line. The fluid circuit is a disposable replaceable component that is sterile and sealed from the external environment. The fluid circuit includes a first concentration measurement station positioned in the medicament supply line to measure a concentration of water mixed with the first concentrate. The fluid circuit includes a second concentration measurement station positioned in the medicament supply line to measure a concentration of water mixed with both the first concentrate and the second concentrate.

Variations of the twenty-fifth embodiments may be provided to form additional twenty-fifth embodiments in which the second concentration measurement station is positioned in the medicament supply line downstream of the first concentration measurement station. Variations of the twenty-fifth embodiments may be provided to form additional twenty-fifth embodiments in which the first and second concentration measurement stations each includes a temperature and conductivity sensor. Variations of the twenty-fifth embodiments may be provided to form additional twenty-fifth embodiments in which the first and second concentration measurement stations each includes two temperature sensors and two conductivity sensors. Variations of the twenty-fifth embodiments may be provided to form additional twenty-fifth embodiments that include a controller programmed to calculate, for each of the first and second concentration measurement stations, redundant concentration measurements based on the two temperature and the two conductivity sensors output of the each of the first and second concentration measurement stations and to generate an error output in response to a predetermined difference the redundant concentration measurements. Variations of the twenty-fifth embodiments may be provided to form additional twenty-fifth embodiments in which the first, second, and third pumping tube segments are supported by a circuit cartridge which orients, aligns, and exposes for access the first, second, and third pumping tube segments with respective actuators of a predefined medicament preparation device. Variations of the twenty-fifth embodiments may be provided to form additional twenty-fifth embodiments in which the circuit cartridge includes a fluid accumulator fluidly coupled between the water inlet line and the medicament supply line outlet end that includes a pressure-regulating urging element that biases a flexible wall of the accumulator such that transient changes of fluid pressure therein cause expansion of the volume of the accumulator.

Variations of the twenty-fifth embodiments may be provided to form additional twenty-fifth embodiments in which the fluid circuit is packaged with a box such that the circuit cartridge can be detached or removed from the box while leaving the first and second containers therein with lengths of connecting lines between the circuit cartridge and the box, thereby permitting the circuit cartridge to be installed in a position remote form a position where the box is installed. Variations of the twenty-fifth embodiments may be provided to form additional twenty-fifth embodiments in which the fluid circuit is packaged within a box such that the circuit cartridge can be removed from the box while leaving the first and second containers therein with lengths of connecting lines between the circuit cartridge and the box, thereby permitting the circuit cartridge to be installed in a position remote form a position where the box is installed. Variations of the twenty-fifth embodiments may be provided to form additional twenty-fifth embodiments in which the fluid circuit is attached to a box in such a way that the circuit cartridge can be detached from the box while leaving the first and second containers therein with lengths of connecting lines between the circuit cartridge and the box, thereby permitting the circuit cartridge to be installed in a position remote form a position where the box is installed. Variations of the twenty-fifth embodiments may be provided to form additional twenty-fifth embodiments in which the temperature sensor portion includes a flow chamber with a flat surface to permit a temperature sensor to be placed against the flat surface of a predefined sensor of the predefined medicament preparation device.

According to twenty-sixth embodiments, the disclosed subject matter includes a method for supplying medicament to a blood processing system. The method includes filtering water to increase a resistivity thereof to a level of at least 1 megohm-cm to generate high resistivity product water. The method further includes electrically heating the water resulting from the filtering includes continuously regulating a temperature thereof to maintain to a temperature calculated to maintain the body temperature of a patient receiving a blood treatment, the electrically heating occurring over a course of the blood treatment. The method further incudes adding medicament concentrate to water resulting from the electrically heating. The electrically heating generates a voltage difference between a patient and a heater used for the electrically heating. The method further includes dropping the voltage over a channel of high resistivity water product water whose dimensions are effective to reduce current through the channel to less than 50 microamperes and adding medicament concentrate to the high resistivity product water to generate a product medicament and fluidly and electrically interfacing the product medicament with a patient blood circuit connected to a patient undergoing a blood treatment.

Variations of the twenty-sixth embodiments may be provided to form additional twenty-sixth embodiments in which the electrically heating includes pulse-width modulating an electrical heater. Variations of the twenty-sixth embodiments may be provided to form additional twenty-sixth embodiments in which the generating a voltage difference includes capacitively coupling a conducting circuit with fluid, in a fluid channel, that is fluidly coupled to the product medicament. Variations of the twenty-sixth embodiments may be provided to form additional twenty-sixth embodiments in which the filtering includes deionizing tap water in a deionization filter bed. Variations of the twenty-sixth embodiments may be provided to form additional twenty-sixth embodiments in which the filtering water increases a resistivity thereof to a level of at least 3 megohm-cm. Variations of the twenty-sixth embodiments may be provided to form additional twenty-sixth embodiments in which the filtering water increases a resistivity thereof to a level of at least 5 megohm-cm. Variations of the twenty-sixth embodiments may be provided to form additional twenty-sixth embodiments in which the filtering water increases a resistivity thereof to a level of at least 10 megohm-cm.

Variations of the twenty-sixth embodiments may be provided to form additional twenty-sixth embodiments in which the electrically heating places the high resistivity water in direct contact with a permanent electrical heater which is not replaced between uses, the electrically heating is followed by sterile-filtering the high resistivity product water. Variations of the twenty-sixth embodiments may be provided to form additional twenty-sixth embodiments in which the adding medicament includes proportioning the high resistivity water with medicament concentrate using feedback control with a control target of a measured predefined conductivity. Variations of the twenty-sixth embodiments may be provided to form additional twenty-sixth embodiments in which the adding medicament includes proportioning the high resistivity water with medicament concentrate through a fluid circuit that is 100% disposable.

According to twenty-seventh embodiments, the disclosed subject matter includes a system for providing medicament. A sterile circuit with multiple fluid circuits is interconnected to permit two or more component fluids to be combined to form a product medicament, the multiple fluid circuits has respective inlets for each of the two or more component fluids and a common outlet, the common outlet is fluidly connected by the sterile circuit to the respective inlets to provide a combined medicament product. The sterile circuit defines a sterile barrier such that internal fluid compartment defined by the multiple fluid circuits is isolated from an external environment, includes the respective inlets. Variations of the twenty-seventh embodiments may be provided to form additional twenty-seventh embodiments in which the sterile circuit includes pumping portions.

Variations of the twenty-seventh embodiments may be provided to form additional twenty-seventh embodiments in which the sterile barrier includes a sterilizing filter positioned at at least one of the respective inlets and has a pore size sufficiently small to filter and sterilize a respective one of the component fluids that may flow therethrough Variations of the twenty-seventh embodiments may be provided to form additional twenty-seventh embodiments in which the multiple fluid circuits include a respective pumping tube segment for each of the component fluids, each is joined to the common outlet. Variations of the twenty-seventh embodiments may be provided to form additional twenty-seventh embodiments that include a water purification plant connected to the sterile circuit to deliver water, the water is one of the two or more component fluids, the water purification plant is connected through one of the respective inlets, the one of the respective inlets has a sterilizing filter with a pore size sufficiently small to filter and sterilize water flowing into the sterile circuit through the one of the respective inlets. Variations of the twenty-seventh embodiments may be provided to form additional twenty-seventh embodiments that include a controller the controller is adapted to receive prior use data indicating a period of time since the multiple fluid circuits' interior volumes were first wetted and to output a command signal indicating whether the sterile circuit is safe to use. Variations of the twenty-seventh embodiments may be provided to form additional twenty-seventh embodiments that include a data reader, connected to the controller, that sends status data to the controller, the status data is derived at least in part on data from stored data read by the data reader from a data store attached to the sterile circuit. Variations of the twenty-seventh embodiments may be provided to form additional twenty-seventh embodiments in which the stored data indicates a type of the sterile circuit. Variations of the twenty-seventh embodiments may be provided to form additional twenty-seventh embodiments in which the stored data indicates a date and time when the sterile circuit was first wetted. Variations of the twenty-seventh embodiments may be provided to form additional twenty-seventh embodiments that include a treatment device connected to the common outlet and is of a type that requires a sterile medicament. Variations of the twenty-seventh embodiments may be provided to form additional twenty-seventh embodiments in which the treatment device includes a blood processing treatment device. Variations of the twenty-seventh embodiments may be provided to form additional twenty-seventh embodiments in which the treatment device includes an extracorporeal blood treatment device. Variations of the twenty-seventh embodiments may be provided to form additional twenty-seventh embodiments in which the sterile circuit internal fluid compartment is sterile as a result of the sterile circuit is a product of manufacture that includes sealing a disposable unit and sterilizing it. Variations of the twenty-seventh embodiments may be provided to form additional twenty-seventh embodiments in which the sterile circuit internal fluid compartment is sterile as a result of the sterile circuit is sterilized and used for a limited time to prevent colonization of bacteria. Variations of the twenty-seventh embodiments may be provided to form additional twenty-seventh embodiments in which the sterile circuit internal fluid compartment is sterile as a result of the sterile circuit is a sterile disposable. Variations of the twenty-seventh embodiments may be provided to form additional twenty-seventh embodiments in which the sterile circuit internal fluid compartment is sterile as a result of a sterilization process. Variations of the twenty-seventh embodiments may be provided to form additional twenty-seventh embodiments in which the sterile circuit includes sensor and pumping portions positioned and oriented to engage with a predefined medicament preparation module that controls the flow of fluid therethrough.

According to twenty-eighth embodiments, the disclosed subject matter includes a system for providing a continuous flow of medicament to a blood treatment system. A sterile circuit defines an internal fluid compartment that is sterile. And sterility maintenance mechanisms for providing medicament to a blood treatment system while maintaining a sterile condition of the internal fluid compartment. The sterility maintenance mechanism includes a sterile barrier that prevents ingress of contaminants into the internal fluid compartment. The sterile barrier includes impermeable walls defining the internal fluid compartment. At least one sterile filter blocks contaminants from any incoming fluid flowing into the internal fluid compartment from transferring a contaminant thereinto. A control mechanism permits the use of the sterile circuit for supplying medicament to a blood treatment system over multiple treatments and limits the number of times or time between uses of the sterile circuit for supplying medicament to a blood treatment system.

Variations of the twenty-eighth embodiments may be provided to form additional twenty-eighth embodiments in which the sterile circuit has inlets for two or more fluids that are interconnected to fluidly connect to a common outlet for the supply of medicament, such that the two or more fluids may be mixed thereby. Variations of the twenty-eighth embodiments may be provided to form additional twenty-eighth embodiments in which the control mechanism is responsive to sterility-enforcement data indicating a time since the sterile circuit was first used for preparing medicament, a volume of fluid processed by the sterile circuit, a date of manufacture, a lot number, or a type of the sterile circuit. Variations of the twenty-eighth embodiments may be provided to form additional twenty-eighth embodiments in which the sterility-enforcement data is stored on a data carrier attached to the sterile circuit.

According to twenty-ninth embodiments, the disclosed subject matter includes a method of performing an extracorporeal blood treatment. The method includes, at a first time, flowing component fluids to form a medicament into a sterile compartment, the flowing includes wetting the sterile compartment. The method further includes mixing the component fluids to form a medicament and supplying the same, at the first time, to a medical treatment apparatus for providing a medical treatment. The method further includes, at a second time, with a controller and responsively to use-permission data, permitting or preventing a further flowing component fluids to form a medicament into the sterile compartment. The method further includes at the second time, upon initially preventing the further flowing, permitting a further flowing component fluids to form a medicament into the same or a new sterile compartment after a replacement or sterilization of the sterile compartment so as to ensure sterility thereof, the permitting includes verifying that the sterile compartment has been replaced or sterilized. The use-permission data is indicative of a time since the sterile compartment was first wetted for preparing medicament, a volume of fluid processed by the sterile compartment, a date of manufacture of the sterile compartment, a lot number of the sterile compartment, or a type of the sterile compartment.

Variations of the twenty-ninth embodiments may be provided to form additional twenty-ninth embodiments that include measuring a conductivity and temperature of a mixture resulting from the mixing.

According to thirtieth embodiments, the disclosed subject matter includes a system for inline medicament mixing, comprising: a water purification plant connected at a tap water inlet thereof to water mains supply providing tap water. An air break is connected to receive water from the tap water inlet under control of a control valve connected to a controller. The air break includes an air break chamber with at least one level sensor, the controller controlling the control valve to maintain a predefined water level or range of water levels within the air break chamber. The air break chamber has an overflow outlet that permits water to flow out of the air break chamber if a pressure or water level in the air break chamber exceeds a predetermined magnitude, such that back flow into the tap water inlet is prevented. The water purification plant has a preparation pump controlled by the controller to pump water, on-demand, from the air break chamber and supply filtered water to a product water outlet and controlled by the controller to maintain a predefined pressure causing water to flow through filters of the water purification plant. A vent in the air break chamber permits air to flow out of the air break chamber to permit the water level to rise in the absence of flow thereinto from the tap water inlet. A medicament proportioning system, has a water pump, connected to the product water outlet, the medicament proportioning system water pump drawing water on-demand from the product water outlet.

According to thirty-first embodiments, the disclosed subject matter includes a system for inline medicament mixing. A water purification plant is connected at a tap water inlet thereof to water mains supply providing tap water. The thirty-first embodiment further includes a controller and a control valve. An air break is connected to receive water from the tap water inlet under control of the control valve connected to the controller. The air break includes an air break chamber with at least one level sensor, the controller controlling the control valve to maintain a predefined water level or range of water levels within the air break chamber. The air break chamber has an outlet from which water is drawn from the air break chamber and passed through filters to generate product water. The air break chamber has an overflow outlet that permits water to flow out of the air break chamber if a pressure or water level in the air break chamber exceeds a predetermined magnitude, such that back flow into the tap water inlet is prevented. A medicament proportioning portion has a water pump, connected to the product water outlet, the medicament proportioning portion water pump drawing water on-demand from the product water outlet.

Variations of the thirty-second embodiments may be provided to form additional thirty-second embodiments in which the controller controls the air break water level below a level of the overflow outlet. Variations of the thirty-second embodiments may be provided to form additional thirty-second embodiments in which the water mains supply is under a positive pressure. Variations of the thirty-second embodiments may be provided to form additional thirty-second embodiments in which the medicament proportioning portion water pump operates at a speed determined by a medicament demand signal from a treatment device. Variations of the thirty-second embodiments may be provided to form additional thirty-second embodiments in which the wherein the medicament proportioning portion water pump operates at a speed determined by volume drawn therefrom from by a treatment device. Variations of the thirty-second embodiments may be provided to form additional thirty-second embodiments in which the medicament demand signal is mechanical. Variations of the thirty-second embodiments may be provided to form additional thirty-second embodiments in which the medicament demand signal is a pressure signal. Variations of the thirty-second embodiments may be provided to form additional thirty-second embodiments in which the medicament demand signal is an electronic data signal. Variations of the thirty-second embodiments may be provided to form additional thirty-second embodiments that include a water leakage detector arranged to detect water exiting the air break chamber from overflow outlet and the controller.

Further variations of the thirty-second embodiments may be provided to form additional thirty-second embodiments in which the controller is a programmable controller programmed to output an error signal when water is detected by the water leakage detector. Variations of the thirty-second embodiments may be provided to form additional thirty-second embodiments that include a conductivity sensor in a water flow path of the air break. Variations of the thirty-second embodiments may be provided to form additional thirty-second embodiments that include a conductivity sensor in the air break chamber. Variations of the thirty-second embodiments may be provided to form additional thirty-second embodiments in which the air break chamber is generally cylindrical in shape. Variations of the thirty-second embodiments may be provided to form additional thirty-second embodiments in which the at least one level sensor is at least two level sensors each located at respective positions of the air break chamber. Variations of the thirty-second embodiments may be provided to form additional thirty-second embodiments in which the at least one level sensor is at least three level sensors each located at respective positions of the air break chamber. Variations of the thirty-second embodiments may be provided to form additional thirty-second embodiments in which the controller is a programmable controller. Variations of the thirty-second embodiments may be provided to form additional thirty-second embodiments that include an extracorporeal blood treatment system that draws product medicament from the medicament proportioning portion on-demand, which demand the medicament proportioning portion detects and satisfies, and the medicament proportioning portion draws water from the water purification plant on-demand, which the controller satisfies by maintaining a level of water in the air break chamber. Variations of the thirty-second embodiments may be provided to form additional thirty-second embodiments in which the medicament proportioning portion draws water from the water purification plant on-demand, which the controller satisfies by maintaining a level of water in the air break chamber. Variations of the thirty-second embodiments may be provided to form additional thirty-second embodiments in which the air break chamber outlet supplies water at a pressure determined only by a weight of a water column of water in the air break chamber, whereby pressure from the mains, includes fluctuations thereof, are not transmitted downstream to the filters or the medicament proportioning portion.

According to thirty-third embodiments, the disclosed subject matter includes a fluid circuit for a predefined medicament preparation system having actuators and sensors that are interoperable with the fluid circuit. The fluid circuit includes a sterile circuit with multiple fluid circuits interconnected to permit two or more component fluids to be combined to form a product medicament. The multiple fluid circuits having respective inlets for each of said two or more component fluids and a common outlet, the common outlet being fluidly connected by the sterile circuit to the respective inlets to provide a combined medicament product. The sterile circuit defines a sterile barrier such that internal fluid compartment defined by said multiple fluid circuits is isolated from an external environment, including said respective inlets. One or more concentration measurement stations include fluid conductivity and temperature measurement portions which are positioned within the fluid circuit to detect conductivity and temperature of mixtures of the two or more component fluids and further positioned, when the sterile circuit is loaded in the predefined medicament preparation system, to engage with sensor components thereof to generate conductivity and temperature signals of said mixtures.

Variations of the thirty-third embodiments may be provided to form additional thirty-third embodiments in which the sterile barrier includes a sterilizing filter positioned at at least one of said respective inlets and having a pore size sufficiently small to filter and sterilize a respective one of said component fluids that may flow therethrough. Variations of the thirty-third embodiments may be provided to form additional thirty-third embodiments in which the multiple fluid circuits include a respective pumping tube segment for each of said component fluids, each being joined to the common outlet. Variations of the thirty-third embodiments may be provided to form additional thirty-third embodiments in which one of said respective inlets includes a water inlet connectable to a water purification plant to deliver water as one of said two or more component fluids, the one of said respective inlets having a sterilizing filter with a pore size sufficiently small to filter and sterilize water flowing into said sterile circuit through said one of said respective inlets. Variations of the thirty-third embodiments may be provided to form additional thirty-third embodiments that include a data reader, attached to said sterile circuit, storing data indicating data indicating at least one characteristic of a usage history of said sterile circuit. Variations of the thirty-third embodiments may be provided to form additional thirty-third embodiments that include a data reader, attached to said sterile circuit, storing data indicating data indicating a type of said sterile circuit. Variations of the thirty-third embodiments may be provided to form additional thirty-third embodiments that include a data reader, attached to said sterile circuit, storing data indicating a first time said sterile circuit was first wetted. Variations of the thirty-third embodiments may be provided to form additional thirty-third embodiments in which the sterile circuit internal fluid compartment is sterile as a result of said sterile circuit being a sterile disposable.

According to thirty-fourth embodiments, the disclosed subject matter includes a system for providing medicament with a sterile circuit with multiple fluid circuits interconnected to permit two or more component fluids to be combined to form a product medicament, the multiple fluid circuits having respective inlets for each of said two or more component fluids and a common outlet, the common outlet being fluidly connected by the sterile circuit to the respective inlets to provide a combined medicament product. The sterile circuit defines a sterile barrier such that internal fluid compartment defined by said multiple fluid circuits is isolated from an external environment, including said respective inlets. The sterile circuit includes one or more concentration measurement stations including fluid conductivity and temperature measurement portions. A controller has sensor components to generate conductivity and temperature signals, the sensor components engaging with conductivity and temperature measurement portions of the sterile circuit that are positioned to detect temperature and conductivity of mixtures of said two or more components.

Variations of the thirty-fourth embodiments may be provided to form additional thirty-fourth embodiments in which the sterile barrier includes a sterilizing filter positioned at at least one of said respective inlets and having a pore size sufficiently small to filter and sterilize a respective one of said component fluids that may flow therethrough. Variations of the thirty-fourth embodiments may be provided to form additional thirty-fourth embodiments in which the multiple fluid circuits include a respective pumping tube segment for each of said component fluids, each being joined to the common outlet. Variations of the thirty-fourth embodiments may be provided to form additional thirty-fourth embodiments that include a water purification plant connected to said sterile circuit to deliver water, said water being one of said two or more component fluids, the water purification plant being connected through one of said respective inlets, the one of said respective inlets having a sterilizing filter with a pore size sufficiently small to filter and sterilize water flowing into said sterile circuit through said one of said respective inlets. Variations of the thirty-fourth embodiments may be provided to form additional thirty-fourth embodiments that include a controller the controller being adapted to receive prior use data indicating a period of time since the multiple fluid circuits interior volumes were first wetted and to output a command signal indicating whether the sterile circuit is safe to use. Variations of the thirty-fourth embodiments may be provided to form additional thirty-fourth embodiments that include a data reader, connected to the controller, that sends status data to the controller, the status data being derived at least in part on data from stored data read by the data reader from a data store attached to the sterile circuit. Variations of the thirty-fourth embodiments may be provided to form additional thirty-fourth embodiments in which the stored data indicates a type of said sterile circuit. Variations of the thirty-fourth embodiments may be provided to form additional thirty-fourth embodiments in which the stored data indicates a date and time when the sterile circuit was first wetted. Variations of the thirty-fourth embodiments may be provided to form additional thirty-fourth embodiments that include a treatment device connected to the common outlet and being of a type that requires a sterile medicament. Variations of the thirty-fourth embodiments may be provided to form additional thirty-fourth embodiments in which the treatment device includes a blood processing treatment device. Variations of the thirty-fourth embodiments may be provided to form additional thirty-fourth embodiments in which the treatment device includes an extracorporeal blood treatment device. Variations of the thirty-fourth embodiments may be provided to form additional thirty-fourth embodiments in which the sterile circuit internal fluid compartment is sterile as a result of said sterile circuit being a product of manufacture that includes sealing a disposable unit and sterilizing it. Variations of the thirty-fourth embodiments may be provided to form additional thirty-fourth embodiments in which the sterile circuit internal fluid compartment is sterile as a result of said sterile circuit being sterilized and used for a limited time to prevent colonization of bacteria. Variations of the thirty-fourth embodiments may be provided to form additional thirty-fourth embodiments in which the sterile circuit internal fluid compartment is sterile as a result of said sterile circuit being a sterile disposable.

In further variations of the system the sterile circuit internal fluid compartment is sterile as a result of a sterilization process. Variations of the thirty-fourth embodiments may be provided to form additional thirty-fourth embodiments in which the sterile circuit includes sensor and pumping portions positioned and oriented to engage with a predefined medicament preparation module that controls the flow of fluid therethrough.

A fluid conductivity measurement system can be included in an of the embodiments which three or more conductive electrodes positioned along a fluid path are used to measure fluid conductivity form two or more conduction paths for the measurement of conductivity of a same fluid.

According to thirty-fifth embodiments, the disclosed subject matter includes a conductivity measurement device with a fluid channel with three or more electrodes positioned to contact a fluid flowing in said fluid channel. A conductivity measurement circuit is controlled by a controller, the controller programmed to control switches to pass a current between a first pair of the three or more electrodes and measure a first voltage drop across said first pair at a first time and to pass a current between a second pair of the three or more electrodes and measure a second voltage drop across said second pair at a second time, where the first pair and the second pair include a same one of the three or more electrodes and the first and second times are sufficiently contemporaneous as to correspond to an identical fluid flowing through said channel.

Variations of the thirty-fifth embodiments may be provided to form additional thirty-fifth embodiments in which the first pair is positioned at opposite ends of a first enlarged section of said flow channel. Variations of the thirty-fifth embodiments may be provided to form additional thirty-fifth embodiments in which of the second pair is positioned at an end of a second enlarged section of said flow channel that is interconnected with the first. Variations of the thirty-fifth embodiments may be provided to form additional thirty-fifth embodiments in which the controller is adapted to calculate a single fluid conductivity responsively to the first and second voltage drops.

According to thirty-sixth embodiments, the disclosed subject matter includes a fluid circuit for preparation of a medicament for renal replacement therapy. A concentrate container containing acid concentrate is connected for flow communication, through a first pumping tube segment, to a medicament supply line that has been capped and sterile-sealed at an outlet end thereof. A bicarbonate cartridge containing dry bicarbonate buffer compound is of a type that admits water in an cartridge inlet thereby forming a saturated bicarbonate solution which is received at a cartridge outlet, the cartridge outlet being connected for flow communication, through a second pumping tube segment, to the medicament supply line. A water inlet line is connected for flow communication, through a third pumping tube segment, to the medicament supply line and connected for flow communication to the bicarbonate cartridge inlet. The first, second, and third pumping tube segments are supported by a circuit cartridge which orients, aligns, and exposes for access the first, second, and third pumping tube segments with respective actuators of a predefined medicament preparation device. The circuit cartridge contains a first concentration sensor station positioned in the medicament supply line downstream of a first junction where a first of the first and second pumping tube segments connects to the medicament supply line. The circuit cartridge contains a second concentration sensor station positioned in the medicament supply line downstream of both the first junction and a second junction where a second of the first and second pumping tube segments connects to the medicament supply line.

Variations of the thirty-sixth embodiments may be provided to form additional thirty-sixth embodiments in which the water inlet line is capped and sterile-sealed and the entire fluid circuit is sterile. Variations of the thirty-sixth embodiments may be provided to form additional thirty-sixth embodiments in which the circuit cartridge includes a fluid accumulator fluidly coupled between the water inlet line and the medicament supply line outlet end that includes a pressure-regulating urging element that biases a flexible wall of the accumulator such that transient changes of fluid pressure therein cause expansion of the volume of the accumulator. Variations of the thirty-sixth embodiments may be provided to form additional thirty-sixth embodiments in which the fluid circuit is packaged with a box such that the circuit cartridge can be detached or removed from the box while leaving the concentrate container and bicarbonate cartridge intact therein with lengths of connecting lines between the circuit cartridge and the box, thereby permitting the circuit cartridge to be installed in a position remote form a position where the box is installed. Variations of the thirty-sixth embodiments may be provided to form additional thirty-sixth embodiments in which the fluid circuit is packaged within a box such that the circuit cartridge can be removed from the box while leaving the concentrate container and bicarbonate cartridge intact therein with lengths of connecting lines between the circuit cartridge and the box, thereby permitting the circuit cartridge to be installed in a position remote form a position where the box is installed. Variations of the thirty-sixth embodiments may be provided to form additional thirty-sixth embodiments in which the fluid circuit is attached to a box in such a way that the circuit cartridge can be detached from the box while leaving the concentrate container and bicarbonate cartridge intact therein with lengths of connecting lines between the circuit cartridge and the box, thereby permitting the circuit cartridge to be installed in a position remote form a position where the box is installed. Variations of the thirty-sixth embodiments may be provided to form additional thirty-sixth embodiments in which the box is principally of cardboard. Variations of the thirty-sixth embodiments may be provided to form additional thirty-sixth embodiments in which each of the concentration sensor stations includes a liquid conductivity sensor and temperature sensor portions. Variations of the thirty-sixth embodiments may be provided to form additional thirty-sixth embodiments in which the temperature sensor portion includes a flow chamber with a flat surface to permit a temperature sensor to be placed against the flat surface of a predefined sensor of the predefined medicament preparation device. Variations of the thirty-sixth embodiments may be provided to form additional thirty-sixth embodiments in which each of the concentration stations includes, connected in series, two independent conductivity sensors and two independent temperature sensor portions. Variations of the thirty-sixth embodiments may be provided to form additional thirty-sixth embodiments in which the medicament supply line includes a waste outlet branch that is in direct fluid communication with the accumulator, the waste outlet line being capped and sterile-sealed, the medicament supply line outlet line and waste outlet branches having pinching portions supported in an open section of the circuit cartridge to permit access by pinching actuators.

According to thirty-seventh embodiments, the disclosed subject matter includes a fluid circuit for preparation of a medicament for renal replacement therapy. A first container containing acid concentrate is connected for flow communication, through a first pumping tube segment, to a medicament supply line that has been capped and sterile-sealed at an outlet end thereof. A second container contains a buffer concentrate connected for flow communication, through a second pumping tube segment, to the medicament supply line. A water inlet line is connected for flow communication, through a third pumping tube segment, to the medicament supply line. The first, second, and third pumping tube segments are supported by a circuit cartridge which orients, aligns, and exposes for access the first, second, and third pumping tube segments with respective actuators of a predefined medicament preparation device. The circuit cartridge contains a first concentration sensor station positioned in the medicament supply line downstream of a first junction where a first of the first and second pumping tube segments connects to the medicament supply line. The circuit cartridge contains a second concentration sensor station positioned in the medicament supply line downstream of both the first junction and a second junction where a second of the first and second pumping tube segments connects to the medicament supply line.

Variations of the thirty-seventh embodiments may be provided to form additional thirty-seventh embodiments in which the circuit cartridge includes a fluid accumulator fluidly coupled between the water inlet line and the medicament supply line outlet end that includes a pressure-regulating urging element that biases a flexible wall of the accumulator such that transient changes of fluid pressure therein cause expansion of the volume of the accumulator. Variations of the thirty-seventh embodiments may be provided to form additional thirty-seventh embodiments in which the fluid circuit is packaged with a box such that the circuit cartridge can be detached or removed from the box while leaving the first and second containers therein with lengths of connecting lines between the circuit cartridge and the box, thereby permitting the circuit cartridge to be installed in a position remote form a position where the box is installed. Variations of the thirty-seventh embodiments may be provided to form additional thirty-seventh embodiments in which the fluid circuit is packaged within a box such that the circuit cartridge can be removed from the box while leaving the first and second containers therein with lengths of connecting lines between the circuit cartridge and the box, thereby permitting the circuit cartridge to be installed in a position remote form a position where the box is installed. Variations of the thirty-seventh embodiments may be provided to form additional thirty-seventh embodiments in which the fluid circuit is attached to a box in such a way that the circuit cartridge can be detached from the box while leaving the first and second containers therein with lengths of connecting lines between the circuit cartridge and the box, thereby permitting the circuit cartridge to be installed in a position remote form a position where the box is installed. Variations of the thirty-seventh embodiments may be provided to form additional thirty-seventh embodiments in which the box is principally of cardboard. Variations of the thirty-seventh embodiments may be provided to form additional thirty-seventh embodiments in which wherein each of the concentration sensor stations includes a liquid conductivity sensor and temperature sensor portions. Variations of the thirty-seventh embodiments may be provided to form additional thirty-seventh embodiments in which the temperature sensor portion includes a flow chamber with a flat surface to permit a temperature sensor to be placed against the flat surface of a predefined sensor of the predefined medicament preparation device. Variations of the thirty-seventh embodiments may be provided to form additional thirty-seventh embodiments in which each of the concentration stations includes, connected in series, two independent conductivity sensors and two independent temperature sensor portions. Variations of the thirty-seventh embodiments may be provided to form additional thirty-seventh embodiments in which the medicament supply line includes a waste outlet branch that is in direct fluid communication with the accumulator, the waste outlet line being capped and sterile-sealed, the medicament supply line outlet line and waste outlet branches having pinching portions supported in an open section of the circuit cartridge to permit access by pinching actuators. Variations of the thirty-seventh embodiments may be provided to form additional thirty-seventh embodiments in which the water inlet line is capped and sterile-sealed and the entire fluid circuit is sterile.

According to thirty-eighth embodiments, the disclosed embodiments include a medicament preparation system. A medicament generation system has actuators and sensors positioned and shaped to interface a fluid circuit. The fluid includes a first container containing acid concentrate connected for flow communication, through a first pumping tube segment, to a medicament supply line that has been capped and sterile-sealed at an outlet end thereof;

a second container containing a buffer concentrate connected for flow communication, through a second pumping tube segment, to the medicament supply line; and a water inlet line of the medicament supply line, connected for flow communication, through a third pumping tube segment, to the medicament supply line.

The fluid circuit is a disposable replaceable component and that forms a sterile unit that is sealed against ingress of contaminants from the external environment. A water purification plant is connectable to the inlet, the water purification plant has an outlet that is connectable to the inlet to receive purified water from through the water inlet line. A controller has a processor configured to calculate a permissible life for utilization thereof responsively to at least one of a volume of fluid passing through the medicament supply line, a volume of water passing through the water inlet, and a length of time since water first flowed through the water inlet.

Variations of the thirty-eighth embodiments may be provided to form additional thirty-eighth embodiments that include a sterile filter in the water inlet line positioned to filter all water entering the medicament supply line. Variations of the thirty-eighth embodiments may be provided to form additional thirty-eighth embodiments in which the fluid circuit is a disposable replaceable component that is sterile. Variations of the thirty-eighth embodiments may be provided to form additional thirty-eighth embodiments in which the water purification plant is connectable to the inlet through a sterile filter positioned in an outlet thereof, the sterile filter having a pore size that ensures sterility of the water entering the water inlet line. Variations of the thirty-eighth embodiments may be provided to form additional thirty-eighth embodiments in which the water purification plant is connectable to the inlet through a sterile filter positioned in an outlet thereof, the sterile filter having a pore size that ensures sterility of the water entering the water inlet line. Variations of the thirty-eighth embodiments may be provided to form additional thirty-eighth embodiments in which the water purification plant is connectable to the inlet through a sterile filter positioned in an outlet thereof, the sterile filter having a pore size that ensures sterility of the water entering the water inlet line. Variations of the thirty-eighth embodiments may be provided to form additional thirty-eighth embodiments in which the first, second, and third pumping tube segments are supported by a circuit cartridge which orients, aligns, and exposes for access the first, second, and third pumping tube segments with respective actuators of a predefined medicament preparation device. Variations of the thirty-eighth embodiments may be provided to form additional thirty-eighth embodiments in which the circuit cartridge contains a first concentration sensor station positioned in the medicament supply line downstream of a first junction where a first of the first and second pumping tube segments connects to the medicament supply line. Variations of the thirty-eighth embodiments may be provided to form additional thirty-eighth embodiments in which the circuit cartridge contains a second concentration sensor station positioned in the medicament supply line downstream of both the first junction and a second junction where a second of the first and second pumping tube segments connects to the medicament supply line. Variations of the thirty-eighth embodiments may be provided to form additional thirty-eighth embodiments in which the circuit cartridge contains redundant sensor stations positioned in the medicament supply line downstream of both the first junction and a second junction. Variations of the thirty-eighth embodiments may be provided to form additional thirty-eighth embodiments in which the circuit cartridge includes a fluid accumulator fluidly coupled between the water inlet line and the medicament supply line outlet end that includes a pressure-regulating urging element that biases a flexible wall of the accumulator such that transient changes of fluid pressure therein cause expansion of the volume of the accumulator. Variations of the thirty-eighth embodiments may be provided to form additional thirty-eighth embodiments in which the fluid circuit is packaged with a box such that the circuit cartridge can be detached or removed from the box while leaving the first and second containers therein with lengths of connecting lines between the circuit cartridge and the box, thereby permitting the circuit cartridge to be installed in a position remote form a position where the box is installed. Variations of the thirty-eighth embodiments may be provided to form additional thirty-eighth embodiments in which the fluid circuit is packaged within a box such that the circuit cartridge can be removed from the box while leaving the first and second containers therein with lengths of connecting lines between the circuit cartridge and the box, thereby permitting the circuit cartridge to be installed in a position remote form a position where the box is installed. Variations of the thirty-eighth embodiments may be provided to form additional thirty-eighth embodiments in which the fluid circuit is attached to a box in such a way that the circuit cartridge can be detached from the box while leaving the first and second containers therein with lengths of connecting lines between the circuit cartridge and the box, thereby permitting the circuit cartridge to be installed in a position remote form a position where the box is installed. Variations of the thirty-eighth embodiments may be provided to form additional thirty-eighth embodiments in which the box is principally of cardboard. Variations of the thirty-eighth embodiments may be provided to form additional thirty-eighth embodiments in which each of the concentration sensor stations includes a liquid conductivity sensor and temperature sensor portions. Variations of the thirty-eighth embodiments may be provided to form additional thirty-eighth embodiments in which the temperature sensor portion includes a flow chamber with a flat surface to permit a temperature sensor to be placed against the flat surface of a predefined sensor of the predefined medicament preparation device. Variations of the thirty-eighth embodiments may be provided to form additional thirty-eighth embodiments in which each of the concentration stations includes, connected in series, two independent conductivity sensors and two independent temperature sensor portions. Variations of the thirty-eighth embodiments may be provided to form additional thirty-eighth embodiments in which the medicament supply line includes a waste outlet branch that is in direct fluid communication with the accumulator, the waste outlet line being capped and sterile-sealed, the medicament supply line outlet line and waste outlet branches having pinching portions supported in an open section of the circuit cartridge to permit access by pinching actuators.

According to thirty-ninth embodiments, the disclosed subject matter includes system for providing medicament. A circuit component with multiple fluid circuits is interconnected to permit two or more component fluids to be combined to form a product medicament, the multiple fluid circuits having respective inlets for each of the two or more component fluids and a common outlet, the common outlet being fluidly connected by the circuit component to the respective inlets to provide a combined medicament product. The circuit component defines a sealed internal volume such that internal fluid compartment defined by the multiple fluid circuits is isolated from an external environment, including the respective inlets.

Variations of the thirty-ninth embodiments may be provided to form additional thirty-ninth embodiments in which the circuit component includes one or more concentration measurement stations including fluid conductivity and temperature measurement portions which are positioned within the fluid circuit to detect conductivity and temperature of mixtures of the two or more component fluids and further positioned, when the circuit component is loaded in a predefined medicament preparation apparatus, to engage with sensor components to generate conductivity and temperature signals of the mixtures. Variations of the thirty-ninth embodiments may be provided to form additional thirty-ninth embodiments in which the internal volume is sterile. Variations of the thirty-ninth embodiments may be provided to form additional thirty-ninth embodiments in which the circuit component multiple fluid circuits define a sterile barrier that includes a sterilizing filter positioned at at least one of the respective inlets and having a pore size sufficiently small to filter and sterilize a respective one of the component fluids that may flow therethrough. Variations of the thirty-ninth embodiments may be provided to form additional thirty-ninth embodiments in which the multiple fluid circuits include a respective Variations of the thirty-ninth embodiments may be provided to form additional thirty-ninth embodiments that include a water purification plant connected to the circuit component to deliver water, the water being one of the two or more component fluids, the water purification plant being connected through one of the respective inlets, the one of the respective inlets having a sterilizing filter with a pore size sufficiently small to filter and sterilize water flowing into the circuit component through the one of the respective inlets. Variations of the thirty-ninth embodiments may be provided to form additional thirty-ninth embodiments that include a controller the controller being adapted to receive prior use data indicating a period of time since the multiple fluid circuits interior volumes were first wetted and to output a command signal indicating whether the circuit component is safe to use. Variations of the thirty-ninth embodiments may be provided to form additional thirty-ninth embodiments that include a data reader, connected to the controller, that sends status data to the controller, the status data being derived at least in part on data from stored data read by the data reader from a data store attached to the circuit component. Variations of the thirty-ninth embodiments may be provided to form additional thirty-ninth embodiments in which the stored data indicates a type of the circuit component. Variations of the thirty-ninth embodiments may be provided to form additional thirty-ninth embodiments in which the stored data indicates a date and time when the sterile circuit was first wetted. Variations of the thirty-ninth embodiments may be provided to form additional thirty-ninth embodiments that include a treatment device connected to the common outlet and being of a type that requires a sterile medicament. Variations of the thirty-ninth embodiments may be provided to form additional thirty-ninth embodiments in which the treatment device includes a blood processing treatment device. Variations of the thirty-ninth embodiments may be provided to form additional thirty-ninth embodiments in which the treatment device includes an extracorporeal blood treatment device. Variations of the thirty-ninth embodiments may be provided to form additional thirty-ninth embodiments in which the circuit component internal fluid compartment is sterile as a result of the circuit component being a product of manufacture that includes sealing a disposable unit and sterilizing it. Variations of the thirty-ninth embodiments may be provided to form additional thirty-ninth embodiments in which the circuit component internal fluid compartment is sterile as a result of the circuit component being sterilized and used for a limited time to prevent colonization of bacteria. Variations of the thirty-ninth embodiments may be provided to form additional thirty-ninth embodiments in which the circuit component internal fluid compartment is sterile as a result of the circuit component being a sterile disposable. Variations of the thirty-ninth embodiments may be provided to form additional thirty-ninth embodiments in which the circuit component internal fluid compartment is sterile as a result of a sterilization process. Variations of the thirty-ninth embodiments may be provided to form additional thirty-ninth embodiments in which the circuit component includes sensor and pumping portions positioned and oriented to engage with a predefined medicament preparation module that controls the flow of fluid therethrough.

According to fortieth embodiments, the disclosed subject matter includes a fluid circuit for a predefined medicament preparation system having actuators and sensors that are interoperable with the fluid circuit, the fluid circuit. A circuit component with multiple fluid circuits is interconnected to permit two or more component fluids to be combined to form a product medicament, the multiple fluid circuits having respective inlets for each of the two or more component fluids and a common outlet, the common outlet being fluidly connected by the circuit component to the respective inlets to provide a combined medicament product The circuit component defines a sealed internal fluid compartment defined by the multiple fluid circuits is isolated from an external environment, including the respective inlets. One or more concentration measurement stations include fluid conductivity and temperature measurement portions which are positioned within the fluid circuit to detect conductivity and temperature of mixtures of the two or more component fluids and further positioned, when the circuit component is loaded in the predefined medicament preparation system, to engage with sensor components thereof to generate conductivity and temperature signals of the mixtures.

Variations of the fortieth embodiments may be provided to form additional fortieth embodiments in which the sealed internal fluid compartment is sealed against ingress of contaminants by a sterilizing filter positioned at at least one of the respective inlets and having a pore size sufficiently small to filter and sterilize a respective one of the component fluids that may flow therethrough. Variations of the fortieth embodiments may be provided to form additional fortieth embodiments in which the multiple fluid circuits include a respective pumping tube segment for each of the component fluids, each being joined to the common outlet. Variations of the fortieth embodiments may be provided to form additional fortieth embodiments in which one of the respective inlets includes a water inlet connectable to a water purification plant to deliver water as one of the two or more component fluids, the one of the respective inlets having a sterilizing filter with a pore size sufficiently small to filter and sterilize water flowing into the circuit component through the one of the respective inlets. Variations of the fortieth embodiments may be provided to form additional fortieth embodiments in which a data reader, attached to the circuit component, storing data indicating data indicating at least one characteristic of a usage history of the circuit component. Variations of the fortieth embodiments may be provided to form additional fortieth embodiments that include a data reader, attached to the circuit component, storing data indicating data indicating a type of the circuit component. Variations of the fortieth embodiments may be provided to form additional fortieth embodiments that include a data reader, attached to the circuit component, storing data indicating a first time the circuit component was first wetted. Variations of the fortieth embodiments may be provided to form additional fortieth embodiments in which the circuit component internal fluid compartment is sterile as a result of the circuit component being a sterile disposable.

According to forty-first embodiments, the disclosed subject matter includes a system for providing medicament. A circuit component has multiple fluid circuits interconnected to permit two or more component fluids to be combined to form a product medicament, the multiple fluid circuits having respective inlets for each of the two or more component fluids and a common outlet, the common outlet being fluidly connected by the circuit component to the respective inlets to provide a combined medicament product. The circuit component defines a sealed internal fluid compartment defined by the multiple fluid circuits is isolated from an external environment, including the respective inlets. The circuit component includes one or more concentration measurement stations including fluid conductivity and temperature measurement portions. A controller with sensor components generates conductivity and temperature signals, the sensor components engaging with conductivity and temperature measurement portions of the circuit component that are positioned to detect temperature and conductivity of mixtures of the two or more components.

Variations of the forty-first embodiments may be provided to form additional forty-first embodiments in which the sealed internal fluid compartment has a sterile barrier that includes a sterilizing filter positioned at at least one of the respective inlets and having a pore size sufficiently small to filter and sterilize a respective one of the component fluids that may flow therethrough. Variations of the forty-first embodiments may be provided to form additional forty-first embodiments in which the multiple fluid circuits include a respective pumping tube segment for each of the component fluids, each being joined to the common outlet. Variations of the forty-first embodiments may be provided to form additional forty-first embodiments that include a water purification plant connected to the circuit component to deliver water, the water being one of the two or more component fluids, the water purification plant being connected through one of the respective inlets, the one of the respective inlets having a sterilizing filter with a pore size sufficiently small to filter and sterilize water flowing into the circuit component through the one of the respective inlets. Variations of the forty-first embodiments may be provided to form additional forty-first embodiments that include a controller the controller being adapted to receive prior use data indicating a period of time since the multiple fluid circuits interior volumes were first wetted and to output a command signal indicating whether the circuit component is safe to use. Variations of the forty-first embodiments may be provided to form additional forty-first embodiments that include a data reader, connected to the controller, that sends status data to the controller, the status data being derived at least in part on data from stored data read by the data reader from a data store attached to the circuit component. Variations of the forty-first embodiments may be provided to form additional forty-first embodiments in which the stored data indicates a type of the circuit component. Variations of the forty-first embodiments may be provided to form additional forty-first embodiments in which the stored data indicates a date and time when the circuit component was first wetted. Variations of the forty-first embodiments may be provided to form additional forty-first embodiments that include a treatment device connected to the common outlet and being of a type that requires a sterile medicament. Variations of the forty-first embodiments may be provided to form additional forty-first embodiments in which the treatment device includes a blood processing treatment device. Variations of the forty-first embodiments may be provided to form additional forty-first embodiments in which the treatment device includes an extracorporeal blood treatment device. Variations of the forty-first embodiments may be provided to form additional forty-first embodiments in which the circuit component internal fluid compartment is sterile as a result of the circuit component being a product of manufacture that includes sealing a disposable unit and sterilizing it.

According to forty-second embodiments, the disclosed subject matter includes a method of performing an extracorporeal blood treatment. The method includes, at a first time, flowing sterile component fluids to form a medicament into a sterile compartment, the flowing including wetting the sterile compartment. The method includes mixing the sterile component fluids to form a medicament and supplying the same, at the first time, to a medical treatment apparatus for providing a medical treatment. The method includes at a second time, with a controller and responsively to use-permission data, permitting or preventing a further flowing the sterile component fluids to form a medicament into the sterile compartment. The method includes at the second time, upon initially preventing the further flowing, permitting a further flowing sterile component fluids to form a medicament into the same or a new sterile compartment after a replacement or sterilization of the sterile compartment so as to ensure sterility thereof, the permitting including verifying that the sterile compartment has been replaced or sterilized. The use-permission data is indicative of a time since the sterile compartment was first wetted for preparing medicament, a volume of fluid processed by the sterile compartment, a date of manufacture of the sterile compartment, a lot number of the sterile compartment, or a type of the sterile compartment.

Variations of the forty-second embodiments may be provided to form additional forty-second embodiments in which measuring a conductivity and temperature of a mixture resulting from the mixing.

According to forty-third embodiments, the disclosed subject matter includes a method of performing an extracorporeal blood treatment. The method includes, at a first time, flowing component fluids to form a medicament into a sterile compartment, the flowing including wetting the sterile compartment and sterilizing the component fluids to ensure the component fluids and sterile compartment are sterile after the first time. The method includes, mixing the component fluids to form a medicament and supplying the same, at the first time, to a medical treatment apparatus for providing a medical treatment. The method includes, at a second time, with a controller and responsively to use-permission data, permitting or preventing a further flowing component fluids to form a medicament into the sterile compartment, the second flowing including sterilizing the component fluids. The method includes, at the second time, upon initially preventing the further flowing, permitting a further flowing component fluids to form a medicament into the same or a new sterile compartment after a replacement or sterilization of the sterile compartment so as to ensure sterility thereof, the permitting including verifying that the sterile compartment has been replaced or sterilized. The use-permission data is indicative of a time since the sterile compartment was first wetted for preparing medicament, a volume of fluid processed by the sterile compartment, a date of manufacture of the sterile compartment, a lot number of the sterile compartment, or a type of the sterile compartment. The forty-third embodiment may be modified to include measuring a conductivity and temperature of a mixture resulting from the mixing.

According to forty-fourth embodiments, the disclosed subject matter includes a method of providing sterile dialysate for a treatment. The method includes pumping sterile water and sterile concentrates into a mixing component. The method includes using the mixing component, mixing the sterile water and sterile medicaments so as to generate a sterile medicament. The method includes flowing the sterile medicament to a blood treatment system.

Variations of the forty-fourth embodiments may be provided to form additional forty-fourth embodiments in which the pumping sterile water includes purifying tap water and sterile-filtering a product of the purifying. Variations of the forty-fourth embodiments may be provided to form additional forty-fourth embodiments in which the pumping sterile concentrates includes providing a sealed sterile container pre-filled with concentrate and sterilized. Variations of the forty-fourth embodiments may be provided to form additional forty-fourth embodiments in which the pumping sterile concentrates includes providing a sealed sterile container pre-filled with sterile concentrate and sterilizing the container. Variations of the forty-fourth embodiments may be provided to form additional forty-fourth embodiments that include flowing the sterile medicament at a first time for a first treatment, stopping the pumping and mixing, setting up for a second treatment at a second time while permitting the mixing component to remain wetted in the rest interval between the first and second times, and repeating the pumping and mixing to perform a second treatment at the second time. Variations of the forty-fourth embodiments may be provided to form additional forty-fourth embodiments that include flowing the sterile medicament at a first time for a first treatment, stopping the pumping and mixing, setting up for a second treatment at a second time while permitting the mixing component to remain wetted in the interval between the first and second times, using a controller, determining whether a predetermined time interval has elapsed since the first time and repeating the pumping and mixing to perform a second treatment at the second time only if the rest interval does not exceed the predetermined time interval.

It will be appreciated that the modules, processes, systems, and sections described above can be implemented in hardware, hardware programmed by software, software instruction stored on a non-transitory computer readable medium or a combination of the above. For example, a method for controlling the generating of a medicament or treatment fluid (or methods therewithin such as for the generating of purified water) can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hardwired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of control systems, sensors, electromechanical effecters and/or computer programming arts.

Moreover, embodiments of the disclosed method, system, and computer program product can be implemented in software executed on a programmed general purpose computer, a special purpose computer, a microprocessor, or the like.

It is, thus, apparent that there is provided, in accordance with the present disclosure, medicament preparation and treatment devices, methods, and systems. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicant intends to embrace all such alternatives, modifications, equivalents, and variations that are within the spirit and scope of the present invention.

The invention claimed is:

1. A medicament preparation system for preparing a medicament, comprising:
   a water purification module with a tap water inlet and a purified water outlet;
   a medicament proportioning module that is interoperable with a replaceable fluid circuit that includes
   a purified water inlet that receives purified water from the purified water outlet of the water purification module,
   a product medicament outlet configured to output the medicament,
   a medicament supply channel fluidly connecting the purified water inlet to the product medicament outlet, and
   a plurality of pumping tube segments, that include a first pumping tube segment fluidly connected between the purified water inlet and the medicament supply channel and a second pumping tube segment fluidly connected between a first concentrate container and the medicament supply channel;
   at least the first concentrate container connected by at least a portion of the replaceable fluid circuit to the product medicament outlet;
   a first concentration measurement sensor station positioned in a flow path of the replaceable fluid circuit; and
   a controller programmed to calculate iteratively a concentration of a first concentrate from the first concentrate container and the purified water from a signal generated by the first concentration measurement sensor station and to regulate one or both of a first pumping actuator engaged with the first pumping tube segment and a second pumping actuator engaged with the second pumping tube segment, responsively to the concentration of the first concentrate and the purified water, wherein
   the controller is programmed to calculate iteratively a concentration of a second concentrate and the first concentrate and the purified water from a signal generated by a second concentration measurement sensor station and to regulate at least two of the first and second pumping actuators and a third pumping actuator engaged with a third pumping tube segment, that connects a second concentrate container to the medicament supply channel, responsively to the concentration of the first and second concentrates and the purified water.

2. The medicament preparation system according to claim 1, wherein the replaceable fluid circuit is contained in a fluid circuit cartridge that is insertable into the water purification module.

3. The medicament preparation system according to claim 1, wherein the at least the first concentrate container is fluidly connected to a second concentrate container.

4. The medicament preparation system according to claim 3, wherein the first concentrate container is fluidly connected to the second concentrate container by the second pumping tube segment and the third pumping tube segment.

5. The medicament preparation system according to claim 3, wherein the first concentrate is a liquid and the second concentrate is a dry solid.

6. The medicament preparation system according to claim 1, wherein the replaceable fluid circuit further includes:
   a sterile circuit with multiple fluid circuits interconnected to permit two or more component fluids to be combined to form a product medicament, the multiple fluid circuits having respective inlets for each of the two or more component fluids and a common outlet, the common outlet being fluidly connected by the sterile circuit to the respective inlets to provide a combined medicament product;
   the sterile circuit defining a sterile barrier such that internal fluid compartment defined by the multiple fluid circuits is isolated from an external environment, including the respective inlets;
   one or more concentration measurement sensor stations including fluid conductivity and temperature measurement portions which are positioned within the fluid circuit to detect conductivity and temperature of mixtures of the two or more component fluids and further positioned, when the sterile circuit is loaded in the medicament preparation system, to engage with sensor components thereof to generate conductivity and temperature signals of the mixtures.

7. The medicament preparation system according to claim 6, wherein the sterile barrier includes a sterilizing filter positioned at least on one of the respective inlets and having a pore size sufficiently small to filter and sterilize a respective one of the component fluids that may flow therethrough.

8. The medicament preparation system according to claim 7, wherein the multiple fluid circuits include a respective pumping tube segment for each of the component fluids, each being joined to the common outlet.

9. The medicament preparation system according to claim 8, wherein one of the respective inlets includes a water inlet connectable to a water purification plant to deliver water as one of the two or more component fluids, the one of the respective inlets having the sterilizing filter with the pore size sufficiently small to filter and sterilize water flowing into the sterile circuit through the one of the respective inlets.

10. The medicament preparation system according to claim 6, wherein the replaceable fluid circuit further comprises a data reader, attached to the sterile circuit, storing data indicating data indicating at least one characteristic of a usage history of the sterile circuit.

11. The medicament preparation system according to claim 6, wherein the replaceable fluid circuit further comprises a data reader, attached to the sterile circuit, storing data indicating data indicating a type of the sterile circuit.

12. The medicament preparation system according to claim 6, wherein the replaceable fluid circuit further comprises a data reader, attached to the sterile circuit, storing data indicating a first time the sterile circuit was first wetted.

13. The medicament preparation system according to claim 6, wherein the sterile circuit has an internal fluid compartment that is sterile as a result of the sterile circuit being a sterile disposable.

14. The medicament preparation system according to claim 1, wherein
the medicament proportioning module includes a concentrate pump section and a water pump section that engage respective pump actuators to transfer purified water and concentrate to the medicament supply channel of the replaceable fluid circuit, the medicament supply channel having the product medicament outlet that is connected to supply a mixture of the water and concentrates transferred to the medicament supply channel; and
the medicament supply channel includes an accumulator.

15. The medicament preparation system according to claim 14, wherein
the accumulator has an internal volume whose size is selected to be no more than twice a volume predetermined to be necessary to permit the respective pump actuators to operate at a constant speed without starving flow to a predefined consuming device connectable to the product medicament outlet, wherein the predefined consuming device draws medicament at variable rate.

16. The medicament preparation system according to claim 1, wherein
the water purification module includes deionization filters positioned between the tap water inlet and the purified water outlet to purify the water received from the tap water inlet,
the medicament proportioning module receives the replaceable fluid circuit and has a concentrate pump section and a water pump section that engage respective pump actuators to transfer purified water and concentrate to a medicament supply channel of the replaceable fluid circuit, the medicament supply channel having the product medicament outlet that is connected to supply a mixture of the water and concentrates transferred to the medicament supply channel, and
the medicament supply channel includes an accumulator with a rigid button supporting expansion and contraction of an internal volume of the accumulator.

17. The medicament preparation system according to claim 16, wherein
the accumulator includes an elastic web, and
the accumulator is supported by the elastic web in one or more directions or moments other than a direction of expansion of the internal volume of the accumulator,
the rigid button is urged by an urging element positioned and oriented to resist the expansion of the internal volume of the accumulator, and
the rigid button makes no friction-causing sliding engagement with other portions of the accumulator, whereby a pressure-volume characteristic of the internal volume of the accumulator is determined by the urging element.

18. The medicament preparation system according to claim 1, wherein
the medicament proportioning module maintains a target average pressure at the product medicament outlet such that an attached medicament consuming device can draw fluid on-demand at a current pressure at the product medicament outlet, and
the medicament proportioning module includes an accumulator upstream of the product medicament outlet to permit irregular or periodic draw of medicament therefrom without a need for a concomitant irregular or periodic change in a pumping rate of the first, second, and third pumping actuators.

19. The medicament preparation system according to claim 18, wherein a medicament supply channel houses the accumulator, and
the accumulator has an expandable interior volume.

20. The medicament preparation system according to claim 19, wherein the accumulator is at least partly integrated in a replaceable cartridge.

* * * * *